United States Patent
Huang et al.

(10) Patent No.: US 12,049,501 B2
(45) Date of Patent: *Jul. 30, 2024

(54) CD3-BINDING MOLECULES CAPABLE OF BINDING TO HUMAN AND NON-HUMAN CD3

(71) Applicant: MacroGenics, Inc., Rockville, MD (US)

(72) Inventors: Ling Huang, Bethesda, MD (US); Leslie S. Johnson, Rockville, MD (US)

(73) Assignee: MacroGenics, In, Rockville, MD (US)

( * ) Notice: Subject to any disclaimer, the term of this patent is extended or adjusted under 35 U.S.C. 154(b) by 413 days.

This patent is subject to a terminal disclaimer.

(21) Appl. No.: 17/393,682

(22) Filed: Aug. 4, 2021

(65) Prior Publication Data
US 2022/0056131 A1   Feb. 24, 2022

Related U.S. Application Data

(60) Continuation of application No. 16/168,559, filed on Oct. 23, 2018, now Pat. No. 11,111,299, which is a continuation of application No. 15/414,303, filed on Jan. 24, 2017, now Pat. No. 10,150,812, which is a division of application No. 14/118,523, filed as application No. PCT/US2012/038219 on May 16, 2012, now Pat. No. 9,587,021.

(60) Provisional application No. 61/530,353, filed on Sep. 1, 2011, provisional application No. 61/488,716, filed on May 21, 2011.

(51) Int. Cl.
| | |
|---|---|
| C07K 16/28 | (2006.01) |
| C03C 17/38 | (2006.01) |
| C03C 17/42 | (2006.01) |
| C07K 16/32 | (2006.01) |
| G02B 5/08 | (2006.01) |
| H01L 31/054 | (2014.01) |

(52) U.S. Cl.
CPC .......... *C07K 16/2809* (2013.01); *C03C 17/38* (2013.01); *C03C 17/42* (2013.01); *C07K 16/2803* (2013.01); *C07K 16/2827* (2013.01); *C07K 16/2863* (2013.01); *C07K 16/32* (2013.01); *G02B 5/0808* (2013.01); *H01L 31/0547* (2014.12); *C03C 2217/445* (2013.01); *C03C 2217/465* (2013.01); *C03C 2217/479* (2013.01); *C07K 2317/24* (2013.01); *C07K 2317/31* (2013.01); *C07K 2317/33* (2013.01); *C07K 2317/52* (2013.01); *C07K 2317/56* (2013.01); *C07K 2317/71* (2013.01); *C07K 2317/732* (2013.01); *C07K 2317/92* (2013.01); *Y02E 10/52* (2013.01)

(58) Field of Classification Search
None
See application file for complete search history.

(56) References Cited

U.S. PATENT DOCUMENTS

| | | |
|---|---|---|
| 7,381,803 B1 | 6/2008 | Weiner et al. |
| 7,575,923 B2 | 8/2009 | Dorken et al. |
| 7,635,472 B2 | 12/2009 | Kufer et al. |
| 7,728,114 B2 | 6/2010 | Mach et al. |
| 7,883,703 B2 | 2/2011 | Weiner et al. |
| 11,111,299 B2* | 9/2021 | Huang ............... G02B 5/0808 |
| 2004/0259075 A1 | 12/2004 | Dimitrov et al. |
| 2006/0099216 A1 | 5/2006 | Cardy et al. |
| 2007/0081993 A1 | 4/2007 | Kufer et al. |
| 2009/0252683 A1 | 10/2009 | Kischel et al. |
| 2010/0150918 A1 | 6/2010 | Kufer et al. |
| 2010/0183554 A1 | 7/2010 | Mach et al. |
| 2010/0209437 A1 | 8/2010 | Elson et al. |
| 2010/0260668 A1 | 10/2010 | Ghayur et al. |

FOREIGN PATENT DOCUMENTS

| | | |
|---|---|---|
| EP | 0623679 | 11/1994 |
| WO | WO 2004/106381 | 12/2004 |
| WO | WO 2004/106383 | 12/2004 |
| WO | WO 2007/042261 | 4/2007 |
| WO | WO 2007/117600 | 10/2007 |
| WO | WO 2008/119566 | 10/2008 |
| WO | WO 2008/119567 | 10/2008 |
| WO | WO 2010/027797 | 3/2010 |
| WO | WO 2010/042904 | 4/2010 |
| WO | WO 2011/050262 | 4/2011 |

OTHER PUBLICATIONS

Abramowicz, D. et al. (1989) "*Release of Tumor Necrosis Factor, Interleukin-2, and Gamma-Interferon in Serum After Injection of OKT3 Monoclonal Antibody in Kidney Transplant Recipients*," Transplantation 47:606-608.
Alegre, M.L. et al. (1994) "*A Non-Activating "Humanized" Anti-CD3 Monoclonal Antibody Retains Immunosuppressive Properties In Vivo*," Transplantation 57:1537-1543.
Alison, M.R. et al. (2009) "*Stem Cells and Lung Cancer: Future Therapeutic Targets?*" Expert Opin. Biol. Ther. 9(9):1127-1141.
Altschul, S.F. (1991) "*Amino Acid Substitution Matrices From an Information Theoretic Perspective*," J. Mol. Biol. 219:555-565.
Ampel et al. (2002) "*In Vitro Whole-Blood Analysis of Cellular Immunity in Patients with Active Coccidioidomycosis by Using the Antigen Preparation T27K*," Clin. Diagn. Lab. Immunol. 9:1039-1043.

(Continued)

*Primary Examiner* — Zachary S Skelding
(74) *Attorney, Agent, or Firm* — MEDLER FERRO WOODHOUSE & MILLS PLLC

(57) ABSTRACT

The present invention relates to CD3-binding molecules capable of binding to human and non-human CD3, and in particular to such molecules that are cross-reactive with CD3 of a non-human mammal (e.g., a cynomolgus monkey). The invention also pertains to uses of such antibodies and antigen-binding fragments in the treatment of cancer, autoimmune and/or inflammatory diseases and other conditions.

25 Claims, 21 Drawing Sheets

Specification includes a Sequence Listing.

(56) References Cited

OTHER PUBLICATIONS

Armour, K.L. et al. (1999) "Recombinant Human IgG Molecules Lacking Fcgamma Receptor I Binding and Monocyte Triggering Activities," Eur. J. Immunol. 29:2613-24.

Arndt, R. (1984) "Demonstration of C3-Binding Circulating Immune Complexes Using Raji, Conglutinin and Anti-C3 Assays—A Critical Review," Immun. Infekt. 12(1):3-11 (Abstract Only).

Aruffo, A. et al. (1987) "Molecular Cloning of a CD28 cDNA by a High-Efficiency COS Cell Expression System," Proc. Natl. Acad. Sci. (U.S.A.) 84:8573-8577.

Atzenia, F. et al. (2002) "Induction of CD69 Activation Molecule on Human Neutrophils by GM-CSF, IFN-γ, and IFN-α," Cellular Immunol. 220(1): 20-29.

Baeuerle, P et al. (2008) "BiTER©: A New Class of Antibodies That Recruit T Cells," Drugs of the Future 33:137-147.

Barderas, R. et al. (2008) "Affinity Maturation of Antibodies Assisted by In Silico Modeling," Proc. Natl. Acad. Sci. (U.S.A.) 105(26):9029-9034.

Bargou, et al. 2008) "Tumor Regression in Cancer Patients by Very Low Doses of a T Cell-Engaging Antibody," Science 321: 974-977.

Bird et al. (1988) "Single-Chain Antigen-Binding Proteins," Science 242:423-426.

Bispecific Antibodies, R.E. Kontermann (Ed), Baeuerle et al. Bispecific T Cell Engager for Cancer Therapy, Ch. 15, pp. 273-287 (2011).

Bortoletto, N. et al. (2002) "Optimizing Anti-CD3 Affinity for Effective T Cell Targeting Against Tumor Cells," Eur. J. Immunol. 32:3102-3107.

Bostrom, J. et al. (2009) "Improving Antibody Binding Affinity and Specificity for Therapeutic Development," Methods Mol. Biol. 525:353-376.

Brown et al. (1987) "Tumor-Specific Genetically Engineered Murine/Human Chimeric Monoclonal Antibody," Cancer Res. 47:3577-3583.

Bryant et al. (2004) "EGF Activates Intracellular and Intercellular Calcium Signaling by Distinct Pathways in Tumor Cells," Cancer Biology and Therapy 3:1243-1249.

Buhler et al. (2009) "Target-dependent T-cell Activation by Coligation With a PSMA x CD3 Diabody Induces Lysis of Prostate Cancer Cells," Immunother. 32(6):565-573.

Call, M.E. et al. (2007) "Common Themes in the Assembly and Architecture of Activating Immune Receptors," Nat. Rev. Immunol. 7:841-850.

Carter, P. et al. (1992) "Humanization of an Anti-p185her2 Antibody for Human Cancer Therapy," Proc. Natl. Acad. Sci. (U.S.A.) 89:4285-4289.

Castriconi et al. (2004) "Identification of 4Ig—B7—H3 as a Neuroblastoma-Associated Molecule That Exerts a Protective Role From an NK Cell-Mediated Lysis," Proc. Natl. Acad. Sci. (U.S.A.) 101(34):12640-12645.

Chapoval, A. et al. (2001) "B7—H3: A Costimulatory Molecule for T Cell Activation and IFN-γ Production," Nature Immunol. 2:269-274.

Charafe-Jauffret, E. et al. (2009) "Breast Cancer Stem Cells: Tools and Models to Rely On," BMC Cancer 9:202, 10 pages.

Clark, E.A. et al. (1985) "Role of the Bp35 Cell Surface Polypeptide in Human B-Cell Activation," Proc. Natl. Acad. Sci. (USA) 82(6):1766-1770.

Co, M. S. et al. (1991) "Humanized Antibodies for Antiviral Therapy," Proc. Natl. Acad. Sci. (U.S.A.) 88:2869-2873.

Co, M.S. et al. (1992) "Chimeric and Humanized Antibodies With Specificity for the CD33 Antigen," J. Immunol. 148:1149-1154.

Cole, M.S. et al. (1997) "Human IgG2 Variants of Chimeric Anti-CD3 are Nonmitogenic to T cells," J. Immunol. 159(7):3613-3621.

Cole, M.S. et al. (1999) "Hum291, A Humanized Anti-CD3 Antibody, is Immunosuppressive to T Cells While Exhibiting Reduced Mitogenicity in vitro," Transplantation 68:563-571 (Web Version; 17 pages).

Cosimi, A.B. et al. (1981) "Use of Monoclonal Antibodies to T-Cell Subsets for Immunologic Monitoring and Treatment in Recipients of Renal Allografts," N. Engl. J. Med. 305:308-314.

Crispin et al. (2010) "T cells as Therapeutic Targets in SLE," Nat. Rev. Rheumatol. 6:317-325.

Daugherty et al. (1991) "Polymerase Chain Reaction Facilitates the Cloning, CDR-Grafting, and Rapid Expression of a Murine Monoclonal Antibody Directed Against the CD18 Component of Leukocyte Integrins," Nucl. Acids Res. 19:2471-2476.

Drexler, H.G. et al. (1998) "History and Classification of Human Leukemia-Lymphoma Cell Lines," Leuk. Lymphoma 31(3-4):305-316.

Duncan, A.R. et al. (1988) "Localization of the Binding Site for the Human High-Affinity Fc Receptor on IgG," Nature 332:563-564.

Eddy, S. R. (2004) "Where Did the BLOSUM62 Alignment Score Matrix Come From," Nature Biotechnology 22:1035-1036.

Erter et al. (2010) "New Targets of Therapy in T-Cell Lymphomas," Current Drug Targets 11:482-493.

Ferran, C. et al. (1990) "Cytokine-Related Syndrome Following Injection of Anti-CD3 Monoclonal Antibody: Further Evidence for Transient In Vivo T Cell Activation," Eur. J. Immunol. 20:509-515.

Finlay, W.J. et al. (2009) "Affinity Maturation of a Humanized Rat Antibody for Anti-RAGE Therapy: Comprehensive Mutagenesis Reveals a High Level of Mutational Plasticity Both Inside and Outside the Complementarity-Determining Regions," J. Mol. Biol. 388(3):541-558.

Fogh, J. (1978) "Cultivation, Characterization, and Identification of Human Tumor Cells With Emphasis on Kidney, Testis and Bladder Tumors," Natl. Cancer Inst. Monogr. 49:5-9.

Ganesan, A. (2006) "Solid-Phase Synthesis in the Twenty-First Century," Mini Rev. Med. Chem. 6(1):3-10.

Ghotra, V.P. et al. (2009) "The Cancer Stem Cell Microenvironment and Anti-Cancer Therapy," Int. J. Radiat. Biol. 85(11):955-962.

Giard, D.J. et al. (1973) "in vitro Cultivation of Human Tumors: Establishment of Cell Lines Derived From a Series of Solid Tumors," J. Natl. Cancer Inst. 51:1417-1423 (Abstract Only).

Glaser et al. (1992) "Antibody Engineering by Codon-Based Mutagenesis in a Filamentous Phage Vector System," J. Immunology 149:3903-39013.

Gorman, S. D. et al. (1991) "Reshaping a Therapeutic CD4 Antibody," Proc. Natl. Acad. Sci. (U.S.A.) 88:4181-4185.

Govers et al. (2009) "T Cell Receptor Gene Therapy: Strategies for Optimizing Transgenic TCR Pairing" Trends in Molecular Medicine 16:77-87.

Gramatzki, M. et al. (1995) "Therapy With OKT3 Monoclonal Antibody in Refractory T Cell Acute Lymphoblastic Leukemia Induces Interleukin-2 Responsiveness," Leukemia 9(3):382-390 (Abstract Only).

Gupta, P.B. et al. (2009) "Cancer Stem Cells: Mirage or Reality?" Nat. Med. 15(9):1010-1012.

Gustchina, E. et al. (2009) "Affinity Maturation by Targeted Diversification of the CDR-H2 Loop of a Monoclonal Fab Derived From a Synthetic Naïve Human Antibody Library and Directed Against the Internal Trimeric Coiled-Coil of Gp41 Yields a Set of Fabs With Improved HIV-1 Neutralization Potency and Breadth," Virology 393(1):112-119.

Guy et al. (2009) "Organization of Proximal Signal Initiation at the TCR:CD3 Complex," Immunol Rev. 232:7-21 (Web Version; 21 pages).

Hackel, B.J. et al. (2010) "Stability and CDR Composition Biases Enrich Binder Functionality Landscapes," J. Mol. Biol. 401(1):84-96.

Heath et al. (1997) "The Human A33 Antigen is a Transmembrane Glycoprotein and a Novel Member of the Immunoglobulin Superfamily," Proc. Natl. Acad. Sci. (U.S.A.) 469-474.

Henikoff, J.G. (1992) "Amino Acid Substitution Matrices From Protein Blocks," Proc. Natl. Acad. Sci. (U.S.A.) 89:10915-10919.

Hermann, P.C. et al. (2009) "Pancreatic Cancer Stem Cells—Insights and Perspectives," Expert Opin. Biol. Ther. 9(10):1271-1278.

Herold, K.C. et al. (2002) "Anti-CD3 Monoclonal Antibody in New-Onset Type 1 Diabetes Mellitus," N. Engl. J. Med. 346:1692-1698.

(56) References Cited

OTHER PUBLICATIONS

Hirsch, R. et al. (1989) "Effects of In Vivo Administration of Anti-CD3 Monoclonal Antibody on T Cell Function in Mice. II. In Vivo Activation of T Cells," J. Immunol. 142:737-743.

Hofmeyer, K. et al. (2008) "The Contrasting Role of B7—H3," Proc. Natl. Acad. Sci. (U.S.A.) 105(30):10277-10278.

Houghten, R.A. (1985) "General Method for the Rapid Solid-Phase Synthesis of Large Numbers of Peptides: Specificity of Antigen-Antibody Interaction at the Level of Individual Amino Acids," Proc. Natl. Acad. Sci. (U.S.A.) 82(15):5131-5135.

Hutchins et al. (1995) "Improved Biodistribution, Tumor Targeting, and Reduced Immunogenicity in Mice With a Gamma 4 Variant of Campath-1H," Proc. Natl. Acad. Sci. (U.S.A.) 92:11980-11984.

Idusogie, E.E. et al. (2000) "Mapping of the C1q Binding Site on Rituxan, A Chimeric Antibody With a Human IgG Fc," J. Immunol. 164:4178-84.

Idusogie, E.E. et al. (2001) "Engineered Antibodies With Increased Activity to Recruit Complement," J. Immunol. 166:2571-75.

Isaacs et al. (2001) "From Bench to Bedside: Discovering Rules for Antibody Design, and Improving Serotherapy with Monoclonal Antibodies," Rheumatology 40: 724-738.

Jefferis, B.J. et al. (2002) "Interaction Sites on Human IgG-Fc for FcgammaR: Current Models," Immunol. Lett. 82:57-65.

Jefferis, R. et al. (1995) "Recognition Sites on Human IgG for Fc Gamma Receptors: The Role of Glycosylation," Immunol. Lett. 44:111-117.

Jefferis, R. et al. (1996) "Modulation of Fc(Gamma)R and Human Complement Activation by IgG3-Core Oligosaccharide Interactions," Immunol. Lett. 54:101-04.

Jeon, H.J. et al. (1998) "Establishment and Characterization of a Mantle Cell Lymphoma Cell Line," Br. J. Haematol. 102(5):1323-1326.

Jones, P.T. et al. (1986) "Replacing the Complementarity-Determining Regions in a Human Antibody With Those From a Mouse," Nature 321:522-525.

Karlin, S. et al. (1990) "Methods for Assessing the Statistical Significance of Molecular Sequence Features by Using General Scoring Schemes," Proc. Natl. Acad. Sci. (USA) 87:2264-2268.

Kettleborough, C.A. et al. (1991) "Humanization of a Mouse Monoclonal Antibody by CDR-Grafting: The Importance of Framework Residues on Loop Conformation," Protein Engineering 4:773-783.

Klingbeil et al. (1999) "Pharmacology and Safety Assessment of Humanized Monoclonal Antibodies for Therapeutic Use," Toxicology Pathology, 27(1):1-3.

Kohler, G. et al. (1975) "Continuous Cultures of Fused Cells Secreting Antibody of Predefined Specificity," Nature 256:495-497.

Krause, J.C. et al. (2011) "An Insertion Mutation That Distorts Antibody Binding Site Architecture Enhances Function of a Human Antibody," MBio 2(1), 8 pages.

Kuan, C.T. et al. (2010) "Affinity-Matured Anti-Glycoprotein NMB Recombinant Immunotoxins Targeting Malignant Gliomas and Melanomas," Int. J. Cancer 129: 111-121.

Kung, P. et al. (1979) "Monoclonal Antibodies Defining Distinctive Human T Cell Surface Antigens," Science 206:347-349.

Lawson, J.C. et al. (2009) "Cancer Stem Cells in Breast Cancer and Metastasis," Breast Cancer Res. Treat. 118(2):241-254.

Lee et al. (2010) "The Distribution of the Therapeutic Monoclonal Antibodies Cetuximab and Trastuzumab Within Solid Tumors," BMC Cancer 10:255 (11 pages).

LoBuglio, A.F. et al. (1989) "Mouse/Human Chimeric Monoclonal Antibody in Man: Kinetics and Immune Response," Proc. Natl. Acad. Sci. (U.S.A.) 86:4220-4224.

Lonberg, N. et al. (1995) "Human Antibodies From Transgenic Mice," Int. Rev. Immunol 13:65-93—(Abstract Only).

Ludvigsson, J. (2009) "The Role of Immunomodulation Therapy in Autoimmune Diabetes," J. Diabetes Sci. Technol. 3:320-330.

Lund et al. (1991) "Human Fc Gamma RI and Fc Gamma RII Interact With Distinct but Overlapping Sites on Human IgG," J. Immunol. 147:2657-2662.

Lund et al. (1992) "Multiple Binding Sites on the CH2 Domain of IgG for Mouse Fc Gamma RII," Mol. Immunol. 29:53-59.

Lund, J. et al. (1995) "Oligosaccharide-Protein Interactions in IgG Can Modulate Recognition by Fc Gamma Receptors," FASEB J. 9:115-119.

Lund, J. et al. (1996) "Multiple Interactions of IgG With Its Core Oligosaccharide Can Modulate Recognition by Complement and Human Fc Gamma Receptor I and Influence the Synthesis of Its Oligosaccharide Chains," J. Immunol. 157:4963-4969.

Maeda, H. et al. (1991) "Construction of Reshaped Human Antibodies With HIV-Neutralizing Activity," Human Antibodies Hybridoma 2:124-134 (Abstract Only).

Mangham, D.C. et al. (1999) "A Novel Immunohistochemical Detection System Using Mirror Image Complementary Antibodies (MICA)," Histopathology 35(2):129-133.

Marchis-Mouren, G. et al. (1988) "HT 29, A Model Cell Line: Stimulation by the Vasoactive Intestinal Peptide (VIP); VIP Receptor Structure and Metabolism," Biochimie 70(5):663-671.

Masharani, U.B. et al. (2010) "Teplizumab Therapy for Type 1 Diabetes," Expert Opin Biol Ther. 10:459-465.

Meng, G. et al. (1998) "The Effect of Anti-CD3-Immunotoxin on T Lymphocyte Function in vitro," Transpl. Immunol. 6(1):53-59.

Merrifield, B. (1986) "Solid Phase Synthesis," Science 232:341-347.

Midtvedt, K. et al. (2003) "Individualized T Cell Monitored Administration of ATG Versus OKT3 in Steroid-Resistant Kidney Graft Rejection," Clin. Transplant. 17(1):69-74.

Mittal, S. et al. (2009) "Cancer Stem Cells: The Other Face of Janus," Amer. J. Med. Sci. 338(2):107-112.

Montgomery, D.L. et al. (2009) "Affinity Maturation and Characterization of a Human Monoclonal Antibody Against HIV-1 gp41," MAbs 1(5):462-474.

Moore, P.A. et al. (2011) "Application of Dual Affinity Retargeting Molecules to Achieve Optimal Redirected T-Cell Killing of B-Cell Lymphoma," Blood J. 117(17):4542-4551.

Munoz et al. (2001) "Interleukin-3 Receptor α Chain (CD123) is Widely Expressed in Hematologic Malignancies," Haematologica 86:1261-1269.

NHP Reagent Resource, "Commercial Reagent Cross-Reactivity for CD3," NIH Nonhuman Primate Reagent Resource; nhpreagents.org/NHP/clonelist.aspx?ID=77; online database (2014-2018).

Nooij, F.J. et al. (1986) "Differentiation Antigens on Rhesus Monkey Lymphocytes. I. Identification of T Cells Bearing CD3 And CD8, and of a Subset of CD8-Bearing Cells," Eur. J. Immunol. 16(8):975-979.

Peeters et al. (2001) "Production of Antibodies and Antibody Fragments in Plants," Vaccine 19:2756-2761.

Pollock et al.(1999) "Transgenic Milk as a Method for the Production of Recombinant Antibodies," J. Immunol Methods 231:147-157.

Portoles et al. (2009) "The TCR/CD3 Complex: Opening the Gate to Successful Vaccination," Current Pharmaceutical Design 15:3290-3330.

Press, O.W. et al. (1987) "Monoclonal Antibody 1F5 (Anti-CD20) Serotherapy of Human B Cell Lymphomas," Blood 69:584-591.

Presta, L.G. et al. (2002) "Engineering Therapeutic Antibodies for Improved Function," Biochem. Soc. Trans. 30:487-90.

Reddy, M.P. et al. (2000) "Elimination of Fc Receptor-Dependent Effector Functions of a Modified IgG4 Monoclonal Antibody to Human CD4," J. Immunol. 164:1925-1933.

Riechmann, L. et al. (1988) "Reshaping Human Antibodies for Therapy," Nature 332:323-327.

Riha, P. et al. (2010) "CD28 Co-Signaling in the Adaptive Immune Response," Self/Nonself 1(3):231-240.

Rudikoff, S. etc. (1982) "Single Amino Acid Substitution Altering Antigen-Binding Specificity," Proc. Natl. Acad. Sci. (U.S.A.) 79(6):1979-1983.

Saatian, B. et al. (2004) "Expression of Genes for B7—H3 and Other T Cell Ligands by Nasal Epithelial Cells During Differentiation and Activation," Amer. J. Physiol. Lung Cell. Mol. Physiol. 287:L217-L225.

(56) References Cited

OTHER PUBLICATIONS

Salaverria, I. et al. (2006) "*Mantle Cell Lymphoma: From Pathology and Molecular Pathogenesis to New Therapeutic Perspectives*," Haematologica 91:11-16.

Sato, K. et al. (1993) "*Reshaping a Human Antibody to Inhibit the Interleukin 6-dependent Tumor Cell Growth*," Cancer Res 53:851-856.

Schatton, T. et al. (2009) "*Identification and Targeting of Cancer Stem Cells*," Bioessays 31(10):1038-1049.

Schier et al. (1996) "*Isolation of Picomolar Affinity Anti-c-erbB-2 Single-Chain Fv by Molecular Evolution of the Complementarity Determining Regions in the Center of the Antibody Binding Site*," J. Mol. Bio. 263:551-567.

Scopelliti, A. et al. (2009) "*Therapeutic Implications of Cancer Initiating Cells*," Expert Opin. Biol. Ther. 9(8):1005-1016.

Shaw et al. (1987) "*Characterization of a Mouse/Human Chimeric Monoclonal Antibody (17-1A) to a Colon Cancer Tumor-Associated Antigen*," J. Immunol. 138:4534-4538.

Shields, R.L. et al. (2002) "*Lack of Fucose on Human IgG1 N-Linked Oligosaccharide Improves Binding to Human Fcgamma RIII and Antibody-Dependent Cellular Toxicity*," J. Biol. Chem. 277(30):26733-26740.

Shields, R.L. et al. (2001) "*High Resolution Mapping of the Binding Site on Human IgG1 for Fc Gamma RI, Fc Gamma RII, Fc Gamma RIII, and FcRn and Design of IgGI Variants With Improved Binding to the Fc gamma R*," J. Biol. Chem. 276:6591-6604.

Soubrane et al. (1993) "*Biologic Response to Anti-CD16 Monoclonal Antibody Therapy in a Human Immunodeficiency Virus-Released Immune Thrombocytopenic Purpura Patient*," Blood 81(1):15-19.

St. Clair E.W. (2009) "*Novel Targeted Therapies for Autoimmunity*," Curr. Opin. Immunol. 21(6):648-657.

Steidl, S. et al. (2008) "*In Vitro Affinity Maturation of Human GM-CSF Antibodies by Targeted CDR-Diversification*," Mol. Immunol. 46(1):135-144.

Stephan, J. et al. (1999) "*Selective Cloning of Cell Surface Proteins Involved in Organ Development: Epithelial Glycoprotein is Involved in Normal Epithelial Differentiation*," Endocrinol. 140:5841-5854.

Sun, M. et al. (2002) "*Characterization of Mouse and Human B7—H3 Genes*," J. Immunol. 168:6294-6297.

Sun, Y et al. (2006) "*B7—H3 and B7—H4 Expression in Non-Small-Cell Lung Cancer*," Lung Cancer 53:143-151.

Tempest, P.R. et al. (1991) "*Reshaping a Human Monoclonal Antibody to Inhibit Human Respiratory Syncytial Virus Infection in vivo*," Bio/Technology 9:266-271 (Abstract Only).

Thakur et al. (2010) "*Cancer therapy with bispecific antibodies: Clinical experience*," Curr Opin Mol. THer. 12(3):340-349.

Thistlethwaite, J.R. Jr. et al. (1988) "*Complications and Monitoring of OKT3 Therapy*," Am. J. Kidney Dis. 11:112-119 (Abstract Only).

Van der Merwe et al. (2010) "*Mechanisms for T Cell Receptor Triggering*," Nature Reviews Immunology 11:47-55.

Verhoeyen, M. et al. (1988) "*Reshaping Human Antibodies: Grafting an Antilysozyme Activity*," Science 239:1534-1536.

Vigeral, P. et al. (1986) "*Prophylactic Use of OKT3 Monoclonal Antibody in Cadaver Kidney Recipients. Utilization of OKT3 as the Sole Immunosuppressive Agent*," Transplantation 41:730-733.

Weiss, A. (1993) "*T Cell Antigen Receptor Signal Transduction: A Tale of Tails and Cytoplasmic Protein-Tyrosine Kinases*," Cell 73:209-212.

Winter, G. et al. (1991) "*Man-made Antibodies*," Nature 349:293-299.

Winter, G. et al. (1994) "*Making Antibodies by Phage Display Technology*," Annu. Rev. Immunol. 12:433-455.

Wu, H. et al. (1998) "*Stepwise in vitro Affinity Maturation of Vitaxin, An $\alpha_v\beta_3$-Specific Humanized mAb*," Proc. Natl. Acad. Sci. (U.S.A.) 95:6037-6042.

Wucherpfennig, K.W. et al. (2010) "*Structural Biology of the T-cell Receptor: Insights into Receptor Assembly, Ligand Recognition, and Initiation of Signaling*," Cold Spring Harb. Perspect. Biol. 2(4):a005140 (14 pages).

Xiong et al. (2002) "*Efficient inhibition of human B-cell lymphoma xenografts with an anti-CD20 x anti-CD3 bispecific diabody*," Cancer Letters 177:29-39.

Xu, D. et al. (2000) "*In Vitro Characterization of Five Humanized OKT3 Effector Function Variant Antibodies*," Cell. Immunol. 200:16-26.

Yelton et al. (1995) "*Affinity Maturation of the BR96 Anti-Carcinoma Antibody by Codon-Based Mutagenesis*," J. Immunology 155:1994-2004.

Zang, X. et al. (2007) "The B7 Family and Cancer Therapy: Costimulation and Coinhibition," Clin. Cancer Res. 13:5271-5279.

Zhu et al. (1997) "*Remodeling domain interfaces to enhance heterodimer formation*," Protein Science 6:781-788.

Zuo et al. (2000) "*An efficient route to the production of an IgG-like bispecific antibody*," PE 13(5):361-367).

Li, B. et al. "Construction and Characterization of a Humanized Anti-Human CD3 Monoclonal Antibody 12F6 With Effective Immunoregulation Functions," Immunology 116(4):487-498 (2005).

\* cited by examiner

CD3-BINDING MOLECULES CAPABLE OF BINDING TO HUMAN AND NON-HUMAN CD3

CROSS-REFERENCE TO RELATED APPLICATIONS

This application is a continuation of U.S. application Ser. No. 16/168,559 (filed on Oct. 23, 2018), which application is a continuation of U.S. application Ser. No. 15/414,303 (filed on Jan. 24, 2017), which application is a divisional of U.S. application Ser. No. 14/118,523 (filed on Nov. 18, 2013), which application is a § 371 National Stage Application of PCT/US2012/038219 (filed on May 16, 2012), which application claims priority to U.S. Application Serial Nos. 61/488,716 (filed on May 21, 2011) and 61/530,353 (filed on Sep. 1, 2011), each of which applications is herein incorporated by reference in its entirety and to which priority is claimed.

REFERENCE TO SEQUENCE LISTING

This application includes one or more Sequence Listings pursuant to 37 C.F.R. 1.821 et seq., which are disclosed in computer-readable media (filed name: 1301_0075C_ST25, created Aug. 2, 2021, and having a size of 109942 bytes), which file is herein incorporated by reference in its entirety.

BACKGROUND OF THE INVENTION

Field of the Invention

The present invention relates to CD3-binding molecules capable of binding to human and non-human CD3, and in particular to such molecules that are cross-reactive with CD3 of a non-human mammal (e.g., a cynomolgus monkey). The invention also pertains to uses of such antibodies and antigen-binding fragments in the treatment of cancer, autoimmune and/or inflammatory diseases and other conditions.

Description of Related Art

The body's immune system serves as a defense against a variety of conditions, including, e.g., injury, infection and neoplasia, and is mediated by two separate but interrelated systems: the cellular and humoral immune systems. Generally speaking, the humoral system is mediated by soluble products (antibodies or immunoglobulins) that have the ability to combine with and neutralize products recognized by the system as being foreign to the body. In contrast, the cellular immune system involves the mobilization of certain cells, termed T cells, that serve a variety of therapeutic roles. T cells are lymphocytes that are derived from the thymus and circulate between the tissues, lymphatic system and the circulatory system. They act against, or in response to, a variety of foreign structures (antigens). In many instances these foreign antigens are expressed on host cells as a result of neoplasia or infection. Although T cells do not themselves secrete antibodies, they are usually required for antibody secretion by the second class of lymphocytes, B cells (which derive from bone marrow). Critically, T cells exhibit extraordinary immunological specificity so as to be capable of discerning one antigen from another).

A naive T cell, e.g., a T cell which has not yet encountered its specific antigen, is activated when it first encounters a specific peptide:MHC complex on an antigen presenting cell. The antigen presenting cell may be a B cell, a macrophage or a dendritic cell. When a naive T cell encounters a specific peptide:MHC complex on an antigen presenting cell, a signal is delivered through the T-cell receptor which induces a change in the conformation of the T cell's lymphocyte function associated antigen (LFA) molecules, and increases their affinity for intercellular adhesion molecules (ICAMs) present on the surface of the antigen presenting cell. The signal generated by the interaction of the T cell with an antigen presenting cell is necessary, but not sufficient, to activate a naive T cell. A second co-stimulatory signal is required. The naive T cell can be activated only by an antigen-presenting cell carrying both a specific peptide MHC complex and a co-stimulatory molecule on its surface. Antigen recognition by a naive T cell in the absence of co-stimulation results in the T cell becoming anergic. The need for two signals to activate T cells and B cells such that they achieve an adaptive immune response may provide a mechanism for avoiding responses to self-antigens that may be present on an antigen presenting cell at locations in the system where it can be recognized by a T cell. Where contact of a T cell with an antigen presenting cell results in the generation of only one of two required signals, the T cell does not become activated and an adaptive immune response does not occur.

The efficiency with which humans and other mammals develop an immunological response to pathogens and foreign substances rests on two characteristics: the exquisite specificity of the immune response for antigen recognition, and the immunological memory that allows for faster and more vigorous responses upon re-activation with the same antigen (Portoles, P. et al. (2009) "*The TCR/CD3 Complex: Opening the Gate to Successful Vaccination*," Current Pharmaceutical Design 15:3290-3300; Guy, C. S. et al. (2009) "*Organization of Proximal Signal Initiation at the TCR:CD3 Complex*," Immunol Rev. 232(1):7-21). The specificity of the response of T-cells is mediated by the recognition of antigen (displayed on Antigen-Presenting Cells (APCs) by a molecular complex involving the T Cell Receptor ("TCR") and the cell surface receptor ligand, CD3. The TCR is a covalently linked heterodimer of α and β chains ("TCRαβ"). These chains are class I membrane polypeptides of 259 (α) and 296 (β) amino acids in length. The CD3 molecule is a complex containing a CD3 γ chain, a CD3 δ chain, and two CD3 ε chains associated as three dimers (εγ, εδ, ζζ) (Guy, C. S. et al. (2009) "*Organization of Proximal Signal Initiation at the TCR:CD3 Complex*," Immunol Rev. 232(1):7-21; Call, M. E. et al. (2007) "*Common Themes In The Assembly And Architecture Of Activating Immune Receptors*," Nat. Rev. Immunol. 7:841-850; Weiss, A. (1993) "*T Cell Antigen Receptor Signal Transduction: A Tale Of Tails And Cytoplasmic Protein-Tyrosine Kinases*," Cell 73:209-212). The TCR and CD3 complex, along with the CD3 ζ chain zeta chain (also known as T-cell receptor T3 zeta chain or CD247) comprise the TCR complex (van der Merwe, P. A. etc. (epub Dec. 3, 2010) "*Mechanisms For T Cell Receptor Triggering*," Nat. Rev. Immunol. 11:47-55; Wucherpfennig, K. W. et al. (2010) "*Structural Biology of the T-cell Receptor: Insights into Receptor Assembly, Ligand Recognition, and Initiation of Signaling*," Cold Spring Harb. Perspect. Biol. 2:a005140). The complex is particularly significant since it contains a large number (ten) of immunoreceptor tyrosine-based activation motifs (ITAMs).

In mature T cells, TCR/CD3 activation by foreign antigenic peptides associated to self-MHC molecules is the first step needed for the expansion of antigen-specific T cells, and their differentiation into effector or memory T lymphocytes.

These processes involve the phosphorylation of the immunoreceptor tyrosine-based activation motifs (ITAMs) of the TCR complex. Because the TCR complex has such a large number of ITAMS (10 in all), and these ITAMS are arrayed in tandem (due to the dimerization of the constituent chains), phosphorylation of the relevant tyrosine residues upon TCR ligation creates paired docking sites for proteins that contain Src homology 2 (SH2) domains such as the (chain-associated protein of 70 kDa (ZAP-70), and thereby initiate an amplifying signaling cascade which leads to T-cell activation and differentiation (Guy, C. S. et al. (2009) "*Organization of Proximal Signal Initiation at the TCR:CD3 Complex*," Immunol Rev. 232(1):7-21).

The outcome of these processes is modulated by the intensity and quality of the antigen stimulus, as well as by the nature of accompanying signals delivered by co-receptor and co-stimulatory surface molecules, or by cytokine receptors (Portoles, P. et al. (2009) "*The TCR/CD3 Complex: Opening the Gate to Successful Vaccination*," Current Pharmaceutical Design 15:3290-3300; Riha, P. et al. (2010) "*CD28 Co-Signaling In The Adaptive Immune Response*," Self/Nonself 1(3):231-240). Although TCR stimulation is a prerequisite for T-cell activation, it is well recognized that engagement of co-stimulatory molecules, such as CD28, is necessary for full T-cell activation and differentiation (Guy, C. S. et al. (2009) "*Organization of Proximal Signal Initiation at the TCR:CD3 Complex*," Immunol Rev. 232(1):7-21).

Due to the fundamental nature of CD3 in initiating an anti-antigen response, monoclonal antibodies against this receptor have been proposed as being capable of blocking or at least modulating the immune process and thus as agents for the treatment of inflammatory and/or autoimmune disease. Indeed, anti-CD3 antibodies were the first antibody approved for the human therapy (St. Clair E. W. (2009) "*Novel Targeted Therapies for Autoimmunity*," Curr. Opin. Immunol. 21(6):648-657). Anti-CD3 antibody (marketed as ORTHOCLONE™ OKT3™ by Janssen-Cilag) has been administered to reduce acute rejection in patients with organ transplants and as a treatment for lymphoblastic leukemia (Cosimi, A. B. et al. (1981) "*Use Of Monoclonal Antibodies To T-Cell Subsets For Immunologic Monitoring And Treatment In Recipients Of Renal Allografts*," N. Engl. J. Med. 305:308-314; Kung, P. et al. (1979) Monoclonal antibodies defining distinctive human T cell surface antigens," Science 206:347-349; Vigeral, P. et al. (1986) "*Prophylactic Use Of OKT3 Monoclonal Antibody In Cadaver Kidney Recipients. Utilization Of OKT3 As The Sole Immunosuppressive Agent*," Transplantation 41:730-733; Midtvedt, K. et al. (2003) "*Individualized T Cell Monitored Administration Of ATG Versus OKT3 In Steroid-Resistant Kidney Graft Rejection*," Clin. Transplant. 17(1):69-74; Gramatzki, M. et al. (1995) "*Therapy With OKT3 Monoclonal Antibody In Refractory T Cell Acute Lymphoblastic Leukemia Induces Interleukin-2 Responsiveness*," Leukemia 9(3):382-390; Herold, K. C. et al. (2002) "*Anti-CD3 Monoclonal Antibody In New-Onset Type 1 Diabetes Mellitus*," N. Engl. J. Med. 346:1692-1698; Cole, M. S. et al. (1997) "*Human IgG2 Variants Of Chimeric Anti-CD3 Are Nonmitogenic to T cells*," J. Immunol. 159(7):3613-3621; Cole, M. S. et al. (1999) "*Hum291, A Humanized Anti-CD3 Antibody, Is Immunosuppressive To T Cells While Exhibiting Reduced Mitogenicity in vitro*," Transplantation 68:563-571; U.S. Pat. Nos. 6,491,916; 5,585,097 and 6,706,265).

However, such anti-CD3 treatment has not proven to be specific enough to avoid side effects (Ludvigsson, J. (2009) "*The Role of Immunomodulation Therapy in Autoimmune Diabetes*," J. Diabetes Sci. Technol. 3(2):320-330). Repeated daily administration of OKT3 results in profound immunosuppression and provides effective treatment of rejection following renal transplantation. The in vivo administration of OKT3 results in both T cell activation and suppression of immune responses. However, the use of OKT3 has been hampered by a first toxic dose reaction syndrome that is related to initial T-cell activation events and to the ensuing release of cytokines that occurs before immunosuppression of T cell responses. The reported side effects that follow the first and sometimes the second injection of this mouse monoclonal antibody include a "flu-like" syndrome consisting of high fever, chills, headache, and gastrointestinal symptoms (vomiting and diarrhea) and in severe cases pulmonary edema within hours of treatment has been noted (Thistlethwaite, J. R. Jr. et al. (1988) "*Complications and Monitoring of OKT3 Therapy*," Am. J. Kidney Dis. 11:112-119). This syndrome is believed to reflect OKT3-mediated cross-linking of the TCR/CD3 complex on the T cell surface and the resultant release of cytokines (e.g., tumor necrosis factor alpha (TNFα), interferon-γ, interleukins IL-2, IL-3, IL-4, IL-6, IL-10 and granulocyte-macrophage colony-stimulating factor (Masharani, U. B. et al. (2010) "*Teplizumab Therapy For Type 1 Diabetes*," Expert Opin. Biol. Ther. 10(3):459-465; Abramowicz, D. et al. (1989) "*Release Of Tumor Necrosis Factor, Interleukin-2, And Gamma-Interferon In Serum After Injection Of OKT3 Monoclonal Antibody In Kidney Transplant Recipients*," Transplantation 47:606-608; Ferran, C. et al. (1990) "*Cytokine-Related Syndrome Following Injection Of Anti-CD3 Monoclonal Antibody: Further Evidence For Transient In Vivo T Cell Activation*," Eur. J. Immunol. 20:509-515; Hirsch, R. et al. (12989) "*Effects Of In Vivo Administration Of Anti-CD3 Monoclonal Antibody On T Cell Function In Mice. II In Vivo Activation Of T Cells*," J. Immunol. 142:737-743). The use of anti-CD3 antibodies is disclosed in U.S. Pat. Nos. 7,883,703; 7,728,114; 7,635,472; 7,575,923; and 7,381,903, and in United States Patent Publications Nos. 2010/0150918; 2010/0209437; 2010/0183554; 2010/0015142, 2008/0095766, 2007/0077246 and in PCT Publication WO2008/119567.

A particular limitation of prior antibodies is their specificity for only human CD3. This limitation is a significant impediment to the development of such antibodies as therapeutic agents for the treatment of human diseases. In order to obtain market approval any new candidate medication must pass through rigorous testing. This testing can be subdivided into preclinical and clinical phases. Whereas the latter—further subdivided into the generally known clinical phases I, II and III—is performed in human patients, the former is performed in animals. The aim of pre-clinical testing is to prove that the drug candidate has the desired activity and most importantly is safe. Only when the safety in animals and possible effectiveness of the drug candidate has been established in preclinical testing this drug candidate will be approved for clinical testing in humans by the respective regulatory authority. Drug candidates can be tested for safety in animals in the following three ways, (i) in a relevant species, i.e., in a species where the drug candidates can recognize the ortholog antigens, (ii) in a transgenic animal containing the human antigens and (iii) by use of a surrogate for the drug candidate that can bind the ortholog antigens present in the animal. Limitations of transgenic animals are that this technology is typically limited to rodents. However, rodents and humans have significant differences in physiology that may complicate the extrapolation of safety data obtained in rodents to predict safety in humans. The limitations of a surrogate for the drug candidate are the different composition of matter compared to the actual drug candidate and often the animals used are rodents with the limitation as discussed above. Therefore, preclinical data generated in rodents are of limited predictive power with respect to the drug candidate. The approach of choice for safety testing is the use of a relevant species, preferably a lower primate. The limitation now of the CD3 binding molecules suitable for therapeutic intervention in man described in the art is that the relevant species are higher primates, in particular cynomolgus monkeys. Accordingly, an anti-CD3 antibody capable of binding to both human and primate CD3 is highly desirable. Such antibodies have been described in United States Patent Publication No. 20100150918 and in PCT Publication WO2008/119567.

Despite such advances, a need remains for anti-human CD3 antibodies and their antigen-binding fragments that are capable of cross-reacting with CD3 of a non-human mammal (e.g., a cynomolgous monkey). The present invention addresses this need and the need for improved therapeutics for cancer, autoimmunity and inflammatory diseases.

SUMMARY OF THE INVENTION

The present invention relates to CD3-binding molecules capable of binding to human and non-human CD3, and in particular to such molecules that are cross-reactive with CD3 of a non-human mammal (e.g., a cynomolgus monkey). The invention also pertains to uses of such antibodies and antigen-binding fragments in the treatment of cancer, autoimmune and/or inflammatory diseases and other conditions.

In detail, the invention provides a CD3-binding molecule comprising an antigen-binding fragment of an antibody, wherein the antigen-binding fragment comprises an antibody CD3-specific VL domain and an antibody CD3-specific VH domain, wherein the CD3-specific VL domain and the CD3-specific VH domain form an antigen-binding domain capable of immunospecifically binding to both an epitope of human CD3 and to an epitope of the CD3 of a non-human mammal, wherein:
(I) the CD3-specific VL domain is selected from the group consisting of h-mab2 VL-1 (SEQ ID NO:16), h-mab2 VL-2 (SEQ ID NO:18), h-mab2 VL-3 (SEQ ID NO:20), h-mab2 VL-4 (SEQ ID NO:22), h-mab2 VL-5 (SEQ ID NO:24), h-mab2 VL-6 (SEQ ID NO:26), h-mab2 VL-7 (SEQ ID NO:28), h-mab2 VL-8 (SEQ ID NO:30), h-mab2 VL-9 (SEQ ID NO:32), and h-mab2 VL-10 (SEQ ID NO:34), and said CD3-specific VH domain is selected from the group consisting of h-mab2 VH-1 (SEQ ID NO:36), h-mab2 VH-2 (SEQ ID NO:38), h-mab2 VH-3 (SEQ ID NO:40), h-mab2 VH-4 (SEQ ID NO:42), h-mab2 VH-5 (SEQ ID NO:44), h-mab2 VH-6 (SEQ ID NO:46), h-mab2 VH-6L (SEQ ID NO:54), h-mab2 VH-7 (SEQ ID NO:48), h-mab2 VH-8 (SEQ ID NO:50), h-mab2 VH-8L (SEQ ID NO:55), h-mab2 VH-8 di-1 (SEQ ID NO:56), h-mab2 VH-8 di-2 (SEQ ID NO:57), h-mab2 VH-6M (SEQ ID NO:72), h-mab2 VH-8M (SEQ ID NO:74), h-mab2 VH-2k (SEQ ID NO:87), and h-mab2 VH-5k (SEQ ID NO:88); or
(II) the CD3-specific VL domain is selected from the group consisting of h-mab1 VL-1 (SEQ ID NO:10) and h-mab1 VL-2 (SEQ ID NO:12), and the CD3-specific VH domain is h-mab1 VH (SEQ ID NO:14).

The invention particularly concerns the embodiment of the above-described CD3-binding molecule wherein the CD3-specific VL domain is h-mab2 VL-6 (SEQ ID NO:26).

The invention further concerns the embodiment of the above-described CD3-binding molecules wherein the CD3-specific VH domain is h-mab2 VH-8 (SEQ ID NO:50), h-mab2 VH-6 (SEQ ID NO:46), or h-mab2 VH-2k (SEQ ID NO:87).

The invention particularly concerns the embodiment of the above-described CD3-binding molecule wherein the molecule is an antibody, and particularly, wherein the antibody lacks an Fc region or comprises an Fc region that:
(A) lacks effector function or has reduced effector function; or
(B) impairs the ability of the Fc region of the antibody to bind to an Fc receptor; wherein the reduction in effector function and the impairment of binding ability is relative to that of a wild-type Fc receptor.

The invention further concerns the embodiment of the above-described CD3-binding molecules wherein the molecule is a CD3-binding diabody that comprises a first polypeptide chain and a second polypeptide chain, the chains being covalently bonded to one another, wherein:
I. the first polypeptide chain comprises an amino terminus and a carboxy terminus and from N-terminus to C-terminus:
(i) a domain (A) comprising the CD3-specific VL domain;
(ii) a domain (B) comprising a binding region of a heavy chain variable domain of a second immunoglobulin (VH2); and
(iii) a domain (C);
wherein the domains (A) and (B) do not associate with one another to form an epitope binding site;
and
(II) the second polypeptide chain comprises an amino terminus and a carboxy terminus and from N-terminus to C-terminus:
(i) a domain (D) comprising a binding region of a light chain variable domain of the second immunoglobulin (VL2);
(ii) a domain (E) comprising the CD3-specific VH domain; and
(iii) a domain (F);
wherein the domains (D) and (E) do not associate with one another to form an epitope binding site; and
wherein:
(1) the domains (A) and (E) associate to form the antigen-binding domain that is capable of immunospecifically binding to both human CD3 and to the CD3 of a non-human mammal;
(2) the domains (B) and (D) associate to form a binding site that immunospecifically binds to a second epitope, the second epitope being different from the CD3 epitope bound by the antigen-binding domain formed from the association of the domains (A) and (E); and
(3) the domains (C) and (F) are covalently associated together.

The invention further concerns the embodiment of the above-described CD3-binding molecules wherein the second epitope is not an epitope of CD3.

The invention further concerns the embodiment of the above-described CD3-binding molecules wherein the second epitope is an epitope of CD3 that is different from the CD3 epitope bound by the antigen-binding domain formed from the association of the domains (A) and (E).

The invention further concerns the embodiment of the above-described CD3-binding molecules or antibodies or diabodies in which such molecule humanized.

The invention further concerns the embodiment of the above-described CD3-binding molecules or antibodies or diabodies in which such molecule is capable of immunospecifically binding to CD3 and to fluorescein.

The invention further concerns the embodiment of the above-described CD3-binding molecules or diabodies in which such molecule is capable of immunospecifically binding to both: (i) CD3 and (ii)(a) a tumor antigen, or (ii)(b) a cell surface antigen, receptor or receptor ligand.

The invention further concerns the embodiment of the above-described CD3-binding molecules or diabodies in which the molecule or diabody is capable of immunospecifically binding to CD3 and to a tumor antigen expressed on a tumor cell, wherein the tumor cell is a tumor cell from a cancer selected from the group consisting of: breast cancer, prostate cancer, gastric cancer, lung cancer, stomach cancer, colon cancer, rectal cancer, pancreatic cancer, liver cancer, ovarian cancer, oral cavity cancer, pharyngeal cancer, esophageal cancer, laryngeal cancer, bone cancer, skin cancer, melanoma, uterine cancer, testicular cancer, bladder cancer, kidney cancer, brain cancer, glioblastoma, thyroid cancer, lymphoma, myeloma, and leukemia.

The invention further concerns the embodiment of the above-described CD3-binding molecules or diabodies in which the molecule or diabody is capable of immunospecifically binding to CD3 and to a cell surface antigen, receptor or receptor ligand, wherein the cell surface antigen, receptor or receptor ligand is HER2/neu, B7-H3, CD20, PSMA, IGF-1R., Ep-CAM, or is a molecule involved in a T cell—B cell association that leads to T cell or B cell activation in an adaptive immune response.

The invention further concerns the embodiment of the above-described CD3-binding molecules or diabodies in which the molecule or diabody is capable of immunospecifically binding to CD3 and to a molecule involved in the T cell—B cell association and the molecule involved in the T cell—B cell association is selected from the group consisting of CD19, CD20, CD22, CD23, CD27, CD32B, CD38, CD40, CD79a, CD79b, CD80, CD86, LFA-I, LFA-3 and CFA-I.

The invention further concerns a pharmaceutical composition comprising any of the above-described CD3-binding molecules, antibodies or diabodies, and a pharmaceutically acceptable carrier, excipient or diluent.

The invention further concerns the above-described pharmaceutical composition for use in the treatment of cancer or an autoimmune or inflammatory disease.

The invention further concerns the above-described pharmaceutical composition for use in the treatment of an autoimmune or inflammatory disease selected from the group consisting of: type I insulin-dependent diabetes, rheumatoid arthritis, systemic lupus erythematosus, multiple sclerosis, inflammatory bowel disease, myasthenia gravis, celiac's disease, Sjogren's syndrome, Grave's disease, Crohn's disease, autoimmune hepatitis, psoriasis, psoriatic arthritis, asthma, allergic rhinitis, effects from organ transplantation, or graft vs. host disease (GVHD). The invention particularly concerns the above-described pharmaceutical composition for use in the treatment of type I insulin-dependent diabetes.

BRIEF DESCRIPTION OF THE DRAWINGS

FIG. 13A: redirected killing of Raji human B-cell lymphoma cells; FIG. 13B: redirected killing of JeKo-1 human mantle cell lymphoma cells

DETAILED DESCRIPTION OF THE INVENTION

Figure 1A:
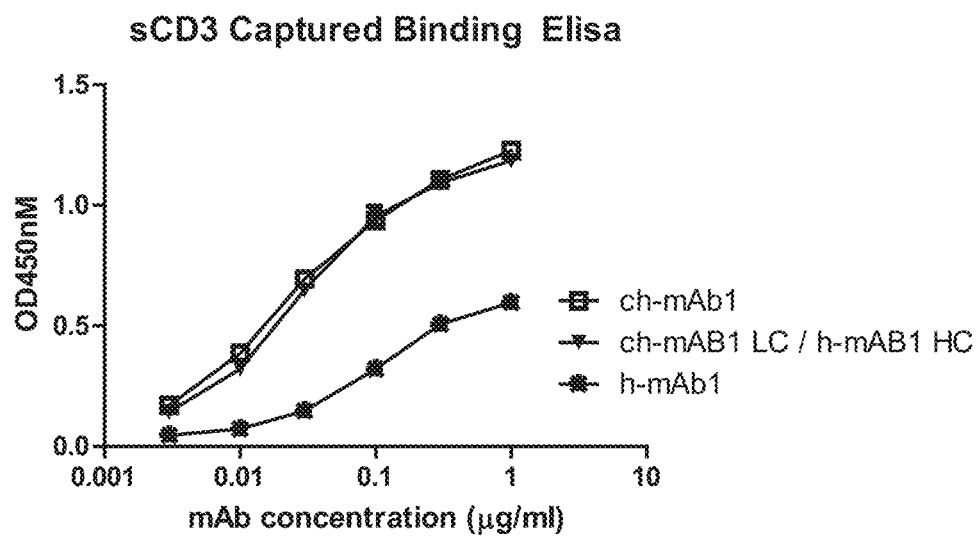
FIGS. 1A-1B show the results of a capture ELISA in which the ability of anti-CD3 antibody mAB1 (FIG. 1A) or a chimeric derivative of antibody mAB1 (ch-mAb1) (FIG. 1B) was assessed using human soluble CD3 ("shCD3").

The present invention relates to anti-human CD3 antibodies and their antigen-binding fragments, and in particular to such antibodies that are cross-reactive with CD3 of a non-human mammal (e.g., a cynomolgous monkey). The invention also pertains to uses of such antibodies and antigen-binding fragments in the treatment of cancer, autoimmune and/or inflammatory diseases and other conditions.

I. Definitions

As used herein, the term "CD3-binding molecule" denotes a molecule capable of immunospecific binding to both human CD3 and to the CD3 of a non-human mammal through at least one antigen recognition site (e.g., an antigen-binding domain of an antibody) located in the variable region of the molecule. As used herein such capability to immunospecifically bind to both human CD3 and to the CD3 of a non-human mammal is not intended to denote a capacity of a single antigen binding domain to simultaneously bind to both such CD3 molecules, but rather that such an antigen-binding domain exhibits cross-reactivity such that it will immunospecifically bind to human CD3 when incubated in the presence of human CD3 and will immunospecifically bind to the CD3 of a non-human mammal when incubated in the presence of such non-human mammalian CD3.

As used herein, the term "CD3-binding molecule" encompasses not only intact polyclonal or monoclonal antibodies, but also fragments thereof (such as Fab, Fab', F(ab')$_2$ Fv), single chain (ScFv), mutants thereof, naturally occurring variants, fusion proteins comprising an antibody portion with an antigen recognition site of the required specificity, humanized antibodies, chimeric antibodies, "BiTEs®," "DART™" diabody molecules and any other modified configuration of the immunoglobulin molecule that comprises an antigen recognition site of the required specificity. The term "BiTEs" (bi-specific T-cell engagers) refers to a single polypeptide chain molecule that having two antigen-binding domains, one of which binds to a T-cell antigen and the second of which binds to an antigen present on the surface of a target (WO 05/061547; Baeuerle, P et al. (2008) "*BiTE®: A New Class Of Antibodies That Recruit T Cells*," Drugs of the Future 33: 137-147; Bargou, et al. 2008) "*Tumor Regression in Cancer Patients by Very Low Doses of a T Cell-Engaging Antibody*," Science 321: 974-977).

The term "DART™" (Dual Affinity ReTargeting reagent) diabody refers to an immunoglobulin molecule that comprises at least two polypeptide chains that associate (especially through a covalent interaction) to form at least two epitope binding sites, which may recognize the same or different epitopes. Each of the polypeptide chains of a DART™ diabody comprise an immunoglobulin light chain variable region and an immunoglobulin heavy chain variable region, but these regions do not interact to form an epitope binding site. Rather, the immunoglobulin heavy chain variable region of one (e.g., the first) of the DART™ diabody polypeptide chains interacts with the immunoglobulin light chain variable region of a different (e.g., the second) DART™ polypeptide chain to form an epitope binding site. Similarly, the immunoglobulin light chain variable region of one (e.g., the first) of the DART™ diabody polypeptide chains interacts with the immunoglobulin heavy chain variable region of a different (e.g., the second) DART™ diabody polypeptide chain to form an epitope binding site. DART™ diabodies may be monospecific, bispecific, trispecific, etc., thus being able to simultaneously bind one, two, three or more different epitopes (which may be of the same or of different antigens). DART™ diabodies may additionally be monovalent, bivalent, trivalent, tetravalent, pentavalent, hexavelent, etc., thus being able to simultaneously bind one, two, three, four, five, six or more molecules. These two attributes of DART™ diabodies (i.e., degree of specificity and valency may be combined, for example to produce bispecific antibodies (i.e., capable of binding two epitopes) that are tetravalent (i.e., capable of binding four sets of epitopes), etc. DART™ diabody molecules are disclosed in PCT Publications WO 2006/113665, WO 2008/157379, and WO 2010/080538.

The bispecific (or trispecific or multispecific) molecules of the present invention will be capable of binding to both human CD3 and the CD3 of a non-human mammal (e.g., cynomolgous monkey), and also to a second (or additional) and different antigen(s) or epitope(s). The second antigen or epitope is preferably a tumor antigen expressed on a tumor cell. Such tumor cells may be from cancers, for example, breast cancer, prostate cancer, gastric cancer, lung cancer, stomach cancer, colon cancer, rectal cancer, pancreatic cancer, liver cancer, ovarian cancer, oral cavity cancer, pharyngeal cancer, esophageal cancer, laryngeal cancer, bone cancer, skin cancer, melanoma, uterine cancer, testicular cancer, bladder cancer, kidney cancer, brain cancer, glioblastoma, thyroid cancer, lymphoma, myeloma, or leukemia. The additional antigens or epitopes are preferably cell surface tumor antigens or epitopes (such as: 17-1A, A33, adult erythrocyte primary endoderm I antigen, alpha fetoprotein, an envelope antigen of an RNA tumor virus, bladder tumor oncofetal antigen, B7-H1, B7-H2, B7-H3, B7-H4, B7-H5, B7-H6, Burkitt's lymphoma antigen-38.13, CA125, CD18, CD19, human B-lymphoma antigen-CD20, CD22, CD33, CD44, CD52, CEA, C017-1A, CTA-1, CTLA-4, epidermal growth factor receptor, Ep-CAM, EphA2, fetal erythrocyte I antigen, fibrosarcoma antigen, ganglioside GD2, ganglioside GD3, ganglioside GM2, ganglioside GM3, GICA 19-9, gp IIIb/IIIa, gp72, HER1, HER-2/neu, HER3, HER4, high molecular weight melanoma antigen, HLA-DR antigen, human leukemia T cell antigen-Gp37, human lung carcinoma antigen L20, human lung carcinoma antigen L6, human milk fat globule antigen, IgE, KS ¼ pan-carcinoma antigen, LEA, lung adenocarcinoma F3 antigen, malignant human lymphocyte antigen-APO-1, melanoma antigen gp75, melanoma-associated antigen p97, neoglycoprotein, nuC242, polymorphic epithelial mucin antigen, prostate specific antigen, prostate specific membrane antigen, prostatic acid phosphate, SK-1 antigen, TAG-72, T-antigen, tumor antigen CA125, tumor antigen MUC1, tumor-specific transplantation type of cell-surface antigen, vascular endothelial growth factor, vascular endothelial growth factor-receptor, and αvβ3). Alternatively, such additional antigens or epitopes may be associated with a pathogen (such as: hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), viral miningitis, viral encephalitis, dengue, small pox; mycobacteria *rickettsia, mycoplasma, neisseria, S. pneumonia, Borrelia burgdorferi, Bacillus anthracis, Streptococcus, Staphylococcus, Mycobacterium*, tetanus, pertissus, cholera, plague, diptheria, *chlamydia*, and *legionella; leishmania*, kokzidioa, *trypanosoma* or malaria; *chlamydia* and *rickettsia*.

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')2 Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody."

The term "humanized antibody" refer to a chimeric molecule, generally prepared using recombinant techniques, having an antigen binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions. This eliminates the constant region as an immunogen in human individuals, but the possibility of an immune response to the foreign variable region remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide scaffolding for the CDRs. When nonhuman antibodies are prepared with respect to a particular antigen, the variable regions can be "reshaped" or "humanized" by grafting CDRs derived from nonhuman antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154.

In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody. As disclosed below, the preferred antibodies of the present invention have specific identified CDRs. The present invention, however, contemplates equivalent antibodies having altered CDRs.

As used herein, an antibody or a polypeptide is said to "immunospecifically" or equivalently, "specifically" bind a region of another molecule (i.e., an epitope) if it reacts or associates more frequently, more rapidly, with greater duration and/or with greater affinity with that epitope relative to alternative epitopes. For example, an antibody that specifically binds to a CD3 epitope is an antibody that binds this CD3 epitope with greater affinity, avidity, more readily, and/or with greater duration than it binds to other CD3 epitopes or non-CD3 epitopes. It is also understood by reading this definition that, for example, an antibody (or moiety or epitope) that immunospecifically binds to a first target may or may not specifically or preferentially bind to a second target. As such, "immunospecific binding" does not necessarily require (although it can include) "exclusive" binding. Generally, but not necessarily, reference to binding means "immunospecific" binding.

As used herein, the term "immunologically active" in reference to an epitope being or "remaining immunologically active" refers to the capability of an antibody (e.g., an anti-CD3 antibody) to bind to the epitope under different conditions, for example, after the epitope has been subjected to reducing and denaturing conditions. For example, if the antibody is no longer able to bind a denatured epitope, that epitope is said to have been rendered immunologically inactive.

Different biological functions are associated with the anti-CD3 antibodies of the present invention, and such antibodies may exhibit any or all of the following attributes, or may lack, one, two, three or more such attributes: an ability to specifically bind human CD3 as endogenously expressed on the surface of a normal human T cell; an ability to specifically bind human CD3 as endogenously expressed on the surface of a human leukemic T cell; an ability to specifically bind non-human mammal (e.g., cynomolgus monkey) CD3 as endogenously expressed on the surface of a normal non-human mammal T cell; an ability to specifically bind non-human CD3 as endogenously expressed on the surface of a normal non-human T cell; an ability to specifically bind a non-human CD3 as endogenously expressed on the surface of a non-human leukemic T cell; an ability to neutralize (i.e., block or interfere with binding) the formation of the CD3 complex; an ability to neutralize the formation of the TCR complex; an ability to modulate (either antagonistically or agonistically) signaling by the TCR complex; an ability to bind the Fc receptor; an ability to competitively inhibit preferential binding of a known anti-CD3 antibody to CD3, including the ability to preferentially bind to the same CD3 epitope to which the original antibody preferentially binds; an ability to bind to a portion of CD3 that is exposed on the surface of a living cell in vitro or in vivo; an ability to bind to a portion of CD3 that is exposed on the surface of a living cancer cell; an ability to deliver a chemotherapeutic agent into a cancerous T cell; and/or an ability to deliver a therapeutic agent, toxin or detectable marker into a T cell. As discussed herein, polypeptides (including antibodies) of the invention may have any one or more of these characteristics.

As used herein, the term "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. Agents that are employed in the methods of this invention can be randomly selected or rationally selected or designed. As used herein, an agent is said to be randomly selected when the agent is chosen without prior consideration or knowledge of the specific amino acid or other chemical moieties involved in the association of the molecule with its native binding partner(s) or known antibodies. An example of a randomly selected agent is an agent that is identified through the use and screening of a chemical library or a peptide combinatorial library. As used herein, an agent is said to be rationally selected or designed when the agent is chosen on a non-random basis that takes into account the sequence of the target site and/or its conformation in connection with the agent's action. Agents can be rationally selected or rationally designed by utilizing the peptide sequences that make up the contact sites of the receptor/ligand and/or CD3/anti-CD3 antibody complex. For example, a rationally selected peptide agent can be a peptide whose amino acid sequence is identical to an epitope appearing on CD3 as it is exposed on the surface of a living cell in its native environment. Such an agent will reduce or block the association of the anti-CD3 antibody with CD3, or the association of CD3 with its native ligand, as desired, by binding to the anti-CD3 antibody or to the native ligand.

As used herein, the term "labeled," with regard to an antibody, is intended to encompass direct labeling of the antibody by coupling (i.e., physically linking) a detectable substance, such as a radioactive agent or a fluorophore (e.g. phycoerythrin (PE) or fluorescein isothiocyanate (also known as fluoroisothiocyanate or FITC)) to the antibody, as well as indirect labeling of the probe or antibody by reactivity with a detectable substance.

As used herein, the term "association," with regard to an antibody, includes covalent and non-covalent attachment or binding of an agent (e.g., chemotherapeutic agent) to the antibody. The antibody can be associated with an agent (e.g., chemotherapeutic agent) by direct binding or indirect binding via attachment to a common platform, such that the antibody directs the localization of the agent to the cancerous cell to which the antibody binds and wherein the antibody and agent do not substantially dissociate under physiological conditions such that the agent is not targeted to the same cancerous cell to which the antibody binds or such that the agent's potency is not decreased.

The term "biological sample" encompasses a variety of sample types obtained from an individual and can be used in a diagnostic or monitoring assay. The definition encompasses saliva, blood and other liquid samples of biological origin, solid tissue samples such as a biopsy specimen or tissue cultures or cells derived therefrom, and the progeny thereof, for example, cells obtained from a tissue sample collected from an individual suspected of having cancer, in preferred embodiments from ovary, lung, prostate, pancreas, colon, and breast tissue. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

The term "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, an "effective amount" of a pharmaceutical composition, in one embodiment, is an amount sufficient to effect beneficial or desired results including, without limitation, clinical results such as shrinking the size or rate of growth of a tumor, delaying or attenuating an inflammatory reaction, increasing the quality of life of those suffering from a disease, decreasing the dose of other medications required to treat such disease, enhancing the effect of another medication such as via targeting and/or internalization, delaying the progression of the disease, and/or prolonging survival of individuals. Such effective amount can be administered in one or more administrations. For purposes of this invention, an effective amount of drug, compound, or pharmaceutical composition is an amount sufficient to ameliorate a clinical observable condition.

In some embodiments, an effective amount of a drug, compound, or pharmaceutical composition may or may not be achieved in conjunction with another drug, compound, or pharmaceutical composition. Thus, an "effective amount" may be considered in the context of administering one or more additional agents, and a single agent may be considered to be given in an effective amount if, in conjunction with one or more other agents, a desirable result may be or is achieved. While individual needs vary, determination of optimal ranges of effective amounts of each component is within the skill of the art. Typical dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage and frequency of administration of molecules of the invention may be reduced or altered by enhancing uptake and tissue penetration of the molecules of the invention by modifications such as, for example, lipidation.

As used herein, a nucleic acid molecule or agent, antibody, composition or cell, etc., is said to be "isolated" when that nucleic acid molecule, agent, antibody, composition, or cell, etc. is substantially separated from contaminant nucleic acid molecules, antibodies, agents, compositions, or cells, etc. naturally present in its original source.

The term "individual" refers to a vertebrate animal, preferably a mammal. Mammals include, but are not limited to, humans, farm animals, sport animals, pets, primates, mice and rats. In the most preferred embodiment, the term individual denotes a human.

The terms "polypeptide," "oligopeptide," "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or as associated chains.

As used herein, the term "substantially pure" refers to material that is at least 50% pure (i.e., free from contaminants), more preferably at least 90% pure, more preferably at least 95% pure, more preferably at least 98% pure, more preferably at least 99% pure, and most preferably greater than 99% pure.

As used herein, the term "toxin" refers to any substance which effects an adverse response within a cell. For example, a toxin directed to a cancerous cell would have an adverse, sometimes deleterious effect, on the cancerous cell. Examples of toxins include, but are not limited to, a taxane, a maytansinoid, an auristatin (e.g., monomethyl auristatin (MMAE), monomethyl auristatin F (MMAF), auristatin E (AE), etc.) (such as those disclosed in U.S. Pat. Nos. 5,208,020; 5,416,064; 6,333,410; 6,340,701; 6,372,738; 6,436,931; 6,441,163; 6,596,757; 7,276,497; 7,585,857; or 7,851,432), a calicheamicin, an anthracycline (e.g., doxorubicin), a CC-1065 analog, docetaxel; cathepsin B or E; ricin, gelonin, *Pseudomonas* exotoxin, diphtheria toxin, and RNase; radiolabeled antibodies (e.g., tiuxetan-conjugated or labeled with a toxic radioisotope (for example, $^{90}$Y; $^{131}$I, $^{177}$Lu, $^{186}$Re, $^{188}$Re, $^{211}$At, $^{212}$Bi, $^{213}$Bi $^{22}$Ac, etc.).

As used herein, the terms "treatment" or "treating" denote an approach for obtaining a beneficial or desired result including and preferably a beneficial or desired clinical result. Such beneficial or desired clinical results include, but are not limited to, one or more of the following: reducing inflammation or an autoimmune response, reducing the proliferation of (or destroying) cancerous cells or other diseased cells, reducing metastasis of cancerous cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of individuals.

II. Methods of Making the Antibodies And Polypeptides of the Present Invention Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in non-human species, such as mice. In general, a mouse or rat is used for immunization but other animals may also be used. The antibodies are produced by immunizing mice with an immunogenic amount of cells, cell extracts, or protein preparations that contain human CD3. The immunogen can be, but is not limited to, primary cells, cultured cell lines, cancerous cells, nucleic acids, or tissue.

In one embodiment, monoclonal antibodies that bind to CD3 are obtained by using host cells that over-express CD3 as an immunogen. Such cells include, by way of example and not by limitation, human T cells.

To monitor the antibody response, a small biological sample (e.g., blood) may be obtained from the animal and tested for antibody titer against the immunogen. The spleen and/or several large lymph nodes can be removed and dissociated into single cells. If desired, the spleen cells may be screened (after removal of non-specifically adherent cells) by applying a cell suspension to a plate or to a well coated with the antigen. B-cells, expressing membrane-bound immunoglobulin specific for the antigen, will bind to the plate, and are not rinsed away with the rest of the suspension. Resulting B-cells, or all dissociated spleen cells, can then be fused with myeloma cells (e.g., X63-Ag8.653 and those from the Salk Institute, Cell Distribution Center, San Diego, CA). Polyethylene glycol (PEG) may be used to fuse spleen or lymphocytes with myeloma cells to form a hybridoma. The hybridoma is then cultured in a selective medium (e.g., hypoxanthine, aminopterin, thymidine medium, otherwise known as "HAT medium"). The resulting hybridomas are then plated by limiting dilution, and are assayed for the production of antibodies that bind specifically to the immunogen, using, for example, FACS (fluorescence activated cell sorting) or immunohistochemistry (IHC) screening. The selected monoclonal antibody-secreting hybridomas are then cultured either in vitro (e.g., in tissue culture bottles or hollow fiber reactors), or in vivo (e.g., as ascites in mice).

As another alternative to the cell fusion technique, Epstein-Barr Virus (EBV)-immortalized B cells may be used to produce monoclonal antibodies of the subject invention. The hybridomas are expanded and subcloned, if desired, and supernatants are assayed for anti-immunogen activity by conventional assay procedures (e.g., FACS, IHC, radioimmunoassay, enzyme immunoassay, fluorescence immunoassay, etc.).

In another alternative, anti-CD3 monoclonal antibody and any other equivalent antibodies can be sequenced and produced recombinantly by any means known in the art (e.g., humanization, use of transgenic mice to produce fully human antibodies, phage display technology, etc.). In one embodiment, anti-CD3 monoclonal antibody is sequenced and the polynucleotide sequence is then cloned into a vector for expression or propagation. The sequence encoding the antibody of interest may be maintained in a vector in a host cell and the host cell can then be expanded and frozen for future use.

The polynucleotide sequence of anti-CD3 monoclonal antibody and any other equivalent antibodies may be used for genetic manipulation to generate a "humanized" antibody, to improve the affinity, or other characteristics of the antibody. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; and 6,331,415.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains (see, for example, Winter et al. (1991) "*Man-made Antibodies*," Nature 349: 293-299; Lobuglio et al. (1989) "*Mouse/Human Chimeric Monoclonal Antibody In Man: Kinetics And Immune Response*," Proc. Natl. Acad. Sci. (U.S.A.) 86:4220-4224 (1989), Shaw et al. (1987) "*Characterization Of A Mouse/Human Chimeric Monoclonal Antibody (17-1A) To A Colon Cancer Tumor-Associated Antigen*," J. Immunol. 138:4534-4538, and Brown et al. (1987) "*Tumor-Specific Genetically Engineered Murine/Human Chimeric Monoclonal Antibody*," Cancer Res. 47:3577-3583). Other references describe rodent CDRs grafted into a human supporting framework region (FR) prior to fusion with an appropriate human antibody constant domain (see, for example, Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; and Jones et al. (1986) "*Replacing The Complementarity-Determining Regions In A Human Antibody With Those From A Mouse*," Nature 321: 522-525). Another reference describes rodent CDRs supported by recombinantly veneered rodent framework regions. See, for example, European Patent Publication No. 519,596. These "humanized" molecules are designed to minimize unwanted immunological response toward rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning, CDR-Grafting, And Rapid Expression Of A Murine Monoclonal Antibody Directed Against The CD18 Component Of Leukocyte Integrins*," Nucl. Acids Res. 19:2471-2476 and in U.S. Pat. Nos. 6,180,377; 6,054,297; 5,997,867; and 5,866,692.

The invention also encompasses single chain variable region fragments ("scFv") of antibodies of this invention, such as mu-anti-CD3. Single chain variable region fragments are made by linking light and/or heavy chain variable regions by using a short linking peptide. Bird et al. (1988) ("Single-Chain Antigen-Binding Proteins," Science 242: 423-426) describes example of linking peptides which bridge approximately 3.5 nm between the carboxy terminus of one variable region and the amino terminus of the other variable region. Linkers of other sequences have been designed and used (Bird et al. (1988) "*Single-Chain Antigen-Binding Proteins*," Science 242:423-426). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The invention includes modifications to anti-CD3 antibodies and their binding fragments. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

The fact that a single amino acid alteration of a CDR residue can result in loss of functional binding (Rudikoff, S. etc. (1982) "*Single Amino Acid Substitution Altering Antigen-Binding Specificity*," Proc. Natl. Acad. Sci. (USA) 79(6):1979-1983) provides a means for systematically identifying alternative functional CDR sequences. In one preferred method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original (functional) CDR sequence to the identity of the substituted (non-functional) variant CDR sequence, the BLOSUM62.iij substitution score for that substitution can be identified. The BLOSUM system provides a matrix of amino acid substitutions created by analyzing a database of sequences for trusted alignments (Eddy, S. R. (2004) "*Where Did The BLOSUM62 Alignment Score Matrix Come From?*," Nature Biotech. 22(8):1035-

1036; Henikoff, J. G. (1992) "Amino acid substitution matrices from protein blocks," Proc. Natl. Acad. Sci. (USA) 89:10915-10919; Karlin, S. et al. (1990) "*Methods For Assessing The Statistical Significance Of Molecular Sequence Features By Using General Scoring Schemes,*" Proc. Natl. Acad. Sci. (USA) 87:2264-2268; Altschul, S. F. (1991) "*Amino Acid Substitution Matrices From An Information Theoretic Perspective,*" J. Mol. Biol. 219, 555-565. Currently, the most advanced BLOSUM database is the BLOSUM62 database (BLOSUM62.iij). Table 1 presents the BLOSUM62.iij substitution scores (the higher the score the more conservative the substitution and thus the more likely the substitution will not affect function). If an antigen-binding fragment comprising the resultant CDR fails to bind to CD3, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

TABLE 1

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | −1 | −2 | −2 | 0 | −1 | −1 | 0 | −2 | −1 | −1 | −1 | −1 | −2 | −1 | +1 | 0 | −3 | −2 | 0 |
| R | −1 | +5 | 0 | −2 | −3 | +1 | 0 | −2 | 0 | −3 | −2 | +2 | −1 | −3 | −2 | −1 | −1 | −3 | −2 | −3 |
| N | −2 | 0 | +6 | +1 | −3 | 0 | 0 | 0 | +1 | −3 | −3 | 0 | −2 | −3 | −2 | +1 | 0 | −4 | −2 | −3 |
| D | −2 | −2 | +1 | +6 | −3 | 0 | +2 | −1 | −1 | −3 | −4 | −1 | −3 | −3 | −1 | 0 | −1 | −4 | −3 | −3 |
| C | 0 | −3 | −3 | −3 | +9 | −3 | −4 | −3 | −3 | −1 | −1 | −3 | −1 | −2 | −3 | −1 | −1 | −2 | −2 | −1 |
| Q | −1 | +1 | 0 | 0 | −3 | +5 | +2 | −2 | 0 | −3 | −2 | +1 | 0 | −3 | −1 | 0 | −1 | −2 | −1 | −2 |
| E | −1 | 0 | 0 | +2 | −4 | +2 | +5 | −2 | 0 | −3 | −3 | +1 | −2 | −3 | −1 | 0 | −1 | −3 | −2 | −2 |
| G | 0 | −2 | 0 | −1 | −3 | −2 | −2 | +6 | −2 | −4 | −4 | −2 | −3 | −3 | −2 | 0 | −2 | −2 | −3 | −3 |
| H | −2 | 0 | +1 | −1 | −3 | 0 | 0 | −2 | +8 | −3 | −3 | −1 | −2 | −1 | −2 | −1 | −2 | −2 | +2 | −3 |
| I | −1 | −3 | −3 | −3 | −1 | −3 | −3 | −4 | −3 | +4 | +2 | −3 | +1 | 0 | −3 | −2 | −1 | −3 | −1 | +3 |
| L | −1 | −2 | −3 | −4 | −1 | −2 | −3 | −4 | −3 | +2 | +4 | −2 | +2 | 0 | −3 | −2 | −1 | −2 | −1 | +1 |
| K | −1 | +2 | 0 | −1 | −3 | +1 | +1 | −2 | −1 | −3 | −2 | +5 | −1 | −3 | −1 | 0 | −1 | −3 | −2 | −2 |
| M | −1 | −1 | −2 | −3 | −1 | 0 | −2 | −3 | −2 | +1 | +2 | −1 | +5 | 0 | −2 | −1 | −1 | −1 | −1 | +1 |
| F | −2 | −3 | −3 | −3 | −2 | −3 | −3 | −3 | −1 | 0 | 0 | −3 | 0 | +6 | −4 | −2 | −2 | +1 | +3 | −1 |
| P | −1 | −2 | −2 | −1 | −3 | −1 | −1 | −2 | −2 | −3 | −3 | −1 | −2 | −4 | +7 | −1 | −1 | −4 | −3 | −2 |
| S | +1 | −1 | +1 | 0 | −1 | 0 | 0 | 0 | −1 | −2 | −2 | 0 | −1 | −2 | −1 | +4 | +1 | −3 | −2 | −2 |
| T | 0 | −1 | 0 | −1 | −1 | −1 | −1 | −2 | −2 | −1 | −1 | −1 | −1 | −2 | −1 | +1 | +5 | −2 | −2 | 0 |
| W | −3 | −3 | −4 | −4 | −2 | −2 | −3 | −2 | −2 | −3 | −2 | −3 | −1 | +1 | −4 | −3 | −2 | +11 | +2 | −3 |
| Y | −2 | −2 | −2 | −3 | −2 | −1 | −2 | −3 | +2 | −1 | −1 | −2 | −1 | +3 | −3 | −2 | −2 | +2 | +7 | −1 |
| V | 0 | −3 | −3 | −3 | −1 | −2 | −2 | −3 | −3 | +3 | +1 | −2 | +1 | −1 | −2 | −2 | 0 | −3 | −1 | +4 |

The invention thus contemplates the use of random mutagenesis to identify improved CDRs. Phage display technology can alternatively be used to increase (or decrease) CDR affinity. This technology, referred to as affinity maturation, employs mutagenesis or "CDR walking" and re-selection uses the target antigen or an antigenic fragment thereof to identify antibodies having CDRs that bind with higher (or lower) affinity to the antigen when compared with the initial or parental antibody (See, e.g. Glaser et al. (1992) J. Immunology 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased or decreased affinity to the antigen (e.g., ELISA) (See Wu et al. 1998, Proc Natl. Acad Sci. USA 95:6037; Yelton et al., 1995, J. Immunology 155:1994). CDR walking which randomizes the light chain may be used possible (See Schier et al., 1996, J. Mol. Bio. 263:551).

Methods for accomplishing such affinity maturation are described for example in: Krause, J. C. et al. (2011) "*An Insertion Mutation That Distorts Antibody Binding Site Architecture Enhances Function Of A Human Antibody*," MBio. 2(1) pii: e00345-10. doi: 10.1128/mBio.00345-10; Kuan, C. T. et al. (2010) "*Affinity-Matured Anti-Glycoprotein NMB Recombinant Immunotoxins Targeting Malignant Gliomas And Melanomas*," Int. J. Cancer 10.1002/ijc.25645; Hackel, B. J. et al. (2010) "*Stability And CDR Composition Biases Enrich Binder Functionality Landscapes*," J. Mol. Biol. 401(1):84-96; Montgomery, D. L. et al. (2009) "*Affinity Maturation And Characterization Of A Human Monoclonal Antibody Against HIV-1 gp41*," MAbs 1(5):462-474; Gustchina, E. et al. (2009) "*Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth*," Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions*," J. Mol. Biol. 388(3):541-558; Bostrom, J. et al. (2009) "*Improving Antibody Binding Affinity And Specificity For Therapeutic Development*," Methods Mol. Biol. 525: 353-376; Steidl, S. et al. (2008) "*In Vitro Affinity Maturation Of Human GM-CSF Antibodies By Targeted CDR-Diversification*," Mol. Immunol. 46(1):135-144; and Barderas, R. et al. (2008) "Affinity maturation of antibodies assisted by in silico modeling," Proc. Natl. Acad. Sci. (USA) 105(26): 9029-9034. In a preferred embodiment, multi-well plates may be coated with a selected CD3 antibody (e.g., 100 ng/well in carbonate buffer at room temperature for 2 hrs) and subsequently incubated with soluble CD3 added at a dilution of 1/10 and incubated at room temperature for 16 hrs or diluted to a concentration of 50 ng/ml in PBS-T-BSA (0.05 ml added to each well and incubated for at least 2 h at room temperature). The plate is then washed and dilutions of recombinant antibodies starting at 0.5 μg/ml in PBS-T-BSA are then added and incubated for 1 hr at room temp. Binding of recombinant antibodies to the captured antigen is then measured using, for example, an anti-human IgG-HRP conjugate and TMB substrate. After stopping color development using dilute sulfuric acid, the plate is read at 450 nM and higher affinity antibodies identified (see, e.g., U.S. Pat. No. 7,351,803).

The invention includes polypeptides comprising an amino acid sequence of the antibodies of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an anti-CD3 polypeptide could be produced by an automated polypeptide synthesizer employing the solid phase method.

The invention also encompasses fusion proteins comprising one or more fragments or regions from the polypeptides and antibodies of this invention. In one embodiment, a fusion polypeptide is provided that comprises at least 10 contiguous amino acids of variable light chain region and at least 10 amino acids of variable heavy chain region. In another embodiment, the fusion polypeptide contains a heterologous immunoglobulin constant region. In another embodiment, the fusion polypeptide contains a light chain variable region and a heavy chain variable region of an antibody produced from a publicly-deposited hybridoma. For purposes of this invention, an antibody fusion protein contains one or more polypeptide domains that specifically bind to CD3 and another amino acid sequence to which it is not attached in the native molecule, for example, a heterologous sequence or a homologous sequence from another region.

An anti-CD3 polypeptide, and other CD3 agonists, antagonists and modulators can be created by methods known in the art, for example, synthetically or recombinantly. One method of producing such molecules involves chemical synthesis of the polypeptide, followed by treatment under oxidizing conditions appropriate to obtain the native conformation, that is, the correct disulfide bond linkages. This can be accomplished using methodologies well known to those skilled in the art (see, e.g., Kelley, R. F. et al. (1990) In: GENETIC ENGINEERING PRINCIPLES AND METHODS, Setlow, J. K. Ed., Plenum Press, N.Y., vol. 12, pp 1-19; Stewart, J. M et al. (1984) SOLID PHASE PEPTIDE SYNTHESIS, Pierce Chemical Co., Rockford, IL; see also U.S. Pat. Nos. 4,105,603; 3,972,859; 3,842,067; and 3,862,925).

Polypeptides of the invention may be conveniently prepared using solid phase peptide synthesis (Merrifield, B. (1986) "Solid Phase Synthesis," Science 232(4748):341-347; Houghten, R. A. (1985) "*General Method For The Rapid Solid-Phase Synthesis Of Large Numbers Of Peptides: Specificity Of Antigen-Antibody Interaction At The Level Of Individual Amino Acids*," Proc. Natl. Acad. Sci. (U.S.A.) 82(15):5131-5135; Ganesan, A. (2006) "*Solid-Phase Synthesis In The Twenty-First Century*," Mini Rev. Med. Chem. 6(1):3-10).

In yet another alternative, fully human antibodies may be obtained through the use of commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are XENOMOUSE™ (Abgenix, Inc., Fremont, CA) and HuMAb-MOUSE® and TC MOUSE™ (both from Medarex, Inc., Princeton, NJ).

In an alternative, antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants {e.g., tobacco) or transgenic milk. Suitable methods for expressing antibodies recombinantly in plants or milk have been disclosed (see, for example, Peeters et al. (2001) "*Production Of Antibodies And Antibody Fragments In Plants*," Vaccine 19:2756; Lonberg, N. et al. (1995) "*Human Antibodies From Transgenic Mice*," Int. Rev. Immunol 13:65-93; and Pollock et al. (1999) "*Transgenic Milk As A Method For The Production Of Recombinant Antibodies*," J. Immunol Methods 231:147-157). Suitable methods for making derivatives of antibodies, e.g., humanized, single chain, etc. are known in the art. In another alternative, antibodies may be made recombinantly by phage display technology (see, for example, U.S. Pat. Nos. 5,565,332; 5,580,717; 5,733,743; 6,265,150; and Winter, G. et al. (1994) "*Making Antibodies By Phage Display Technology*," Annu. Rev. Immunol. 12.433-455).

The antibodies or protein of interest may be subjected to sequencing by Edman degradation, which is well known to those of skill in the art. The peptide information generated from mass spectrometry or Edman degradation can be used to design probes or primers that are used to clone the protein of interest.

An alternative method of cloning the protein of interest is by "panning" using purified CD3 or portions thereof for cells expressing the antibody or protein of interest. The "panning" procedure may be conducted by obtaining a cDNA library from tissues or cells that express CD3, overexpressing the cDNAs in a second cell type, and screening the transfected cells of the second cell type for a specific binding to CD3. Detailed descriptions of the methods used in cloning mammalian genes coding for cell surface proteins by "panning" can be found in the art (see, for example, Aruffo, A. et al. (1987) "*Molecular Cloning Of A CD28 cDNA By A High-Efficiency COS Cell Expression System*," Proc. Natl. Acad. Sci. (U.S.A.) 84:8573-8577 and Stephan, J. et al. (1999) "*Selective Cloning Of Cell Surface Proteins Involved In Organ Development: Epithelial Glycoprotein Is Involved In Normal Epithelial Differentiation*," Endocrinol. 140:5841-5854).

cDNAs encoding anti-CD3 antibodies, and other CD3 peptide agonists, antagonists and modulators can be obtained by reverse transcribing the mRNAs from a particular cell type according to standard methods in the art. Specifically, mRNA can be isolated using various lytic enzymes or chemical solutions according to procedures set forth in, for example, MOLECULAR CLONING: A LABORATORY MANUAL, Third Edition (Sambrook et al. Eds., 2001) Cold Spring Harbor Press, Cold Spring Harbor, NY) or extracted using commercially available nucleic-acid-binding resins following the accompanying instructions provided by manufacturers (e.g., Qiagen, Invitrogen, Promega). The synthesized cDNAs may then be introduced into an expression vector to produce the antibody or protein of interest in cells of a second type. It is implied that an expression vector must be replicable in the host cells either as an episome or as an integral part of the chromosomal DNA. Suitable expression vectors include but are not limited to plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of suitable mammalian host cells include but are not limited to COS, HeLa, and CHO cells. Preferably, the host cells express the cDNAs at a level of about 5-fold higher, more preferably 10-fold higher, even more preferably 20-fold higher than that of the corresponding endogenous antibody or protein of interest, if present, in the host cells. Screening the host cells for a specific binding to CD3 is effected by an immunoassay or FACS. A cell over-expressing the antibody or protein of interest can be identified.

III. Methods for Screening Polypeptides and Monoclonal Antibodies

Several methods may be used to screen polypeptides and monoclonal antibodies that bind to CD3. It is understood that "binding" refers to biologically or immunologically relevant specific binding, and does not refer to non-specific binding that may occur, for example, when an immunoglobulin is used at a very high concentration against a non-specific target. In one embodiment, monoclonal antibodies are screened for binding to CD3 using standard screening techniques. In this manner, anti-CD3 monoclonal antibody was obtained. The preferred hybridomas of the present invention are those that produce antibodies mAb1 and mAb2, or chimeric or humanized derivatives thereof. However, additional monoclonal antibodies that bind to CD3 may be identified. For this purpose, monoclonal antibodies are screened for their differential ability to bind to human CD3 as well as a primate CD3.

Any of several different detection systems may be utilized to detect binding of antibodies to tissue section. Typically, immunohistochemistry involves the binding of a primary antibody to the tissue and then a secondary antibody reactive against the species from the primary antibody was generated and conjugated to a detectable marker (e.g., horseradish peroxidase (HRP), or diaminobenzedine (DAB)). One alternative method that may be used is polyclonal mirror image complementary antibodies or polyMICA™ (polyclonal Mirror Image Complementary Antibodies; The Binding Site Limited, Birmingham, UK; Mangham, D. C. et al. (1999) "*A Novel Immunohistochemical Detection System Using Mirror Image Complementary Antibodies (MICA)*," Histopathology 35(2):129-33). The PolyMICA™ technique can be used to test binding of primary antibodies (e.g., anti-CD3 antibodies) to normal and cancerous tissue. Several kinds of polyMICA™ Detection kits are commercially available: Product No. HK004.D is a polyMICA™ Detection kit which uses DAB chromagen; Product No. HK004.A is a polyMICA™ Detection kit which uses AEC chromagen. Alternatively, the primary antibody may be directly labeled with the detectable marker.

IV. Methods of Characterizing Anti-CD3 Antibodies

Any of several methods can be used to characterize anti-CD3 antibodies. One method is to identify the epitope to which it binds. Epitope mapping is commercially available from various sources, for example, Pepscan Systems (Lelystad, The Netherlands). Epitope mapping can be used to determine the sequence to which an anti-CD3 antibody binds. The epitope can be a linear epitope, i.e., contained in a single stretch of amino acids, or a conformational epitope formed by a three-dimensional interaction of amino acids that may not necessarily be contained in a single stretch.

Peptides of varying lengths (e.g., preferably at least 4-6 amino acids long) can be isolated or synthesized {e.g., recombinantly) and used for binding assays with anti-CD3 antibody. The epitope to which anti-CD3 antibody binds can be determined in a systematic screening by using overlapping peptides derived from the extracellular sequence and determining binding by anti-CD3 antibody.

Yet another method that can be used to characterize an anti-CD3 antibody is to use competition assays with other antibodies known to bind to the same antigen, i.e., CD3 to determine if anti-CD3 antibodies binds to the same epitope as other antibodies. Examples of commercially available antibodies to CD3 may be available and may be identified using the binding assays taught herein. Competition assays are well known to those of skill in the art, and such procedures and illustrative data are detailed further in the Examples. Anti-CD3 antibodies can be further characterized by the tissues, type of cancer or type of tumor to which they bind.

V. Preferred Compositions of the Present Invention

The present invention encompasses compositions, including pharmaceutical compositions, comprising anti-CD3 antibodies, polypeptides derived from anti-CD3 antibodies, polynucleotides comprising sequence encoding anti-CD3 antibodies, and other agents as described herein. The invention further provides for conjugates of any CD3 peptide agonist, antagonist or modulator, and additional chemical structures that support the intended function or functions of the particular CD3 peptide agonist, antagonist or modulator. These conjugates include CD3 peptide agonist, antagonist or modulator covalently bound to a macromolecule such as any insoluble, solid support matrix used in the diagnostic, screening or purification procedures discussed herein. Suitable matrix materials include any substance that is chemically inert, has high porosity and has large numbers of functional groups capable of forming covalent linkages with peptide ligands. Examples of matrix materials and procedures for preparation of matrix-ligand conjugates are described in Dean et al. (Eds) AFFINITY CHROMATOGRAPHY: A PRACTICAL APPROACH, IRL Press (1985); Lowe, "An Introduction to Affinity Chromatography", in Work et al. (eds) LABORATORY TECHNIQUES IN BIOCHEMISTRY AND MOLECULAR BIOLOGY, Vol. 7, Part II, North-Holland (1979); Porath et al., "Biospecific Affinity Chromatography", in Neurath, H. et al. (eds), THE PROTEINS, 3rd ed., Vol. 1, pp. 95-178 (1975); and Schott, H. AFFINITY CHROMATOGRAPHY, Macel Dekker, Inc. NY (1984).

Also provided herein are conjugates of CD3 peptide agonist, antagonist or modulator and any reporter moiety used in the diagnostic procedures discussed herein. The CD3 peptide agonist, antagonist or modulator agents, polypeptides and proteins of this invention, including anti-CD3 antibodies, are further identified and characterized by any (one or more) of the following criteria:

(1) an ability to specifically bind human CD3 as endogenously expressed on the surface of a normal human T cell;
(2) an ability to specifically bind human CD3 as endogenously expressed on the surface of a human leukemic T cell;
(3) an ability to specifically bind non-human CD3 (e.g., CD3 of cynomolgus monkey) as endogenously expressed on the surface of a normal non-human T cell;
(4) an ability to specifically bind a non-human CD3 as endogenously expressed on the surface of a non-human leukemic T cell;
(5) an ability to neutralize (i.e., block or interfere with binding) the formation of the CD3 complex; an ability to neutralize the formation of the TCR complex;
(6) an ability to modulate (either antagonistically or agonistically) signaling by the TCR complex;
(7) an ability to bind the Fc receptor;
(8) an ability to competitively inhibit preferential binding of a known anti-CD3 antibody to CD3, including the ability to preferentially bind to the same CD3 epitope to which the original antibody preferentially binds;
(9) an ability to bind to a portion of CD3 that is exposed on the surface of a living cell in vitro or in vivo; an ability to bind to a portion of CD3 that is exposed on the surface of a living cancer cell;
(10) an ability to deliver a chemotherapeutic agent into a cancerous T cell; and/or
(11) an ability to deliver a therapeutic agent, toxin or detectable marker into a T cell.

A preferred antibody of the invention will exhibit differential IHC staining of tumor tissue relative to normal, non-cancerous tissue, and will moreover be capable of testing in primate (and particularly cynomolgus monkey) models of antibody efficacy. Preferred antibodies of the present invention will additionally exhibit desirable levels of affinity and antigen specificity. Preferred antibodies of the present invention will additionally exhibit desirable levels of immunomodulatory activity and cellular internalization.

In some embodiments, the antibody of the invention is an antibody that is produced by hybridoma mAb1 or hybridoma mAb2, which respectively express murine antibody mAb1 and murine antibody mAb2, or progeny thereof. The present invention also encompasses various formulations of antibodies produced by these hybridomas and equivalent antibodies or polypeptide fragments (e.g., Fab, Fab', F(ab')2 Fv, Fc, etc.), chimeric antibodies, single chain (scFv), mutants thereof, fusion proteins comprising an antibody portion, humanized antibodies, and any other modified configuration of any of these or equivalent antibodies that comprises an antigen (CD3), recognition site of the required specificity. The invention also provides human antibodies displaying one or more of the biological characteristics of an anti-CD3 family member. The equivalent antibodies of the anti-CD3 family (including humanized antibodies and human antibodies), polypeptide fragments, and polypeptides comprising any of these fragments are identified and characterized by any (one or more) of the criteria described above.

Accordingly, the invention provides any of the following (or compositions, including pharmaceutical compositions, comprising any of the following): (a) an antibody produced by the host cell or its progeny; (b) a humanized form of such an antibody; (c) an antibody comprising one or more of the light chain and/or heavy chain variable regions of such an antibody; (d) a chimeric antibody comprising variable regions homologous or derived from variable regions of a heavy chain and a light chain of such an antibody, and constant regions homologous or derived from constant regions of a heavy chain and a light chain of a human antibody; (e) an antibody comprising one or more of the light chain and/or heavy chain CDRs (at least one, two, three, four, five, or six) of such an antibody; (f) an antibody comprising a heavy and/or a light chain of such an antibody; (g) a human antibody that is equivalent to such an antibody. A humanized form of the antibody may or may not have CDRs identical to that original antibody, or antibody produced by the host cell identified above. Determination of CDR regions is well within the skill of the art. Other embodiments include antibodies that have at least two, three, four, five, or six CDR(s) that are substantially homologous to at least two, three, four, five or six CDRs of an antibody produced from a hybridoma deposited as identified herein, or derived from such an antibody. It is understood that, for purposes of this invention, binding specificity and/or overall activity is generally retained, although the extent of activity may vary compared to an antibody produced by a deposited hybridoma (may be greater or lesser). The invention also provides methods of making any of these antibodies. Methods of making antibodies are known in the art and are described herein.

The invention also provides polypeptides comprising an amino acid sequence of the antibodies of the invention. In some embodiments, the polypeptide comprises one or more of the light chain and/or heavy chain variable regions of the antibody. In some embodiments, the polypeptide comprises one or more of the light chain and/or heavy chain CDRs of the antibody. In some embodiments, the polypeptide comprises three CDRs of the light chain and/or heavy chain of the antibody. In some embodiments, the polypeptide comprises an amino acid sequence of the antibody that has any of the following: at least 5 contiguous amino acids of a sequence of the original antibody, at least 8 contiguous amino acids, at least about 10 contiguous amino acids, at least about 15 contiguous amino acids, at least about 20 contiguous amino acids, at least about 25 contiguous amino acids, at least about 30 contiguous amino acids, wherein at least 3 of the amino acids are from a variable region of the antibody. In one embodiment, the variable region is from a light chain of the original antibody. In another embodiment, the variable region is from a heavy chain of the antibody. In another embodiment, the 5 (or more) contiguous amino acids are from a complementarity-determining region (CDR) of the antibody.

In some embodiments of this invention, cells of this invention that express CD3, a portion of CD3, anti-CD3 antibodies or other CD3-binding polypeptides of this invention are administered directly to an individual to modulate in vivo CD3 biological activity.

The preferred anti-CD3 antibodies of the present invention are mAb1 and mAb2, and humanized or chimeric derivatives and antigen-binding fragments thereof that are reactive toward the human and cynomolgus CD3 molecule. The amino acid and encoding polynucleotide sequences of the variable light chain and variable heavy chain of murine antibodies mAb1 and mAb2 are shown below. The sequences of the CDRs of the exemplary antibodies (mAb1 and mAb2) are shown in boldface and underlined.

A. Sequences of Variable Regions of Murine Monoclonal Antibody mAb1

Amino Acid Sequence of Murine Monoclonal Antibody mAb1 Variable Light Chain (SEQ ID NO:1):

```
QVVLTQSPAI MSAFPGEKVT MTCSASSSVS YMNWYQQKSG
TSPKRWIYDS SKLASGVPAR FSGSGSGTSY SLTISSMETE
DAATYYCQQW SRNPPTFGGG TKLQITR
```

Polynucleotide Sequence Encoding Murine Monoclonal Antibody mAb1 Variable Light Chain (SEQ ID NO:2):

```
caggtggtgc tgacccagtc ccccgccatc atgtccgcct
tccccggcga gaaagtgaca atgacctgct ccgcctcctc
ctccgtgtcc tacatgaact ggtatcagca gaagtccggc
acctccccca agcggtggat ctacgactcc tccaagctgg
cctccggcgt gcccgccaga ttctctggct ccggctccgg
caccagctac tccctgacca tctcctccat ggaaaccgag
gacgccgcca cctactactg ccagcagtgg tcccggaacc
cccctacctt cggcggaggc accaagctgc agatcaccag a
```

Amino Acid Sequence of Murine Monoclonal Antibody mAb1 Variable Heavy Chain (SEQ ID NO:3):

```
QVQLQQSGAE LARPGASVKM SCKASGYTFT RSTMHWVKQR
PGQGLEWIGY INPSSAYTNY NQKFKDKATL TADKSSSTAY
MQLSSLTSED SAVYYCASPQ VHYDYNGFPY WGQGTLVTVS S
```

Polynucleotide Sequence Encoding mAb1 Murine Monoclonal Antibody Variable Heavy Chain (SEQ ID NO:4):

```
caggtgcagc tgcagcagtc tggcgccgag ctggccagac
ctggcgcctc cgtgaagatg tcctgcaagg cctccggcta
caccttcacc cggtccacca tgcactgggt gaaacagcgg
cctggacagg gcctggaatg gatcggctac atcaacccct
ccagcgccta caccaactac aaccagaagt tcaaggacaa
ggccaccctg accgccgaca gtcctccag caccgcctac
atgcagctgt cctccctgac ctccgaggac tccgccgtgt
actactgcgc ctccccccag gtgcactacg actacaacgg
cttcccctac tggggccagg gcaccctggt gacagtgtcc tcc
```

B. Sequences of Variable Regions of Murine Monoclonal Antibody mAb2

Amino Acid Sequence Of Murine Monoclonal Antibody mAb2 Variable Light Chain (SEQ ID NO:5):
```
QAVVTQESAL    TTSPGETVTL    TCRSSTGAVT
TSNYANWVQE    KPDHLFTGLI    GGTNKRAPGV
PARFSGSLIG    DKAALTITGA    QTEDEAIYFC
ALWYSNLWVF    GGGTKLTVLG
```

Polynucleotide Sequence Encoding Murine Monoclonal Antibody mAb2 Variable Light Chain (SEQ ID NO:6):

```
caggccgtgg tgacacagga gtcagctctg accacatccc
caggcgaaac agtgactctg acctgcagat ccagcactgg
agcagtgact acctctaact acgctaattg ggtgcaggag
aagcccgacc acctgttcac tgggctgatc ggcggaacca
acaaagggc acccggtgtg cctgcccggt tttctggcag
tctgatcgga gacaaggccg ctctgacaat tactggcgcc
cagacagagg atgaagctat ttacttctgt gcactgtggt
atagcaatct gtgggtgttt gggggtggca ccaaactgac
agtgctggga
```

Amino Acid Sequence of mAb2 Murine Monoclonal Antibody Variable Heavy Chain (SEQ ID NO:7):

```
EVKLLESGGG LVQPKGSLKL SCAASGFTFN TYAMNWVRQA
PGKGLEWVAR IRSKYNNYAT YYADSVKDRF TISRDDSQSI
LYLQMNNLKT EDTAMYYCVR HGNFGNSYVS WFAYWGQGTL
VTVSA
```

Polynucleotide Sequence Encoding Murine Monoclonal Antibody mAb2 Variable Heavy Chain (SEQ ID NO:8):

```
gaggtgaagc tgctggaaag cggcggagga ctggtgcagc
caaagggatc actgaaactg tcctgcgccg cctccggctt
cacctttaac acatacgcta tgaattgggt gcgacaggca
cctggcaagg gcctggagtg ggtggcaagg atcaggtcca
agtacaacaa ttatgcaacc tactatgccg actctgtgaa
ggatagattc acaatcagtc gcgacgattc ccagagcatt
ctgtatctgc agatgaacaa tctgaaaact gaagacaccg
ccatgtacta ttgtgtgcgg cacggtaact tcggcaattc
ttacgtgtct tggtttgctt attggggaca ggggacactg
gtgactgtgt cttcc
```

Position 40 of the heavy chain is a high affinity MHC class II binding peptide anchor residue. Positions 44, 48, 54, 94, 99 and 108 of the heavy chain are moderate affinity MHC class II binding peptide anchor residues. Position 69 of the light chain is a high affinity MHC class II binding peptide anchor residue. Position 59 of the light chain is a moderate affinity MHC class II binding peptide anchor residue. These residues may be substituted, using standard molecular biology techniques, to a residue in order to reduce or remove the MHC class II recognition site.

C. Fc-Engineered CD3 Antibodies

In traditional immune function, the interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All of these interactions are initiated through the binding of the Fc domain of antibodies or immune complexes to specialized cell surface receptors on hematopoietic cells. The diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor. The amino acid sequence of the IgG1 Fc region is shown below (as SEQ ID NO:9, numbered according to Kabat et al., SEQUENCE OF PROTEINS OF IMMUNOLOGICAL INTEREST, 5$^{th}$ Ed. Public Health Service, NIH, MD (1991), expressly incorporated herein by reference, and hereafter referred to as "Kabat EU"). Residues 230-341 are the Fc CH2 region. Residues 342-447 are the Fc CH3 region:

```
                                              SEQ ID NO: 9
PAPELLGGPS  VFLFPPKPKD  TLMISRTPEV  TCVVVDVSHE
230         240         250         260

DPEVKFNWYV  DGVEVHNAKT  KPREEQYNST  YRVVSVLTVL
270         280         290         300

HQDWLNGKEY  KCKVSNKALP  APIEKTISKA  KGQPREPQVY
310         320         330         340

TLPPSREEMT  KNQVSLTCLV  KGFYPSDIAV  EWESNGQPEN
350         360         370         380

NYKTTPPVLD  SDGSFFLYSK  LTVDKSRWQQ  GNVFSCSVMH
390         400         410         420

EALHNHYTQK  SLSLSPGK
430         440
```

Since Fc receptor (FcR)-non-binding CD3-specific antibodies are minimally depleting, it has been proposed that they may alter TCR signals in a way that might induce immune tolerance (St. Clair E. W. (2009) "*Novel Targeted Therapies for Autoimmunity*," Curr. Opin. Immunol. 21(6): 648-657). Thus, such therapy has potential application in the treatment of autoimmune disease and host vs. graft tissue rejection. FcR non-binding CD3-specific antibodies have also been postulated to induce remission in type 1 diabetes mellitus tolerance (St. Clair E. W. (2009) "*Novel Targeted Therapies for Autoimmunity*," Curr. Opin. Immunol. 21(6): 648-657; Masharani, U. B. et al. (2010) "*Teplizumab Therapy For Type 1 Diabetes*," Expert Opin. Biol. Ther. 10(3):459-465).

The present invention thus includes antibodies that specifically bind to CD3 that comprise a variant Fc region having Fc regions that are modified (e.g., substitutions, deletions, insertions in one or more portions) so as to be unable or less able to bind to the Fc receptor (relative to an antibody having the same CDRs but a wild-type Fc region).

In one embodiment, such antibodies will be incapable of binding to any Fc receptor. Alternatively, the Fc region of the antibody will be modified so as to permit it to bind to Fc receptors such as FcγRIIB that are inhibitory, but not to Fc receptors such as FcγRIIA, FcγRIIIA or FcγRIIIB that promote activation of the immune system.

Preferably, the binding properties of the molecules of the invention are characterized by in vitro functional assays for determining one or more FcγR mediator effector cell functions. The affinities and binding properties of the molecules, e.g., antibodies, of the invention for an FcγR can be determined using in vitro assays (biochemical or immunological based assays) known in the art for determining antibody-antigen or Fc-FcγR interactions, i.e., specific binding of an antigen to an antibody or specific binding of an Fc region to an FcγR, respectively, including but not limited to ELISA assay, surface plasmon resonance assay, immunoprecipitation assays. In most preferred embodiments, the molecules of the invention have similar binding properties in in vivo models (such as those described and disclosed herein) as those in in vitro based assays. However, the present invention does not exclude molecules of the invention that do not exhibit the desired phenotype in in vitro based assays but do exhibit the desired phenotype in vivo.

In some embodiments, the molecules of the invention comprising a variant Fc region comprise at least one amino acid modification (for example, possessing 1, 2, 3, 4, 5, 6, 7, 8, 9, or more amino acid modifications) in the CH3 domain of the Fc region, which is defined as extending from amino acids 342-447. In other embodiments, the molecules of the invention comprising a variant Fc region comprise at least one amino acid modification (for example, possessing 1, 2, 3, 4, 5, 6, 7, 8, 9, or more amino acid modifications) in the CH2 domain of the Fc region, which is defined as extending from amino acids 231-341. In some embodiments, the molecules of the invention comprise at least two amino acid modifications (for example, possessing 2, 3, 4, 5, 6, 7, 8, 9, or more amino acid modifications), wherein at least one such modification is in the CH3 region and at least one such modification is in the CH2 region. The invention further encompasses amino acid modification in the hinge region. In a particular embodiment, the invention encompasses amino acid modification in the CH1 domain of the Fc region, which is defined as extending from amino acids 216-230.

In particularly preferred embodiments, the invention encompasses molecules comprising a variant Fc region wherein said variant confers or has a decreased ADCC activity and/or a decreased binding to Fc□RIIA (CD32A), as measured using methods known to one skilled in the art and exemplified herein. The ADCC assays used in accordance with the methods of the invention may be NK dependent or macrophage dependent.

In particularly preferred embodiments, the invention encompasses molecules comprising a variant Fc region wherein said variant confers or has a decreased ADCC activity and/or a decreased binding to FcγRIIIA (CD16A), as measured using methods known to one skilled in the art and exemplified herein. The ADCC assays used in accordance with the methods of the invention may be NK dependent or macrophage dependent.

The Fc variants of the present invention may be combined with other Fc modifications, such as those disclosed in U.S. Pat. Nos. 7,632,497; 7,521,542; 7,425,619; 7,416,727; 7,371,826; 7,355,008; 7,335,742; 7,332,581; 7,183,387; 7,122,637; and 6,737,056; in PCT Publications Nos. WO 2008/105886; WO 2008/002933; WO 2007/021841; WO 2007/106707; WO 06/088494; WO 05/115452; WO 05/110474; WO 04/1032269; and in WO 04/063351; and in Presta, L. G. et al. (2002) "*Engineering therapeutic antibodies for improved function*," Biochem. Soc. Trans. 30(4): 487-490; Shields, R. L. et al. (2002) "*Lack of fucose on human IgG1 N-linked oligosaccharide improves binding to human Fcgamma RIII and antibody-dependent cellular toxicity*," J. Biol. Chem. 26; 277(30):26733-26740 and Shields, R. L. et al. (2001) "*High resolution mapping of the binding site on human IgG1 for Fc gamma RI, Fc gamma RII, Fc gamma RIII, and FcRn and design of IgG1 variants with improved binding to the Fc gamma R*," J. Biol. Chem. 276(9):6591-6604). The invention encompasses combining an Fc variant of the invention with other Fc modifications to provide additive, synergistic, or novel properties to the modified antibody.

In other embodiments, the invention encompasses the use of any Fc variant known in the art, such as those disclosed in Jefferis, B. J. et al. (2002) "*Interaction Sites On Human IgG-Fc For FcgammaR: Current Models*," Immunol. Lett. 82:57-65; Presta, L. G. et al. (2002) "*Engineering Therapeutic Antibodies For Improved Function*," Biochem. Soc. Trans. 30:487-90; Idusogie, E. E. et al. (2001) "*Engineered Antibodies With Increased Activity To Recruit Complement*," J. Immunol. 166:2571-75; Shields, R. L. et al. (2001) "*High Resolution Mapping Of The Binding Site On Human IgG1 For Fc Gamma RI, Fc Gamma RII, Fc Gamma RIII, And FcRn And Design Of IgG1 Variants With Improved Binding To The Fc gamma R*," J. Biol. Chem. 276:6591-6604; Idusogie, E. E. et al. (2000) "*Mapping Of The C1q Binding Site On Rituxan, A Chimeric Antibody With A Human IgG Fc*," J. Immunol. 164:4178-84; Reddy, M. P. et al. (2000) "*Elimination Of Fc Receptor-Dependent Effector Functions Of A Modified IgG4 Monoclonal Antibody To Human CD4*," J. Immunol. 164:1925-1933; Xu, D. et al. (2000) "*In Vitro Characterization of Five Humanized OKT3 Effector Function Variant Antibodies*," Cell. Immunol. 200:16-26; Armour, K. L. et al. (1999) "*Recombinant human IgG Molecules Lacking Fcgamma Receptor I Binding And Monocyte Triggering Activities*," Eur. J. Immunol. 29:2613-24; Jefferis, R. et al. (1996) "*Modulation Of Fc(Gamma)R And Human Complement Activation By IgG3-Core Oligosaccharide Interactions*," Immunol. Lett. 54:101-04; Lund, J. et al. (1996) "*Multiple Interactions Of IgG With Its Core Oligosaccharide Can Modulate Recognition By Complement And Human Fc Gamma Receptor I And Influence The Synthesis Of Its Oligosaccharide Chains*," J. Immunol. 157:4963-4969; Hutchins et al. (1995) "*Improved Biodistribution, Tumor Targeting, And Reduced Immunogenicity In Mice With A Gamma 4 Variant Of Campath-1H*," Proc. Natl. Acad. Sci. (U.S.A.) 92:11980-84; Jefferis, R. et al. (1995) "*Recognition Sites On Human IgG For Fc Gamma Receptors: The Role Of Glycosylation*," Immunol. Lett. 44:111-17; Lund, J. et al. (1995) "*Oligosaccharide-Protein Interactions In IgG Can Modulate Recognition By Fc Gamma Receptors*," FASEB J. 9:115-19; Alegre, M. L. et al. (1994) "*A Non-Activating "Humanized" Anti-CD3 Monoclonal Antibody Retains Immunosuppressive Properties In Vivo*," Transplantation 57:1537-1543; Lund et al. (1992) "*Multiple Binding Sites On The CH2 Domain Of IgG For Mouse Fc Gamma R*11," Mol. Immunol. 29:53-59; Lund et al. (1991) "*Human Fc Gamma RI And Fc Gamma RII Interact With Distinct But Overlapping Sites On Human IgG*," J. Immunol. 147:2657-2662; Duncan, A. R. et al. (1988) "*Localization Of The Binding Site For The Human High-Affinity Fc Receptor On IgG*," Nature 332:563-564; U.S. Pat. Nos. 5,624,821; 5,885,573; 6,194,551; 7,276,586; and 7,317,091; and PCT Publications WO 00/42072 and PCT WO 99/58572.

In certain embodiments, the antibody of the invention comprises a variant Fc region (including an Fc derived from any human immunoglobulin type (e.g., IgG, IgE, IgM, IgD, IgA and IgY), or class (e.g., IgG$_1$, IgG$_2$, IgG$_3$, IgG$_4$, IgA$_1$, and IgA$_2$) or subclass), wherein said variant Fc region comprises at least one amino acid modification relative to a wild-type Fc region, which variant Fc region exhibits reduced or abolished binding to one or more effector ligands as determined by standard assays known in the art and disclosed herein, relative to a comparable molecule comprising the wild type Fc region. In certain embodiments, the variant Fc domain of the antibody of the invention comprises an amino acid modification (i.e., insertion, substitution, deletion) at one or more of the residues 233, 234, 235, 236, 237, 238, 265, 270, 297, 298, 299. In a specific embodiment, the one or more amino acid modifications which reduce or abolish binding to one or more effector ligands is a substitution with phenylalanine or proline at position 233; a substitution with alanine at position 234; a substitution with alanine or glutamic acid at position 235; a substitution with alanine at position 236, a substitution with alanine at position 237, a substitution with arginine at position 238; a substitution with alanine or glutamic acid at position 265; a substitution with alanine or asparagine at position 270; a substitution with alanine or glutamine at position 297; a substitution with phenylalanine, asparagine or proline at position 298; a substitution with any amino acid at position 299 other than serine or threonine; or a combination of two or more of the above-listed substitutions. In certain embodiments, the antibody of the invention comprises an Fc domain having a substitution with alanine at position 265 and at position 297; a substitution with alanine at position 265 and with glutamine at position 297; a substitution with glutamic acid at position 265 and with alanine at position 297; or a substitution with glutamic acid at position 265 and with glutamine at position 297. In preferred embodiments, the antibody of the invention comprises an Fc domain having a modification (e.g., substitution, insertion, deletion) at position 234 and position 235 of the Fc region. In a specific example in accordance with this embodiment, the antibody of the invention comprises an Fc domain having a substitution at position 234 with alanine and a substitution at position 235 with glutamic acid. In a yet more preferred embodiment, the antibody of the invention comprises an Fc having a substitution with alanine at position 234 and a substitution with alanine at position 235.

In other embodiments, the antibody of the invention comprises a Fc region, which variant Fc region exhibits reduced or abolished binding to one or more effector ligands as determined by standard assays known in the art and disclosed herein, relative to a comparable control molecule. In certain embodiments, the antibody of the invention has a Fc region that exhibits reduced or abolished binding to one or more effector ligands, which Fc region comprises a phenylalanine or proline at position 233; an alanine at position 234; an alanine or glutamic acid at position 235; an alanine at position 236, an alanine at position 237, an arginine at position 238; an alanine or glutamic acid at position 265; an alanine or asparagine at position 270; an alanine or glutamine at position 297; a phenylalanine, asparagine or proline at position 298; any amino acid at position 299 other than serine or threonine; or a combination of two or more of the above-listed substitutions. In certain embodiments, the antibody of the invention comprises an Fc domain having an alanine at position 265 and at position 297; an alanine at position 265 and a glutamine at position 297; a glutamic acid at position 265 and an alanine at position 297; or a glutamic acid at position 265 and a glutamine at position 297. In certain embodiments, the antibody of the invention comprises an Fc domain having an alanine at 234 and a glutamic acid at position 235. In preferred embodiments, the antibody of the invention comprises an Fc having an alanine at position 234 and an alanine at position 235.

Antibodies of the invention that comprise and Fc domain having an alanine at positions corresponding to 234 and 235 according to the numbering scheme of Kabat are known as "ala-ala" antibodies. In certain embodiments, use of "ala-ala" Fc domains and/or other combinations of amino acid combinations herein described (including combinations comprising "ala-ala" Fc domains) may abolish binding of the Fc domain to all FcγRs. The binding of a Fc domain to one or more FcγRs may be determined by any method described herein and/or known in the art.

In certain embodiments, the one or more amino acid modifications which abolish binding to all FcγRs or reduce or abrogate binding to one or more effector ligands comprise combinations of the modifications listed herein or combinations of the modifications listed herein with any that may confer null binding to any FcR (e.g., FcγRIIIA, FcγRIIIB, FcγRIIA) as determined by the methods disclosed herein or known to one skilled in the art. As readily understood by one of skill in the art, such antibodies of the invention may find particular use in the treatment of an autoimmune disease in that the anti-CD3 antibodies and antigen-binding fragments serve to modulate immune function without the associated first-dose response common to anti-immune cell antibodies.

In certain embodiments, the anti-CD3 antibodies and antigen-binding fragments of the invention, or antigen binding fragments thereof, have diminished (such as, but not limited to, less than 50%, less than 40%, less than 30%, less than 20%, less than 10%, less than 5% or less than 1% as compared to binding by a protein comprising a control Fc domain) or, more preferably, no detectable binding to one or more of any FcγR (e.g., FcγRI, FcγRII or FcγRIII) via its Fc domain as determined by assays routine in the art. In addition or alternatively, the anti-CD3 antibodies and antigen-binding fragments of the invention, or antigen binding fragments thereof, may have diminished (such as, but not limited to, less than 50%, less than 40%, less than 30%, less than 20%, less than 10%, less than 5% or less than 1% as compared to binding by a control protein comprising a control Fc domain) or, more preferably, no detectable binding to any complement receptors, such as, C1q, as determined in routinely used assays. In particular embodiments, the antibody is aglycosylated. In other embodiments, the antibody lacks an Fc domain (e.g., is a Fab fragment, F(ab')$_2$ or single chain antibody).

The antibodies of the invention are thus particularly useful because they have reduced or no in vivo toxicity caused by lymphokine production or cytokine release. Methods of measuring lymphokine production and cytokine release are known and routine in the art and encompassed herein. For example, cytokine release may be measured by measuring secretion of cytokines including but not limited to Interleukin-2 (IL-2). Interleukin-4 (IL-4), Interleukin-6 (IL-6), Interleukin-12 (IL-12), Interleukin-16 (IL-16), PDGF, TGF-α, TGF-β, TNF-α, TNF-β, GCSF, GM-CSF, MCSF, IFN-α, IFN-β, TFN-γ, IGF-I, IGF-II. For example, see, Isaacs et al., 2001, Rheumatology, 40: 724-738; Soubrane et al., 1993, Blood, 81(1): 15-19; each of which is incorporated herein by reference in its entirety.

D. CD3 DART™ Diabodies

As discussed above, the present invention additionally encompasses bispecific, trispecific and multispecific antibodies. A particularly preferred example of such antibodies comprise "DART™" diabody molecules that comprise at least two polypeptide chains which form at least two epitope binding sites, at least one of which specifically binds to CD3. Exemplary "DART™" diabody molecules are disclosed in US20100174053, US20090060910, US20070004909, EP2158221, EP1868650, WO2010080538, WO2008157379, and WO2006113665.

In preferred embodiments, the first polypeptide chain of the DART™ diabody comprises:
(i) a domain (A) comprising a binding region of a light chain variable domain of a first immunoglobulin (VL1) specific for an epitope (1);
(ii) a domain (B) comprising a binding region of a heavy chain variable domain of a second immunoglobulin (VH2) specific for an epitope (2); and
(iii) a domain (C).

The second polypeptide chain of such a DART™ diabody comprises:
(i) a domain (D) comprising a binding region of a light chain variable domain of the second immunoglobulin (VL2) specific for epitope (2);
(ii) a domain (E) comprising a binding region of a heavy chain variable domain of the first immunoglobulin (VH1) specific for epitope (1); and
(iii) a domain (F).

The DART™ diabody domains (A) and (B) do not associate with one another to form an epitope binding site. Similarly, the DART™ diabody domains (D) and (E) do not associate with one another to form an epitope binding site. Rather, DART™ diabody domains (A) and (E) associate to form a binding site that binds epitope (1); said DART™ diabody domains (B) and (D) associate to form a binding site that binds said epitope (2). Domains (C) and (F) are covalently associated together.

Each polypeptide chain of the DART™ diabody molecule comprises a VL domain and a VH domain, which are covalently linked such that the domains are constrained from self-assembly. Interaction of two of the polypeptide chains will produce two VL-VH pairings, forming two eptiope binding sites, i.e., a bivalent molecule. Neither the VH or VL domain is constrained to any position within the polypeptide chain, i.e., restricted to the amino (N) or carboxy (C) terminus, nor are the domains restricted in their relative positions to one another, i.e., the VL domain may be N-terminal to the VH domain and vice-versa. The only restriction is that a complimentary polypeptide chain be available in order to form functional DART™ diabodies. Where the VL and VH domains are derived from the same antibody, the two complimentary polypeptide chains may be identical. For example, where the binding domains are derived from an antibody specific for epitope A (i.e., the binding domain is formed from a $VL_A$-$VH_A$ interaction), each polypeptide will comprise a $VH_A$ and a $VL_A$. Homodimerization of two polypeptide chains of the antibody will result in the formation two $VL_A$-$VH_A$ binding sites, resulting in a bivalent monospecific antibody. Where the VL and VH domains are derived from antibodies specific for different antigens, formation of a functional bispecific DART™ diabody requires the interaction of two different polypeptide chains, i.e., formation of a heterodimer. For example, for a bispecific DART™ diabody, one polypeptide chain will comprise a $VL_A$ and a $VL_B$; homodimerization of said chain will result in the formation of two $VL_A$-$VH_B$ binding sites, either of no binding or of unpredictable binding. In contrast, where two differing polypeptide chains are free to interact, e.g., in a recombinant expression system, one comprising a $VL_A$ and a $VH_B$ and the other comprising a $VL_B$ and a $VH_A$, two differing binding sites will form: $VL_A$-$VH_A$ and $VL_B$-$VH_B$. For all DART™ diabody polypeptide chain pairs, the possibly of misalignment or mis-binding of the two chains is a possibility, i.e., interaction of VL-VL or VH-VH domains; however, purification of functional diabodies is easily managed based on the immunospecificity of the properly dimerized binding site using any affinity based method known in the art or exemplified herein, e.g., affinity chromatography.

One or more of the polypeptide chains of the DART™ diabody may optionally comprise an Fc domain domain or portion thereof (e.g. a CH2 domain, or CH3 domain). The Fc domain or portion thereof may be derived from any immunoglobulin isotype or allotype including, but not limited to, IgA, IgD, IgG, IgE and IgM. In preferred embodiments, the Fc domain (or portion thereof) is derived from IgG. In specific embodiments, the IgG isotype is $IgG_1$, $IgG_2$, $IgG_3$ or $IgG_4$ or an allotype thereof. In one embodiment, the diabody molecule comprises an Fc domain, which Fc domain comprises a CH2 domain and CH3 domain independently selected from any immunoglobulin isotype (i.e. an Fc domain comprising the CH2 domain derived from IgG and the CH3 domain derived from IgE, or the CH2 domain derived from $IgG_1$ and the CH3 domain derived from $IgG_2$, etc.). The Fc domain may be engineered into a polypeptide chain comprising the diabody molecule of the invention in any position relative to other domains or portions of said polypeptide chain (e.g., the Fc domain, or portion thereof, may be c-terminal to both the VL and VH domains of the polypeptide of the chain; may be n-terminal to both the VL and VH domains; or may be N-terminal to one domain and c-terminal to another (i.e., between two domains of the polypeptide chain)).

The Fc domains in the polypeptide chains of the DART™ diabody molecules preferentially dimerize, resulting in the formation of a DART™ molecule that exhibits immunoglobulin-like properties, e.g., Fc-FcγR, interactions. Fc comprising diabodies may be dimers, e.g., comprised of two polypeptide chains, each comprising a VH domain, a VL domain and an Fc domain. Dimerization of said polypeptide chains results in a bivalent DART™ diabody comprising an Fc domain, albeit with a structure distinct from that of an unmodified bivalent antibody. Such DART™ diabody molecules will exhibit altered phenotypes relative to a wild-type immunoglobulin, e.g., altered serum half-life, binding properties, etc. In other embodiments, DART™ diabody molecules comprising Fc domains may be tetramers. Such tetramers comprise two 'heavier' polypeptide chains, i.e., a polypeptide chain comprising a VL, a VH and an Fc domain, and two 'lighter' polypeptide chains, i.e., polypeptide chain comprising a VL and a VH. The lighter and heavier chains interact to form a monomer, and said monomers interact via their unpaired Fc domains to form an Ig-like molecule. Such an Ig-like DART™ diabody is tetravalent and may be monospecific, bispecific or tetraspecific.

VI. Therapeutic Methods of Using the Anti-CD3 Antibodies of the Present invention The anti-CD3 antibodies of the present invention and their antigen-binding fragments have particular utility in the treatment of cancers associated with CD3 expression and in the treatment of autoimmune disease and other inflammatory disorders.

These uses can involve the formation of a complex between CD3 and an antibody that binds specifically to CD3. Examples of such antibodies include but are not limited to anti-CD3 monoclonal antibodies mAb1 and mAb2 or, more preferably, their humanized derivatives. The formation of such a complex can be in vitro or in vivo. Without being bound by theory, anti-CD3 antibody can bind to CD3 through the extracellular domain of CD3 and may then be internalized inside of a living normal or cancer cell.

A. Treatment of Cancer

The antibodies and antigen-binding fragments of the present invention bind to CD3 present on the surface of T cells. The antigen-binding fragments of the present invention can be used in the context of a bi-specific (or trispecific or multispecific) molecule, such as a DART or BiTE molecule, to redirect T-cells to a tumor cell. The T-cell can then kill the tumor cell. The bispecific (or trispecific or multispecific) molecules of the present invention are capable of binding to both human CD3 and the CD3 of a non-human mammal (e.g., cynomolgus monkey), and also to a second (or additional) and different antigen(s) or epitope(s). The second antigen or epitope is preferably a tumor antigen expressed on a tumor cell. Such tumor cells may be from cancers, for example, breast cancer, prostate cancer, gastric cancer, lung cancer, stomach cancer, colon cancer, rectal cancer, pancreatic cancer, liver cancer, ovarian cancer, oral cavity cancer, pharyngeal cancer, esophageal cancer, laryngeal cancer, bone cancer, skin cancer, melanoma, uterine cancer, testicular cancer, bladder cancer, kidney cancer, brain cancer, gleoblastoma, thyroid cancer, lymphoma, myeloma, and leukemia. Such The additional antigens or epitopes are preferably cell surface tumor antigens or epitopes (such as: 17-1A, A33, adult erythrocyte primary endoderm I antigen, alpha fetoprotein, an envelope antigen of an RNA tumor virus, bladder tumor oncofetal antigen, B7-H1, B7-H2, B7-H3, B7-H4, B7-H5, B7-H6, Burkitt's lymphoma antigen-38.13, CA125, CD18, CD19, human B-lymphoma antigen-CD20, CD22, CD33, CD44, CD52, CEA, C017-1A, CTA-1, CTLA-4, epidermal growth factor receptor, Ep-CAM, EphA2, fetal erythrocyte I antigen, fibrosarcoma antigen, ganglioside GD2, ganglioside GD3, ganglioside GM2, ganglioside GM3, GICA 19-9, gp IIIb/IIIa, gp72, HER1, HER-2/neu, HER3, HER4, high molecular weight melanoma antigen, HLA-DR antigen, human leukemia T cell antigen-Gp37, human lung carcinoma antigen L20, human lung carcinoma antigen L6, human milk fat globule antigen, IgE, KS ¼ pan-carcinoma antigen, LEA, lung adenocarcinoma F3 antigen, malignant human lymphocyte antigen-APO-1, melanoma antigen gp75, melanoma-associated antigen p97, neoglycoprotein, nuC242, polymorphic epithelial mucin antigen, prostate specific antigen, prostate specific membrane antigen, prostatic acid phosphate, SK-1 antigen, TAG-72, T-antigen, tumor antigen CA125, tumor antigen MUC1, tumor-specific transplantation type of cell-surface antigen, vascular endothelial growth factor, vascular endothelial growth factor-receptor, and αvβ3). Alternatively, such additional antigens or epitopes may be associated with a pathogen (such as: hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), viral miningitis, viral encephalitis, dengue, small pox; mycobacteria rickettsia, mycoplasma, *Neisseria, S. pneumonia, Borrelia burgdorferi, Bacillus anthracis, Streptococcus, Staphylococcus, Mycobacterium*, tetanus, pertissus, cholera, plague, diptheria, chlamydia, and legionella; leishmania, kokzidioa, trypanosoma or malaria; chlamydia and rickettsia.

The antibodies and antigen-binding fragments of the present invention bind to CD3 present on the surface of T cells. Using conventional methods, such antibodies may be labeled with fluorescein, as described above. When such labeled molecules are incubated in the presence of a bispecific molecule (such as for example, a UDART™ diabody having an epitope binding domain that binds to the T-cell receptor and an epitope binding domain that binds to fluorescein ("TCR-UDART™")), they can bind to the fluorescein label and thereby localize themselves to the surface of cells that express CD3 and cause redirected killing of such cells.

In an alternative embodiment, CD19 may be used as the "second" epitope, such that a bispecific antibody, or more preferably, a DART™ diabody, recognizing CD3 and CD19 is employed to eradicate B-cell lymphoma through co-engagement of the B-cell specific antigen (CD19) and the T-cell receptor/CD3 complex on effector T-cells. As disclosed by Moore, P. A. et al. (2011) *"Application Of Dual Affinity Retargeting Molecules To Achieve Optimal Redirected T-Cell Killing Of B-Cell Lymphoma,"* Blood 2011 blood-2010-09-306449, a CD3/CD19 DART™ diabody was used to eradicate B-cell lymphoma through co-engagement of the B-cell specific antigen CD19 and the T-cell receptor/CD3 complex on effector T-cells. Side by side comparison with a single-chain bispecific antibody bearing identical CD19 and CD3 antibody Fv sequences revealed the DART to be more potent in directing B-cell lysis. The enhanced activity with the CD19×CD3 DART was observed on all CD19 expressing B-cell target cells evaluated using resting and pre-stimulated human PBMC or purified effector T-cell populations. Characterization of a CD19×TCR bispecific DART revealed equivalent potency to the CD19×CD3 DART demonstrating flexibility of the DART architecture to support T-cell/B-cell associations for redirected T-cell killing applications. Importantly the enhanced level of killing mediated by DART molecules was unaccompanied with any increase in non-specific T-cell activation or lysis of CD19 negative cells. Cell association studies indicate the DART architecture is well suited for maintaining cell:cell contact apparently contributing to the high level of target cell killing. Finally, the ability of the CD19×TCR DART to inhibit B-cell lymphoma in NOD/SCID mice when co-administered with human PBMC further demonstrates the value of DART molecules for the treatment of B-cell malignancies. The cross-reactive anti-CD3 antibodies of the present invention could be employed in the same way as the CD3 antibodies of Moore, P. A. et al. Thus, the invention provides a therapy for cancers (especially lymphomas and leukemias) involving CD3-expressing cancer cells.

The bispecific (or trispecific or multispecific) molecules of the present invention are preferably administered to a patient in one or more unit doses of typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

B. Treatment of Autoimmune Disease and Inflammation

The invention also provides methods of treating, preventing, slowing the progression of and/or ameliorating the symptoms of T-cell mediated diseases or disorders, including graft rejection, graft versus host disease, unwanted delayed-type hypersensitivity reactions (such as delayed-type allergic reactions), T-cell mediated pulmonary diseases, and autoimmune diseases. T-cell mediated pulmonary diseases include sarcoidosis, hypersensitivity pneumonitis, acute interstitial pneumonitis, alveolitis, pulmonary fibrosis, idiopathic pulmonary fibrosis and other diseases characterized by inflammatory lung damage. T-cell autoimmune diseases include multiple sclerosis, neuritis, polymyositis, psoriasis, vitiligo, Sjogren's syndrome, rheumatoid arthritis, Type 1 diabetes, autoimmune pancreatitis, inflammatory bowel diseases (e.g., Crohn's disease and ulcerative colitis), celiac disease, glomerulonephritis, scleroderma, sarcoidosis, autoimmune thyroid diseases (e.g., Hashimoto's thyroiditis and Graves' disease), myasthenia gravis, Addison's disease, autoimmune uveoretinitis, pemphigus vulgaris, primary biliary cirrhosis, pernicious anemia, and systemic lupus erythematosis, lupus (particularly, cutaneous), effects from organ transplantation, graft vs. host disease (GVHD), etc. Particularly, the methods of the invention are advantageous in subjects with early stage disease to slow or reduce the damage from the autoimmunity and maintain a high level of function and/or reduce the need for other therapy (e.g., in the treatment or prophylaxis of Type I diabetes, the methods of the invention may reduce the need for exogenous insulin administration in the subject). In addition, the methods of the invention may advantageously reduce the incidence of or result in no incidence of cytokine release syndrome previously associated with administration of therapeutic antibodies, and, in particular, anti-T-cell (e.g., anti-CD3 antibody or antigen-binding fragments.

In certain embodiments, the course of treatment with an anti-CD3 antibody or antigen-binding fragments according to the methods of the invention is repeated at 2 month, 4 month, 6 month, 8 month, 9 month, 10 month, 12 month, 15 month, 18 month, 24 month, 30 month, or 36 month intervals. In specific embodiments efficacy of the treatment with an anti-CD3 antibody or antigen-binding fragments of the invention is determined as described herein or as is known in the art at 2 months, 4 months, 6 months, 9 months, 12 months, 15 months, 18 months, 24 months, 30 months, or 36 months subsequent to the previous treatment.

In another embodiment, a subject is administered one or more unit doses of approximately 0.5-50 µg/kg, approximately 0.5-40 µg/kg, approximately 0.5-30 µg/kg, approximately 0.5-20 µg/kg, approximately 0.5-15 µg/kg, approximately 0.5-10 µg/kg, approximately 0.5-5 µg/kg, approximately 1-5 µg/kg, approximately 1-10 µg/kg, approximately 20-40 µg/kg, approximately 20-30 µg/kg, approximately 22-28 µg/kg or approximately 25-26 µg/kg of one or more anti-CD3 antibody or antigen-binding fragments to prevent, treat or ameliorate one or more symptoms of an autoimmune disorder or T cell malignancy. In another embodiment, a subject is administered one or more unit doses of 200 µg/kg, 178 µg/kg, 180 µg/kg, 128 µg/kg, 100 µg/kg, 95 µg/kg, 90 µg/kg, 85 µg/kg, 80 µg/kg, 75 µg/kg, 70 µg/kg, 65 µg/kg, 60 µg/kg, 55 µg/kg, 50 µg/kg, 45 µg/kg, 40 µg/kg, 35 µg/kg, 30 µg/kg, 26 µg/kg, 25 µg/kg, 20 µg/kg, 15 µg/kg, 13 µg/kg, 10 µg/kg, 6.5 µg/kg, 5 µg/kg, 3.2 µg/kg, 3 µg/kg, 2.5 µg/kg, 2 µg/kg, 1.6 µg/kg, 1.5 µg/kg, 1 µg/kg, 0.5 µg/kg, 0.25 µg/kg, 0.1 µg/kg, or 0.05 µg/kg of one or more anti-CD3 antibody or antigen-binding fragments to prevent, treat or ameliorate one or more symptoms of an autoimmune disorder or T-cell malignancy.

In a one embodiment, a subject is administered one or more doses of 200 µg/kg or less, 175 µg/kg or less, 150 µg/kg or less, 128 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, 0.25 µg/kg or less, 0.1 µg/kg or less, or 0.05 µg/kg or less of one or more anti-CD3 antibody or antigen-binding fragments of the invention to prevent, treat or ameliorate one or more symptoms of an autoimmune disorder or T-cell malignancy.

In particular embodiments, a subject is administered one or more doses of about 5-1200 µg/m², preferably, 51-826 µg/m². In another embodiment, a subject is administered one or more unit doses of 1200 µg/m², 1150 µg/m², 1100 µg/m², 1050 µg/m², 1000 µg/m², 950 µg/m², 900 µg/m², 850 µg/m², 800 µg/m², 750 µg/m², 700 µg/m², 650 µg/m², 600 µg/m², 550 µg/m², 500 µg/m², 450 µg/m², 400 µg/m², 350 µg/m², 300 µg/m², 250 µg/m², 200 µg/m², 150 µg/m², 100 µg/m², 50 µg/m², 40 µg/m², 30 µg/m², 20 µg/m², 15 µg/m², 10 µg/m², or 5 µg/m² of one or more anti-CD3 antibody or antigen-binding fragments to prevent, treat, slow the progression of, delay the onset of or ameliorate one or more symptoms of an autoimmune disorder or T-cell malignancy.

In another embodiment, the subject is administered a treatment regimen comprising one or more doses of a prophylactically or therapeutically effective amount of one or more anti-CD3 antibody or antigen-binding fragments, wherein the course of treatment is administered over 2 days, 3 days, 4 days, 5 days, 6 days, 7 days, 8 days, 9 days, 10 days, 11 days, 12 days, 13 days or 14 days. In one embodiment, the treatment regimen comprises administering doses of the prophylactically or therapeutically effective amount of one or more anti-CD3 antibody or antigen-binding fragments every day, every $2^{nd}$ day, every $3^{rd}$ day or every $4^{th}$ day. In certain embodiments, the treatment regimen comprises administering doses of the prophylactically or therapeutically effective amount of one or more anti-CD3 antibody or antigen-binding fragments on Monday, Tuesday, Wednesday, Thursday of a given week and not administering doses of the prophylactically or therapeutically effective amount of one or more anti-CD3 antibody or antigen-binding fragments on Friday, Saturday, and Sunday of the same week until 14 doses, 13, doses, 13 doses, 12 doses, 11 doses, 10 doses, 9 doses, or 8 doses have been administered. In certain embodiments the dose administered is the same each day of the regimen. In certain embodiments, a subject is administered a treatment regimen comprising one or more doses of a prophylactically or therapeutically effective amount of one or more anti-CD3 antibody or antigen-binding fragments, wherein the prophylactically or therapeutically effective amount is 200 µg/kg/day, 175 µg/kg/day, 150 µg/kg/day, 125 µg/kg/day, 100 µg/kg/day, 95 µg/kg/day, 90 µg/kg/day, 85 µg/kg/day, 80 µg/kg/day, 75 µg/kg/day, 70 µg/kg/day, 65 µg/kg/day, 60 µg/kg/day, 55 µg/kg/day, 50 µg/kg/day, 45 µg/kg/day, 40 µg/kg/day, 35 µg/kg/day, 30 µg/kg/day, 26 µg/kg/day, 25 µg/kg/day, 20 µg/kg/day, 15 µg/kg/day, 13 µg/kg/day, 10 µg/kg/day, 6.5 µg/kg/day, 5 µg/kg/day, 3.2 µg/kg/day, 3 µg/kg/day, 2.5 µg/kg/day, 2 µg/kg/day, 1.6 µg/kg/day, 1.5 µg/kg/day, 1 µg/kg/day, 0.5 µg/kg/day, 0.25 µg/kg/day, 0.1 µg/kg/day, or 0.05 µg/kg/day; and/or wherein the prophylactically or therapeutically effective amount is 1200 µg/m²/day, 1150 µg/m²/day, 1100 µg/m²/day, 1050 µg/m²/day, 1000 µg/m²/day, 950 µg/m²/day, 900 µg/m²/day, 850 µg/m²/day, 800 µg/m²/day, 750 µg/m²/day, 700 µg/m²/day, 650 µg/m²/day, 600 µg/m²/day, 550 µg/m²/day, 500 µg/m²/day, 450 µg/m²/day, 400 µg/m²/day, 350 µg/m²/day, 300 µg/m²/day, 250 µg/m²/day, 200 µg/m²/day, 150 µg/m²/day, 100 µg/m²/day, 50 µg/m²/day, 40 µg/m²/day, 30 µg/m²/day, 20 µg/m²/day, 15 µg/m²/day, 10 µg/m²/day, or 5 µg/m²/day. In another embodiment, the intravenous dose of 1200 µg/m² or less, 1150 µg/m² or less, 1100 µg/m² or less, 1050 µg/m² or less, 1000 µg/m² or less, 950 µg/m² or less, 900 µg/m² or less, 850 µg/m² or less, 800 µg/m² or less, 750 µg/m² or less, 700 µg/m² or less, 650 µg/m² or less, 600 µg/m² or less, 550 µg/m² or less, 500 µg/m² or less, 450 µg/m² or less, 400 µg/m² or less, 350 µg/m² or less, 300 µg/m² or less, 250 µg/m² or less, 200 µg/m² or less, 150 µg/m² or less, 100 µg/m² or less, 50 µg/m² or less, 40 µg/m² or less, 30 µg/m² or less, 20 µg/m² or less, 15 µg/m² or less, 10 µg/m² or less, or 5 µg/m² or less of one or more anti-CD3 antibody or antigen-binding fragments is administered over about 24 hours, about 22 hours, about 20 hours, about 18 hours, about 16 hours, about 14 hours, about 12 hours, about 10 hours, about 8 hours, about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to prevent, treat or ameliorate one or more symptoms of an autoimmune disease or T-cell malignancy. The total dosage over the duration of the regimen is preferably a total of less than 9000 µg/m², 8000 µg/m², 7000 µg/m², 6000 µg/m², and may be less than 5000 µg/m², 4000 µg/m², 3000 µg/m², 2000 µg/m², or 1000 µg/m². In specific embodiments, the total dosage administered in the regimen is 100 µg/m² to 200 µg/m², 100 µg/m² to 500 µg/m², 100 µg/m² to 1000 µg/m², or 500 µg/m² to 1000 µg/m².

In preferred embodiments, the dose escalates over the first fourth, first half or first ⅔ of the doses (e.g., over the first 2, 3, 4, 5, or 6 days of a 10, 12, 14, 16, 18 or 20 day regimen of one dose per day) of the treatment regimen until the daily prophylactically or therapeutically effective amount of one or more anti-CD3 antibody or antigen-binding fragments is achieved. In certain embodiments, a subject is administered a treatment regimen comprising one or more doses of a prophylactically or therapeutically effective amount of one or more anti-CD3 antibody or antigen-binding fragments, wherein the prophylactically or therapeutically effective amount is increased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, or 125 µg/kg each day; or increased by, e.g., 1 µg/m², 5 µg/m², 10 µg/m², 15 µg/m², 20 µg/m², 30 µg/m², 40 µg/m², 50 µg/m², 60 µg/m², 70 µg/m², 80 µg/m², 90 µg/m², 100 µg/m², 150 µg/m², 200 µg/m², 250 µg/m², 300 µg/m², 350 µg/m², 400 µg/m², 450 µg/m², 500 µg/m², 550 µg/m², 600 µg/m², or 650 µg/m², each day as treatment progresses. In certain embodiments, a subject is administered a treatment regimen comprising one or more doses of a prophylactically or therapeutically effective amount of one or more anti-CD3 antibody or antigen-binding fragments, wherein the prophylactically or therapeutically effective amount is increased by a factor of 1.25, a factor of 1.5, a factor of 2, a factor of 2.25, a factor of 2.5, or a factor of 5 until the daily prophylactically or therapeutically effective amount of one or more anti-CD3 antibody or antigen-binding fragments is achieved.

In a specific embodiment, a subject is intramuscularly administered one or more doses of a 200 µg/kg or less, preferably 175 µg/kg or less, 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of one or more anti-CD3 antibody or antigen-binding fragments to prevent, treat or ameliorate one or more symptoms of an autoimmune disorder or T-cell malignancy.

In another embodiment, a subject is subcutaneously administered one or more doses of a 200 µg/kg or less, preferably 175 µg/kg or less, 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of one or more anti-CD3 antibody or antigen-binding fragments to prevent, treat or ameliorate one or more symptoms of an autoimmune disorder.

In another embodiment, a subject is intravenously administered one or more doses of a 100 µg/kg or less, preferably 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of one or more anti-CD3 antibody or antigen-binding fragments to prevent, treat or ameliorate one or more symptoms of an autoimmune disorder or T-cell malignancy. In another embodiment, the intravenous dose of 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of one or more anti-CD3 antibody or antigen-binding fragments is administered over about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to prevent, treat or ameliorate one or more symptoms of an autoimmune disorder or T-cell malignancy.

In specific embodiments in which escalating doses are administered for the first days of the dosing regimen, the dose on day 1 of the regimen is 5-100 µg/m$^2$/day, and escalates to the daily dose as recited immediately above by day 3, 4, 5, 6 or 7. For example, on day 1, the subject is administered a dose of approximately 51 µg/m$^2$/day, on day 2 approximately 103 µg/m$^2$/day, on day 3 approximately 207 µg/m$^2$/day, on day 4 approximately 413 µg/m$^2$/day and on subsequent days of the regimen (e.g., days 5-14) 826 µg/m$^2$/day.

In other embodiments, the initial dose is ¼, to ½, to equal to the daily dose at the end of the regimen but is administered in portions at intervals of 6, 8, 10 on 12 hours. For example, a 13 µg/kg/day dose is administered in four doses of 3-4 µg/kg at intervals of 6 hours to reduce the level of cytokine release caused by administration of the antibody.

In specific embodiments, to reduce the possibility of cytokine release and other adverse effects, the first 1, 2, 3, or 4 doses or all the doses in the regimen are administered more slowly by intravenous administration. For example, a dose of 51 µg/m$^2$/day may be administered over about 5 minutes, about 15 minutes, about 30 minutes, about 45 minutes, about 1 hour, about 2 hours, about 4 hours, about 6 hours, about 8 hours, about 10 hours, about 12 hours, about 14 hours, about 16 hours, about 18 hours, about 20 hours, and about 22 hours. In certain embodiments, the dose is administered by slow infusion over a period of, e.g., 20 to 24 hours. In specific embodiments, the dose is infused in a pump, preferably increasing the concentration of antibody administered as the infusion progresses.

In other embodiments, a set fraction of the regimen may be administered in escalating doses. For example, for the 51 µg/m$^2$/day to 826 µg/m$^2$/day regimen described above, the fraction may be ⅒, ¼, ⅓, ½, ⅔ or ¾ of the daily doses. Accordingly, when the fraction is ⅒, the daily doses will be 5.1 µg/m$^2$ on day 1, 10.3 µg/m$^2$ on day 2, 20.7 µg/m$^2$ on day 3, 41.3 µg/m$^2$ on day 4 and 82.6 µg/m$^2$ on days 5 to 14. When the fraction is ¼, the doses will be 12.75 µg/m$^2$ on day 1, 25.5 µg/m$^2$ on day 2, 51 µg/m$^2$ on day 3, 103 µg/m$^2$ on day 4, and 207 µg/m$^2$ on days 5 to 14. When the fraction is ⅓, the doses will be 17 µg/m$^2$ on day 1, 34.3 µg/m$^2$ on day 2, 69 µg/m$^2$ on day 3, 137.6 µg/m$^2$ on day 4, and 275.3 µg/m$^2$ on days 5 to 14. When the fraction is ½, the doses will be 25.5 µg/m$^2$ on day 1, 51 µg/m$^2$ on day 2, 103 µg/m$^2$ on day 3, 207 µg/m$^2$ on day 4, and 413 µg/m$^2$ on days 5 to 14. When the fraction is ⅔, the doses will be 34 µg/m$^2$ on day 1, 69 µg/m$^2$ on day 2, 137.6 µg/m$^2$ on day 3, 275.3 µg/m$^2$ on day 4, and 550.1 µg/m$^2$ on days 5 to 14. When the fraction is ¾, the doses will be 38.3 µg/m$^2$ on day 1, 77.3 µg/m$^2$ on day 2, 155.3 µg/m$^2$ on day 3, 309.8 µg/m$^2$ on day 4, and 620 µg/m$^2$ on days 5 to 14.

In specific embodiments, the anti-CD3 antibody or antigen-binding fragments is not administered by daily doses over a number of days, but is rather administered by infusion in an uninterrupted manner over 4 hours, 6 hours, 8 hours, 10 hours, 12 hours, 15 hours, 18 hours, 20 hours, 24 hours, 30 hours or 36 hours. The infusion may be constant or may start out at a lower dosage for, for example, the first 1, 2, 3, 5, 6, or 8 hours of the infusion and then increase to a higher dosage thereafter. Over the course of the infusion, the patient receives a dose equal to the amount administered in the exemplary regimens set forth above. For example, a dose of approximately 150 µg/m$^2$, 200 µg/m$^2$, 250 µg/m$^2$, 500 µg/m$^2$, 750 µg/m$^2$, 1000 µg/m$^2$, 1500 µg/m$^2$, 2000 µg/m$^2$, 3000 µg/m$^2$, 4000 µg/m$^2$, 5000 µg/m$^2$, 6000 µg/m$^2$, 7000 µg/m$^2$, 8000 µg/m$^2$, or 9000 µg/m$^2$. In particular, the speed and duration of the infusion is designed to minimize the level of free anti-CD3 antibody or antigen-binding fragments in the subject after administration. In certain embodiments, the level of free anti-CD3 antibody or antigen-binding fragments should not exceed 200 ng/ml free antibody. In addition, the infusion is designed to achieve a combined T cell receptor coating and modulation of at least 50%, 60%, 70%, 80%, 90%, 95% or of 100%.

In certain embodiments, the anti-CD3 antibody or antigen-binding fragments is administered so as to achieve a certain level of combined coating and modulation of T cell receptor complexes on T cells, as determined by methods well known in the art, see, e.g., Example 11 of U.S. patent application publication US 2003/0108548, which is hereby incorporated by reference in its entirety. In specific embodiments, the dosing regimen achieves a combined T cell receptor coating and modulation of at least 50%, 60%, 70%, 80%, 90%, 95% or of 100% with, in specific embodiments, little to no free anti-CD3 antibody or antigen-binding fragments detected (for example, less than 200 ng/mL of the drug is detected in the blood of the patient).

In preferred embodiments, the anti-CD3 antibody or antigen-binding fragments are administered parenterally, for example, intravenously, intramuscularly or subcutaneously, or, alternatively, are administered orally. The anti-CD3 antibody or antigen-binding fragments may also be administered as a sustained release formulation.

In a specific embodiment, the administration of one or more doses or a dosage regimen of a prophylactically or therapeutically effective amount of one or more anti-CD3 antibody or antigen-binding fragments does not induce or reduces relative to other immunosuppressive agents one or more of the following unwanted or adverse effects: vital sign abnormalities (fever, tachycardia, bardycardia, hypertension, hypotension), hematological events (anemia, lymphopenia, leukopenia, thrombocytopenia), headache, chills, dizziness, nausea, asthenia, back pain, chest pain (chest pressure), diarrhea, myalgia, pain, pruritus, psoriasis, rhinitis, sweating, injection site reaction, vasodilatation, an increased risk of opportunistic infection, activation of Epstein Barr Virus, apoptosis of T cells and an increased risk of developing certain types of cancer. In another specific embodiment, the administration of one or more doses of a prophylactically or therapeutically effective amount of one or more anti-CD3 antibody or antigen-binding fragments does not induce or reduces relative to other immunosuppressive agents one or more of the following unwanted or adverse effects: vital sign abnormalities (fever, tachycardia, bardycardia, hypertension, hypotension), hematological events (anemia, lymphopenia, leukopenia, thrombocytopenia), headache, chills, dizziness, nausea, asthenia, back pain, chest pain (chest pressure), diarrhea, myalgia, pain, pruritus, psoriasis, rhinitis, sweating, injection site reaction, vasodilatation, an increased risk of opportunistic infection, Epstein Barr Virus activation, apoptosis of T cells, and an increased risk of developing certain types of cancer.

In accordance with the invention, the dose or dosage regimen comprising a prophylactically or therapeutically effective amount of one or more anti-CD3 antibody or antigen-binding fragments for the treatment of an autoimmune disorder may be repeated at 1 month, 2 months, 4 months, 6 months, 8 months, 12 months, 15 months, 18 months or 24 months or longer after the initial or previous dose or dosage regimen comprising a prophylactically or therapeutically effective amount of one or more anti-CD3 antibody or antigen-binding fragments. The repeat dose or dosage regimen may be administered as a matter of course, when symptoms associated with said autoimmune disorder recur after an improvement following the initial or previous dose or dosage regimen, or when symptoms associated with said autoimmune disorder do not improve after the initial dose or dosage regimen of anti-CD3 antibody or antigen-binding fragments according to methods of the invention. For example, with respect to diabetes, a repeat dose or dosage regimen comprising a prophylactically or therapeutically effective amount of one or more anti-CD3 antibody or antigen-binding fragments may be administered to a subject when, for example, the subject's average daily insulin use at 1 month, 2 months, 4 months, 6 months, 8 months, 12 months, 15 months, 18 months or 24 months or longer after initial or previous treatment with anti-CD3 antibody or antigen-binding fragments does not decrease by at least 5%, at least 10%, at least 20%, at least 30%, at least 40%, at least 50%, at least 60%, at least 70%, at least 80% or at least 90% compared to pre-treatment levels. Alternatively, with respect to diabetes, a repeat dose or a dosage regimen comprising a prophylactically or therapeutically effective amount of one or more anti-CD3 antibody or antigen-binding fragments may be administered to a subject when, for example, the subject's HA 1 or HA 1 C levels at 1 month, 2 months, 4 months, 6 months, 8 months, 12 months, 15 months, 18 months or 24 months or longer after initial or previous treatment with anti-CD3 antibody or antigen-binding fragments do not decrease by at least 5%, at least 10%, at least 20%, at least 30%, at least 40%, at least 50%, at least 60%, at least 70%, at least 80% or at least 90% compared to pre-treatment levels. In another embodiment, with respect to diabetes, a repeat dose or dosage regimen comprising a prophylactically or therapeutically effective amount of one or more anti-CD3 antibody or antigen-binding fragments may be administered to a subject when, for example, the subject's C-peptide response at 1 month, 2 months, 4 months, 6 months, 8 months, 12 months, 15 months, 18 months or 24 months or longer after initial or previous treatment with anti-CD3 antibody or antigen-binding fragments decreases by more than 5%, more than 10%, more than 20%, more than 30%, more than 40%, more than 50%, more than 60%, more than 70%, more than 80% or more than 90% compared to pre-treatment levels.

Autoimmune diseases are non-infectious immunological diseases caused by immune responses that are directed to normal components of human cells, tissues and organs. Autoimmune diseases are often chronic diseases that gradually erode targeted tissues and organs. Common diseases now classified as autoimmune diseases due to the presence of inappropriate autoimmune responses include type I insulin-dependent diabetes, rheumatoid arthritis (RA), systemic lupus erythematosus (SLE), multiple sclerosis (MS), inflammatory bowel disease (IBD); myasthenia gravis, celiac's disease, Sjogren's syndrome, Grave's disease, Crohn's disease, autoimmune hepatitis, psoriasis, psoriatic arthritis, asthma, allergic rhinitis, effects from organ transplantation, or graft vs. host disease (GVHD) and numerous other diseases involving an inflammatory immune response.

Because autoimmune diseases are typically chronic, they generally require lifelong treatment and monitoring. Conventional therapies for autoimmune disease are therefore primarily directed to managing the consequences of inflammation caused by the disease, and only a few autoimmune diseases can be cured or made to disappear with such treatment. For some autoimmune diseases, administering one of a limited number of immunosuppressive medications may result in periods of remission or disappearance of active disease. Immunosuppressive agents used for adjunct therapy include substances that suppress cytokine production, down-regulate or suppress self-antigen expression or mask major histocompatibility (MHC) antigens. Immunosuppressive medications include anti-inflammatory drugs (e.g., a nonsteroidal anti-inflammatory drug ("NSAID"), cyclophosphamide, bromocryptine cyclosporine A, methotrexate, steroids such as glucocorticosteroids and cytokines or cytokine receptor antagonists. Patients are rarely able to discontinue these immunosuppressive medications as their autoimmune disease usually reappears when medication is discontinued. Autoimmune disease may become refractive to treatment when immunosuppressive medications are continued long term and may require ever increasing doses of immunosuppressive agents.

Therapeutic antibodies directed to CD3 are believed to produce fewer long-term side effects than many of the immunosuppressive chemotherapies that are presently available for autoimmune diseases (WO 2007/117600). However, prior antibody based therapies have been found to be problematic, particularly where repeated administration was employed. Anti-lymphocyte therapies, such as antilymphocyte globulin (ALG), and monoclonal antibodies directed to B cells, such as rituximab (Rituxin®) and alemtuzumab (CAMPATH®) reduce circulating and tissue B cell populations in treated subjects. However, these therapies also cause severe immunosuppression, which is undesirable for the long term treatment of a chronic autoimmune disease. The principal complication of severe immune-suppressive therapy is infection. Systemic immunosuppression can also be accompanied by undesirable toxic effects and a reduction in levels of hemopoietic stem cells. In addition, patients receiving antibody therapies often develop significant levels of human anti-mouse antibodies (HAMA), human anti-chimeric antibodies (HACA) and anti-idiotypic responses, which may limit repeated treatments when a remission ends.

As discussed above, antibodies directed to antigens of the T cell, such as the T-cell receptor complex (TCR), have been suggested as possible therapeutics for the immunosuppression of autoimmune disease. Anti-CD3 antibodies are believed to induce such immunosuppression by reducing pathogenic T cells and inducing regulatory T cells (WO 2007/117600; St. Clair E. W. (2009) "*Novel Targeted Therapies for Autoimmunity*," Curr. Opin. Immunol. 21(6):648-657; Ludvigsson, J. (2009) "*The Role of Immunomodulation Therapy in Autoimmune Diabetes*," J. Diabetes Sci. Technol. 3(2):320-330). Anti-T cell antibodies, including anti-CD3, have therefore been used to influence immunological status in a subject by suppressing, enhancing or redirecting T cell responses to an antigen. In particular, Teplizumab, also known as hOKT3γ1(Ala-Ala) (containing an alanine at positions 234 and 235) (MacroGenics, Inc.) is an anti-CD3 antibody that had been engineered to alter the function of the T lymphocytes that mediate the destruction of the insulin-producing beta cells of the islets of the pancreas. Teplizumab binds to an epitope of the CD3ε chain expressed on mature T cells and by doing so.

Due in part to their cross-reactivity with non-human CD3 (which permits more accurate and responsive dosing), the anti-CD3 antibodies of the present invention are considered to have particular utility in the treatment of autoimmune disease notwithstanding the apparent failures of the prior art.

Such antibodies and their antigen binding fragments may be used alone or in conjunction with other pharmacological agents. In particular, the present invention contemplates therapies involving the administration of such antibodies or antigen binding fragments in conjunction with anti-B cell antibodies (or antigen-binding fragments thereof). Anti-B cell antibodies are known in the art (see, WO 2007/117600; WO 2005/000901; WO 2004/035607; U.S. Pat. Nos. 5,500, 362 and 5,736,137; U.S. Patent Publications Nos. 2003/0219433; 2005/0271658; 2005/0271658; 2005/0281817; 2006/024295; 2006/024300 and 2006/034835; Clark, E. A. et al. (1985) "*Role Of The Bp35 Cell Surface Polypeptide In Human B-Cell Activation*," Proc. Natl. Acad. Sci. (USA) 82(6):1766-1770; Press, O. W. et al. (1987) "*Monoclonal Antibody IF5 (Anti-CD20) Serotherapy of Human B Cell Lymphomas*," Blood 69:584-591). Such conjunctive administration may be accomplished using joint administration of distinct antibodies or antigen-binding fragments thereof, or by forming bispecific antibodies, or more preferably, by forming DART™ diabodies, as described above, having the ability to bind to both CD3 and a B cell antigen.

Preferably the employed anti-B cell antibody or antigen-binding fragment will be directed to a B cell surface marker, such as a marker selected from CD19, CD20, CD22, CD23, CD32B, CD40, B7-1 (CD80), B7-2 (CD86), CD79a, CD79b, CD38, CD27, a lymphocyte function-associated antigen (LFA), such as LFA-I or LFA-3, CFA-I, or another accessory molecule involved in the T cell, B cell association that leads to T cell and B cell activation in an adaptive immune response. In a further preferred embodiment, the anti-B cell antibody may be a B cell depleting antibody, such as an antibody directed to a marker selected from CD19, CD20, CD22, CD23, CD32B, CD40, B7-1 (CD80), B7-2 (CD86), a lymphocyte function-associated antigen (LFA), such as LFA-I or LFA-3, CFA-I, or an accessory molecule involved in the T cell, B cell association.

Alternatively, such combination therapy may comprise administration of an anti-CD3 antibody or antigen-binding fragment thereof, in combination with an antibody (or antigen-binding fragment thereof) that recognizes an antigen present on an antigen presenting cell (e.g., B7-H3). In a still further preferred embodiment, the combination therapy comprises administration of an anti-CD3 antibody (or antigen-binding fragment thereof) in combination with an antibody (or antigen-binding fragment thereof) that recognizes a polypeptide involved in B cell activation (either directly or indirectly) or an immunomodulator such as a member of TNF cytokine family, or an interferon (e.g., α, β or γ interferon). As is understood by those of skill in the art, such interferons are involved in the regulation of proteins that work together in antigen processing and presentation. These cytokines stimulate cells to increase their expression of HLA class I heavy chains. In one preferred embodiment, the combination therapy comprises administering to a subject having active autoimmune disease an antibody to a T cell antigen in combination with an antibody to β-interferon. In a further preferred embodiment, the combination therapy comprises administering to a subject an antibody targeted to a T cell antigen in combination with an antibody selected from β-interferon antibodies AVONEX®, BETASERON® and REBIF®. In a further embodiment, the combination therapy comprises administering to a subject an antibody targeted to a T cell antigen in combination with an antibody targeted to β-interferon for treatment of a subject having multiple sclerosis.

In a further embodiment, the anti-CD3 antibody may be a non-mitogenic antibody or a reduced-mitogenic antibody that inhibits or prevents T cell activation when a T cell comes in contact with its specific antigen on an antigen presenting cell, in particular an antigen presenting B cell. As used herein, the term "non-mitogenic T cell antibody" means an antibody that is engineered by altering the Fc receptor of the antibody such that it does not trigger the initial activation events and ensuing release of cytokines that are seen when a T cell is activated. A "reduced mitogenic T cell antibody" is an antibody specific for a T cell antigen that reduces the initial activation events and release of cytokines that occur when a T cell is activated. The non-mitogenic or reduced mitogenic antibody may be useful for preventing initial "first dose side effects" seen when an anti-lymphocyte antibody is administered to patient. The non-mitogenic or reduced mitogenic antibody may be an engineered antibody having a modified Fc fragment that prevents or inhibits binding by effector cells.

C. Methods of Administration

In one aspect, embodiments of the present invention provide treated human subjects so as to achieve and maintain clinical remissions for longer periods than remissions achieved by subjects treated with a conventional therapy. For example, where a conventional therapy achieves a remission of symptoms of an autoimmune disease for three months, the compositions of the present invention may provide a complete remission of symptoms of up to six months, up to 12 months and in some cases up to one to two years or longer. It is contemplated that for certain autoimmune diseases it may be possible to provide a complete remission that does not relapse, particularly where therapy begins shortly after the autoimmune disease is diagnosed.

The clinical remission achieved with the combination therapy may be a complete remission, or it may be a partial remission in which significant reductions in disease symptoms are maintained for an extended period. For example, a subject receiving the therapy of the present invention may have reduced autoimmune responses as determined by reduced levels of detectable autoantibodies in body fluids and tissues, for example in cerebrospinal fluid (CSF), serum, urine or in body tissues. A subject receiving the combination therapy also may have reduced T cell responses to autoantigens as detected by in vitro by proliferation or cytokine production assays using peripherial blood mononuclear cells (PBMCs) or purified T cells when compared with subjects treated with a conventional therapy.

The compositions of the present invention may be administered by any suitable means, including parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. In addition, the antibody may suitably be administered by pulse infusion, e.g., with increasing doses of the antibody. Preferably, the dosing is given intravenously or subcutaneously, and more preferably by intravenous infusion(s). Each exposure may be provided using the same or a different administration means. In one embodiment, each exposure is by intravenous administration. In another embodiment, each exposure is given by subcutaneous administration. In yet another embodiment, the exposures are given by both intravenous and subcutaneous administration.

In one embodiment, the therapeutic antibodies are administered as a slow intravenous infusion which may commence at a rate hour to deliver the molecules of the invention in approximately 15 minutes to 4 hours. However, if the subject is experiencing an infusion-related reaction, the infusion rate is preferably reduced, e.g., to half the current rate. The treated subjects may receive a prophylactic treatment of acetaminophen/paracetamol (e.g., about Ig) and diphenhydramine HCl (e.g., about 50 mg or equivalent dose of similar agent) by mouth about 30 to 60 minutes prior to the start of an infusion.

The therapy provided by combination compositions of the present invention (including DART™ diabodies) may be administered to a subject using an initial dose of first antibody that is less than the amount of such antibody needed to achieve a clinical response in therapy for an autoimmune disease when administered as a single antibody therapy. A dose of a therapeutic anti-T cell antibody that is less than the dose needed to achieve depletion of T cells that are able to recognize and respond to autoantigens in a therapy providing a single antibody may be sufficient to provide a desired clinical response. Methods for determining the dosage of a therapeutic antibody needed to achieve a clinical response are known to those of skill in the art. For example, a clinical response in the subject may be measured as time to disease progression, reduction of clinical symptoms, reduction in levels of laboratory markers, reduction in the need for retreatment, or by any other clinical means recognized as a useful indicator of improvement in status of the autoimmune disease.

The second antibody of a combination therapy may also be administered to a subject in need of treatment as an initial dose that is less than an effective dose for achieving a clinical response when the antibody is administered alone. For example, doses of a depleting anti-B cell antibody that achieve less than 100% B-cell depletion, less than 50% B cell depletion, less that 30% depletion or even no B cell depletion may be administered together with a first anti-T cell antibody to achieve a clinical response that provides suppression of an immune response to an autoantigen equal to, or better than the clinical response achieved by administering an amount of a B cell depleting antibody that provides 100% depletion of B cells in the subject when administered alone.

In some instances, clinical response may be a response that neither the first nor the second antibody achieves when administered alone. In other instances, the clinical response may be equivalent to that achieved by administration of a single antibody therapy, where the combination therapy provides less immunosuppression of a treated subject's immune system than a single antibody therapy. In one preferred embodiment, the synergistic response provided by the combination therapy reduces or eliminates a subject's response to an autoantigen while providing lower levels of immunosuppression. General immunosuppression is a significant problem for previously available antibody therapies.

D. Pharmaceutical Formulations

Therapeutic formulations of the antibodies used in embodiments of the present invention are prepared for storage, shipment and administration by mixing a composition of the present invention having a desired purity with optional pharmaceutically acceptable carriers, excipients or stabilizers recognized in the pharmaceutical art in the form of lyophilized formulations or aqueous solutions.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of humanized antibodies of the invention and a pharmaceutically acceptable carrier.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. Pharmaceutical compositions suitable for injection include sterile aqueous solutions where the active agents are water soluble, or dispersions or sterile powders for extemporaneous preparation of sterile injectable solutions. Compositions for use in the combination therapy may be prepared by incorporating the active antagonist or antibody in the required amount with appropriate carriers, for example water, ethanol, polyol (e.g., glycerol, propylene glycol and liquid polyethylene glycol) and suitable mixtures thereof. Isotonic agents such as sugars, polyalcohols such as mannitol, sorbitol or sodium chloride may be included in the composition.

The compositions of the invention can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

E. Kits

The invention provides a pharmaceutical pack or kit comprising one or more containers filled with humanized antibodies of the invention. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more humanized antibodies of the invention. In another embodiment, a kit further comprises one or more other prophylactic or therapeutic agents useful for the treatment of cancer, in one or more containers. In another embodiment, a kit further comprises one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

In one embodiment, the present invention provides an article of manufacture containing antibodies to be used for the combined therapy for treatment of autoimmune disease. The article of manufacture comprises a container comprising a first antibody that binds an antigen present on a T cell and a pharmaceutically acceptable carrier, excipient or diluent within the container. The article of manufacture further comprises a second container comprising a second antibody directed to a B cell surface marker and a pharmaceutically acceptable carrier, excipient or diluent and instructions for administering the composition to a subject in need of treatment for autoimmune disease. Where the first and second antibodies are determined to be complementary and to not adversely affect each other, the first and the second antibody may be provided in a single container containing the first and second antibody in appropriate concentrations for administration together with a package insert and instructions for administration.

Containers of the article of manufacture may be of any suitable material that will not react with or otherwise affect the preparation. The article of manufacture may further comprise a second or a third container comprising a pharmaceutically-acceptable diluent buffer, such as bacteriostatic water for injection, phosphate-buffered saline, Ringer's solution and dextrose solution. The article of manufacture may also include other material that may be desired from a commercial and user standpoint including other buffers, diluents, filters, needles and syringes.

VII. Diagnostic Methods Using the Anti-CD3 Antibodies of the Present invention Antibodies to CD3 made by the methods disclosed herein may also be used to identify the presence or absence of cancerous cells, or the level thereof, which are circulating in blood after their release from the cell surface (e.g., soluble CD3). Such circulating antigen may be an intact CD3 antigen, or a fragment thereof that retains the ability to be detected according to the methods taught herein. Such detection may, for example, be effected by FACS analysis using standard methods commonly used in the art.

In a preferred embodiment of the diagnostic methods of this invention, the antibody bears a detectable label. Examples of labels that may be used include a radioactive agent (e.g., Scandium-47, Technetium-99m, Indium-111, Iodine-131, Rhenium-186, Rhenium-188, Samarium-153, Holmium-166, Lutetium-177, Copper-64, Scandium-47, Yttrium-900), an enzyme or a fluorophore, such as phycoerythrin or fluorescein isothiocyanate (also known as fluoroisothiocyanate or FITC).

One method of using the antibodies for diagnosis is in vivo tumor imaging by linking the antibody to a radioactive or radio-opaque agent, administering the antibody to the individual and using an x-ray or other imaging machine to visualize the localization of the labeled antibody at the surface of cancer cells expressing the antigen. The antibody is administered at a concentration that promotes binding at physiological conditions.

In vitro techniques for detection of CD3 are routine in the art and include enzyme linked immunosorbent assays (ELISAs), immunoprecipitations, immunofluorescence, enzyme immunoassay (EIA), radioimmunoassay (RIA), and Western blot analysis.

The invention also provides methods of aiding diagnosis of cancer characterized by cancer cells that express CD3 in an individual using any antibody that binds to CD3 and any other methods that can be used determine the level of CD3 expression. As used herein, methods for "aiding diagnosis" means that these methods assist in making a clinical determination regarding the classification, or nature, of cancer, and may or may not be conclusive with respect to the definitive diagnosis. Accordingly, a method of aiding diagnosis of cancer can comprise the step of detecting the level of CD3 in a biological sample from the individual and/or determining the level of CD3 expression in the sample. Antibodies recognizing the antigen or a portion thereof may also be used to create diagnostic immunoassays for detecting antigen released or secreted from living or dying cancer cells in bodily fluids, including but not limited to, blood, saliva, urine, pulmonary fluid, or ascites fluid. The anti-CD3 antibodies made by the methods disclosed herein may be used to determine whether an individual diagnosed with cancer may be deemed a candidate for immunotherapy using antibodies directed against CD3. In one embodiment, a biopsy sample may be tested for expression of CD3, using antibodies directed against CD3. Individuals with cancer cells that express CD3 are suitable candidates for immunotherapy using antibodies directed against CD3. Staining with anti-CD3 antibody may also be used to distinguish cancerous tissues from normal tissues.

Methods of using anti-CD3 antibodies for diagnostic purposes are useful both before and after any form of anti-cancer treatment, e.g., chemotherapy or radiation therapy, to determine which tumors are most likely to respond to a given treatment, prognosis for individual with cancer, tumor subtype or origin of metastatic disease, and progression of the disease or response to treatment.

The compositions of this invention are particularly suitable for the diagnosis of disease states other than cancer, using the methods generally described above in application with other diseased (non-cancerous) cells. Disease states suitable for use in the methods of this invention include, but are not limited to, diseases or disorders associated with inflammatory or autoimmune responses in individuals. The methods described above may be used for modulating inflammatory or autoimmune responses in individuals. Diseases and conditions resulting from inflammation and autoimmune disorders that may be subject to diagnosis and/or treatment using the compositions and methods of the invention include, by way of illustration and not of limitation, multiple sclerosis, meningitis, encephalitis, stroke, other cerebral traumas, inflammatory bowel disease including ulcerative colitis and Crohn's disease, myasthenia gravis, lupus, rheumatoid arthritis, asthma, acute juvenile onset diabetes, AIDS dementia, atherosclerosis, nephritis, retinitis, atopic dermatitis, psoriasis, myocardial ischemia and acute leukocyte-mediated lung injury.

Still other indications for diagnostic and/or therapeutic use of antibodies and other therapeutic agents of the invention include administration to individuals at risk of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue.

Monoclonal antibodies to CD3 made by the methods disclosed herein may be used to identify the presence or absence of human cancer stem cells in a variety of tissues. Cancer stem cells (CSCs) have been hypothesized to play a role in tumor growth and metastasis (Ghotra, V. P. et al. (2009) "The Cancer Stem Cell Microenvironment And Anti-Cancer Therapy," Int. J. Radiat. Biol. 85(11):955-962; Gupta, P. B. et al. (2009) "Cancer Stem Cells: Mirage Or Reality?" Nat. Med. 15(9):1010-1012; Lawson, J. C. et al. (2009) "Cancer Stem Cells In Breast Cancer And Metastasis," Breast Cancer Res. Treat. 118(2):241-254; Hermann, P. C. et al. (2009) "Pancreatic Cancer Stem Cells—Insights And Perspectives," Expert Opin. Biol. Ther. 9(10):1271-1278; Schatton, T. et al. (2009) "Identification And Targeting Of Cancer Stem Cells," Bioessays 31(10):1038-1049; Mittal, S. et al. (2009) "Cancer Stem Cells: The Other Face Of Janus," Amer. J. Med. Sci. 338(2):107-112; Alison, M. R. et al. (2009) "Stem Cells And Lung Cancer: Future Therapeutic Targets?" Expert Opin. Biol. Ther. 9(9):1127-1141; Charafe-Jauffret, E. et al. (2009) "Breast Cancer Stem Cells: Tools And Models To Rely On," BMC Cancer 9:202; Scopelliti, A. et al. (2009) "Therapeutic Implications Of Cancer Initiating Cells," Expert Opin. Biol. Ther. 9(8):1005-1016; PCT Publication WO 2008/091908). Under this hypothesis, the CSCs provide a small, distinct subset of cells within each tumor that are capable of indefinite self-renewal and of developing into the more adult tumor cell(s) that are relatively limited in replication capacity. It has been hypothesized that these cancer stem cells might be more resistant to chemotherapeutic agents, radiation or other toxic conditions, and thus, persist after clinical therapies and later grow into secondary tumors, metastases or be responsible for relapse. It has been suggested that CSCs can arise either from 'normal' tissue stem cells or from more differentiated tissue progenitor cells.

Uses described in this application that recite their use for anti-CD3 antibodies also encompass the use of other CD3 agonists, antagonists and modulators as described herein for the use of identification and treatment of cancer stem cells. In such embodiments, anti-CD3 antibodies and other CD3 agonists, antagonists and modulators are used for identification, diagnosis or therapeutic treatment of cancer stem cells using similar methods described, and alterations within the scope of the ordinary skilled practitioner are made to tailor the method to the identification/diagnosis or treatment of cancer stem cells.

Having now generally described the invention, the same will be more readily understood through reference to the following examples, which are provided by way of illustration and are not intended to be limiting of the present invention unless specified.

Example 1 mAb1 Binds to Both Human and Cynomolgus Monkey CD3

Figure 1B:
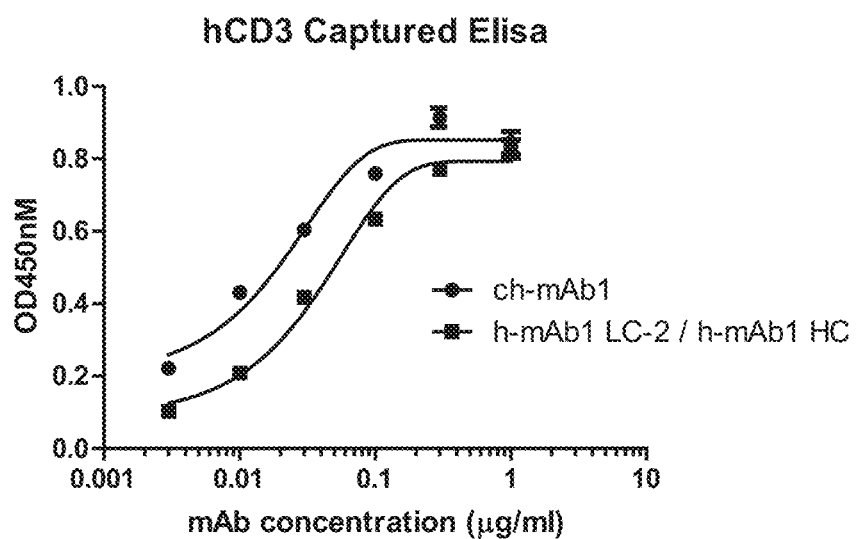

In order to assess the ability of mAb1 to bind to human CD3, a capture ELISA was performed. Plates were coated with 1 µg/ml of soluble cynomolgus CD3 ("sCD3") and incubated in the presence of various concentrations of a chimeric variant of mAb1 antibody (ch-mAb1) (containing the variable sequences of mAb1 and the constant regions of a human antibody), a humanized variant (h-mAb1) and an antibody composed of the light chain of the chimeric mAb1 antibody and the heavy chain of the humanized variant of mAb1. The results of this experiment are shown in FIG. 1A. The experiment shows the ability of mAb1 to bind to the CD3 of a non-human mammalian species. Additionally, the binding of the chimeric mAb1 antibody was compared to that of an antibody composed of the humanized variant mAb1 LC-2 and the heavy chain of mAb1. The results of this experiment are shown in FIG. 1B. The experiment shows the ability of mAb1 to bind to human CD3. FIGS. 1A and 1B thus reveal that the humanized mAb1 was capable of binding to both human CD3 and a CD3 of a non-human mammal. Humanized mAb showed binding to sCD3 and hCD3 that was similar to that of the chimeric mAb1.

Example 2

Humanization of mAb1

Humanized derivatives of mAb1 were prepared. The amino acid sequences and encoding polynucleotide sequences of these humanized derivatives are shown below. The CDRs are shown in boldface and underlined.

Amino Acid Sequence of Humanized mAb1 Variable Light Chain Variant 1 (SEQ ID NO:10):

```
DIQMTQSPSS LSASVGDRVT ITCSASSSVS YMNWYQQKPG

KAPKRLIYDS SKLASGVPSR FSGSGSGTEF TLTISSLQPE

DFATYYCQQW SRNPPTFGGG TKVEIK
```

Polynucleotide Sequence Encoding Humanized mAb1 Variable Light Chain Variant 1 (SEQ ID NO:11):

```
gacatccaga tgacccagtc ccctccagc ctgtccgcct ctgtgggcga cagagtgaca atcacctgtt ccgccagctc ctccgtgtcc tacatgaact ggtatcagca gaagcccggc aaggccccca gcggctgat ctacgactcc tccaagctgg cctccggcgt gccctccaga ttctccggct ctggctccgg caccgagttc accctgacca tctccagcct gcagcccgag gacttcgcca cctactactg ccagcagtgg tcccggaacc cccctacctt cggcggaggc accaaggtgg aaatcaag
```

Amino Acid Sequence of Humanized mAb1 Variable Light Chain Variant 2 (mAb1 LC-2) (SEQ ID NO:12):

```
DVVMTQSPAI MSAFPGEKVT ITCSASSSVS YMNWYQQKPG

KAPKRWIYDS SKLASGVPSR FSGSGSGTEF TLTISSLQPE

DFATYYCQQW SRNPPTFGGG TKVEIK
```

Polynucleotide Sequence Encoding Humanized mAb1 Variable Light Chain Variant 2 (SEQ ID NO:13):

```
gacgtggtga tgacccagtc tcctgccatc atgagtgctt tcccaggcga gaaagtgacc attacatgct ctgcttccag ctctgtgtcc tacatgaact ggtatcagca gaagccaggg aaagcaccca agaggtggat ctacgactcc tccaagctgg cctccggcgt gccaagccgg ttctctggta gtggctcagg aaccgagttt actctgacca tttccagcct gcagcctgaa gatttcgcaa catactattg tcagcagtgg tccagaaatc cccctacatt tggcggaggg actaaagtgg aaatcaag
```

Amino Acid Sequence of Humanized mAb1 Variable Heavy Chain (SEQ ID NO:14):

```
QVQLVQSGAE VKKPGASVKV SCKASGYTFT RSTMHWVRQA

PGQGLEWIGY INPSSAYTNY NQKFKDRVTI TADKSTSTAY

MELSSLRSED TAVYYCASPQ VHYDYNGFPY WGQGTLVTVS S
```

Polynucleotide Sequence Encoding Humanized mAb1 Variable Heavy Chain Chain (SEQ ID NO:15):

```
caggtgcagc tggtgcagtc tggcgccgaa gtgaagaaac ctggcgcctc cgtgaaggtg tcctgcaagg cctccggcta caccttcacc cggtccacca tgcactgggt gcgacaggcc ccaggccagg gactggaatg gatcggctac atcaacccct ccagcgccta caccaactac aaccagaaat tcaaggaccg cgtgaccatc accgccgaca gtccaccag caccgcctac atggaactgt ctagcctgcg gagcgaggac accgccgtgt actactgcgc ctccccccag gtgcactacg actacaacgg cttcccctac tggggccagg gcaccctggt gacagtgtcc tcc
```

Example 3

Humanization of mAb2

Humanized derivatives of mAb2 were prepared. The amino acid sequences and encoding polynucleotide sequences of these humanized derivatives are shown below. The CDRs are shown in boldface and underlined.

Amino Acid Sequence of Humanized mAb2 Variable Light Chain Variant 1 (h-mAb2 VL-1) (SEQ ID NO:16):

```
QAVVTQEPSL TVSPGGTVTL TCRSSTGAVT TSNYANWFQQ

KPGQAPRTLI GGTNKRAPWT PARFSGSLLG GKAALTITGA

QAEDEADYYC ALWYSNLWVF GGGTKLTVLG
```

Polynucleotide Sequence Encoding Humanized mAb2 Variable Light Chain Variant 1 (h-mAb2 VL-1) (SEQ ID NO:17):

```
caggctgtgg tgactcagga gccttcactg accgtgtccc
caggcggaac tgtgaccctg acatgcagat ccagcacagg
cgcagtgacc acatctaact acgccaattg gttccagcag
aagccaggac aggcaccaag gaccctgatc gggggtacaa
acaaaagggc tccctggacc cctgcacggt tttctggaag
tctgctgggc ggaaaggccg ctctgactat taccggggca
caggccgagg acgaagccga ttactattgt gctctgtggt
atagcaatct gtgggtgttc gggggtggca caaaactgac
tgtgctggga
```

Amino Acid Sequence of Humanized mAb2 Variable Light Chain Variant 2 (h-mAb2 VL-2) (SEQ ID NO:18):

```
QAVVTQEPSL TVSPGGTVTL TCRSSTGAVT TSNYANWVQQ
KPGQAPRTLI GGTNKRAPWT PARFSGSLLG GKAALTITGA
QAEDEADYYC ALWYSNLWVF GGGTKLTVLG
```

Polynucleotide Sequence Encoding Humanized mAb2 Variable Light Chain Variant 2 (h-mAb2 VL-2) (SEQ ID NO:19):

```
caggctgtgg tgactcagga gccttcactg accgtgtccc
caggcggaac tgtgaccctg acatgcagat ccagcacagg
cgcagtgacc acatctaact acgccaattg ggtgcagcag
aagccaggac aggcaccaag gaccctgatc gggggtacaa
acaaaagggc tccctggacc cctgcacggt tttctggaag
tctgctgggc ggaaaggccg ctctgactat taccggggca
caggccgagg acgaagccga ttactattgt gctctgtggt
atagcaatct gtgggtgttc gggggtggca caaaactgac
tgtgctggga
```

Amino Acid Sequence of Humanized mAb2 Variable Light Chain Variant 3 (h-mAb2 VL-3) (SEQ ID NO:20):

```
QAVVTQEPSL TVSPGGTVTL TCRSSTGAVT TSNYANWFQE
KPGQAPRTLI GGTNKRAPWT PARFSGSLLG GKAALTITGA
QAEDEADYYC ALWYSNLWVF GGGTKLTVLG
```

Polynucleotide Sequence Encoding Humanized mAb2 Variable Light Chain Variant 3 (h-mAb2 VL-3) (SEQ ID NO:21):

```
caggctgtgg tgactcagga gccttcactg accgtgtccc
caggcggaac tgtgaccctg acatgcagat ccagcacagg
cgcagtgacc acatctaact acgccaattg gttccaggag
aagccaggac aggcaccaag gaccctgatc gggggtacaa
acaaaagggc tccctggacc cctgcacggt tttctggaag
tctgctgggc ggaaaggccg ctctgactat taccggggca
caggccgagg acgaagccga ttactattgt gctctgtggt
atagcaatct gtgggtgttc gggggtggca caaaactgac
tgtgctggga
```

Amino Acid Sequence of Humanized mAb2 Variable Light Chain Variant 4 (h-mAb2 VL-4) (SEQ ID NO:22):

```
QAVVTQEPSL TVSPGGTVTL TCRSSTGAVT TSNYANWFQQ
KPGQAPRGLI GGTNKRAPWT PARFSGSLLG GKAALTITGA
QAEDEADYYC ALWYSNLWVF GGGTKLTVLG
```

Polynucleotide Sequence Encoding Humanized mAb2 Variable Light Chain Variant 4 (h-mAb2 VL-4) (SEQ ID NO:23):

```
caggctgtgg tgactcagga gccttcactg accgtgtccc
caggcggaac tgtgaccctg acatgcagat ccagcacagg
cgcagtgacc acatctaact acgccaattg gttccagcag
aagccaggac aggcaccaag gggcctgatc gggggtacaa
acaaaagggc tccctggacc cctgcacggt tttctggaag
tctgctgggc ggaaaggccg ctctgactat taccggggca
caggccgagg acgaagccga ttactattgt gctctgtggt
atagcaatct gtgggtgttc gggggtggca caaaactgac
tgtgctggga
```

Amino Acid Sequence of Humanized mAb2 Variable Light Chain Variant 5 (h-mAb2 VL-5) (SEQ ID NO:24):

```
QAVVTQEPSL TVSPGGTVTL TCRSSTGAVT TSNYANWVQE
KPGQAPRTLI GGTNKRAPWT PARFSGSLLG GKAALTITGA
QAEDEADYYC ALWYSNLWVF GGGTKLTVLG
```

Polynucleotide Sequence Encoding Humanized mAb2 Variable Light Chain Variant 5 (h-mAb2 VL-5) (SEQ ID NO:25):

```
caggctgtgg tgactcagga gccttcactg accgtgtccc
caggcggaac tgtgaccctg acatgcagat ccagcacagg
cgcagtgacc acatctaact acgccaattg ggtgcaggag
aagccaggac aggcaccaag gaccctgatc gggggtacaa
acaaaagggc tccctggacc cctgcacggt tttctggaag
tctgctgggc ggaaaggccg ctctgactat taccggggca
caggccgagg acgaagccga ttactattgt gctctgtggt
atagcaatct gtgggtgttc gggggtggca caaaactgac
tgtgctggga
```

Amino Acid Sequence of Humanized mAb2 Variable Light Chain Variant 6 (h-mAb2 VL-6) (SEQ ID NO:26):

```
QAVVTQEPSL TVSPGGTVTL TCRSSTGAVT TSNYANWVQQ
KPGQAPRGLI GGTNKRAPWT PARFSGSLLG GKAALTITGA
QAEDEADYYC ALWYSNLWVF GGGTKLTVLG
```

Polynucleotide Sequence Encoding Humanized mAb2 Variable Light Chain Variant 6 (h-mAb2 VL-6) (SEQ ID NO:27):

```
caggctgtgg tgactcagga gccttcactg accgtgtccc
caggcggaac tgtgaccctg acatgcagat ccagcacagg
cgcagtgacc acatctaact acgccaattg ggtgcagcag
aagccaggac aggcaccaag gggcctgatc gggggtacaa
acaaaagggc tccctggacc cctgcacggt tttctggaag
tctgctgggc ggaaaggccg ctctgactat taccggggca
caggccgagg acgaagccga ttactattgt gctctgtggt
atagcaatct gtgggtgttc gggggtggca caaaactgac
tgtgctggga
```

Amino Acid Sequence of Humanized mAb2 Variable Light Chain Variant 7 (h-mAb2 VL-7) (SEQ ID NO:28):

```
QAVVTQEPSL TVSPGGTVTL TCRSSTGAVT TSNYANWFQE
KPGQAPRGLI GGTNKRAPWT PARFSGSLLG GKAALTITGA
QAEDEADYYC ALWYSNLWVF GGGTKLTVLG
```

Polynucleotide Sequence Encoding Humanized mAb2 Variable Light Chain Variant 7 (h-mAb2 VL-7) (SEQ ID NO:29):

```
caggctgtgg tgactcagga gccttcactg accgtgtccc
caggcggaac tgtgaccctg acatgcagat ccagcacagg
cgcagtgacc acatctaact acgccaattg gttccaggag
aagccaggac aggcaccaag gggcctgatc gggggtacaa
acaaaagggc tccctggacc cctgcacggt tttctggaag
tctgctgggc ggaaaggccg ctctgactat taccggggca
caggccgagg acgaagccga ttactattgt gctctgtggt
atagcaatct gtgggtgttc gggggtggca caaaactgac
tgtgctggga
```

Amino Acid Sequence of Humanized mAb2 Variable Light Chain Variant 8 (h-mAb2 VL-8) (SEQ ID NO:30):

```
QAVVTQEPSL TVSPGGTVTL TCRSSTGAVT TSNYANWVQE
KPGQAPRGLI GGTNKRAPWT PARFSGSLLG GKAALTITGA
QAEDEADYYC ALWYSNLWVF GGGTKLTVLG
```

Polynucleotide Sequence Encoding Humanized mAb2 Variable Light Chain Variant 8 (h-mAb2 VL-8) (SEQ ID NO:31):

```
caggctgtgg tgactcagga gccttcactg accgtgtccc
caggcggaac tgtgaccctg acatgcagat ccagcacagg
cgcagtgacc acatctaact acgccaattg ggtgcaggag
aagccaggac aggcaccaag gggcctgatc gggggtacaa
acaaaagggc tccctggacc cctgcacggt tttctggaag
tctgctgggc ggaaaggccg ctctgactat taccggggca
caggccgagg acgaagccga ttactattgt gctctgtggt
atagcaatct gtgggtgttc gggggtggca caaaactgac
tgtgctggga
```

Amino Acid Sequence of Humanized mAb2 Variable Light Chain Variant 9 (h-mAb2 VL-9) (SEQ ID NO:32):

```
QAVVTQEPSL TVSPGGTVTL TCRSSTGAVT TSNYANWVQE
KPGQAFRGLI GGTNKRAPWT PARFSGSLLG GKAALTITGA
QAEDEADYYC ALWYSNLWVF GGGTKLTVLG
```

Polynucleotide Sequence Encoding Humanized mAb2 Variable Light Chain Variant 9 (h-mAb2 VL-9) (SEQ ID NO:33):

```
caggctgtgg tgactcagga gccttcactg accgtgtccc
caggcggaac tgtgaccctg acatgcagat ccagcacagg
cgcagtgacc acatctaact acgccaattg ggtgcaggag
aagccaggac aggcattcag gggcctgatc gggggtacaa
acaaaagggc tccctggacc cctgcacggt tttctggaag
tctgctgggc ggaaaggccg ctctgactat taccggggca
caggccgagg acgaagccga ttactattgt gctctgtggt
atagcaatct gtgggtgttc gggggtggca caaaactgac
tgtgctggga
```

Amino Acid Sequence of Humanized mAb2 Variable Light Chain Variant 10 (h-mAb2 VL-10) (SEQ ID NO:34):

```
QAVVTQEPSL TVSPGGTVTL TCRSSTGAVT TSNYANWFQQ
KPDHLFTGLI GGTNKRAPWT PARFSGSLLG GKAALTITGA
QAEDEADYYC ALWYSNLWVF GGGTKLTVLG
```

Polynucleotide Sequence Encoding Humanized mAb2 Variable Light Chain Variant 10 (h-mAb2 VL-10) (SEQ ID NO:35):

```
caggctgtgg tgactcagga gccttcactg accgtgtccc
caggcggaac tgtgaccctg acatgcagat ccagcactgg
agcagtgact acctctaact acgctaattg gttccagcag
```

-continued
```
aagcccgacc acctgttcac tgggctgatc ggcggaacca acaaaagggc tccctggacc cctgcacggt tttctggaag tctgctgggc ggaaaggccg ctctgactat taccggggca caggccgagg acgaagccga ttactattgt gctctgtggt atagcaatct gtgggtgttc gggggtggca caaaactgac tgtgctggga
```

Amino Acid Sequence of Humanized mAb2 Heavy Chain Variant 1 (h-mAb2 VH-1) (SEQ ID NO:36):

```
EVQLVESGGG LVQPGGSLRL SCAASGFTFS TYAMNWVRQA
PGKGLEWVGR IRSKYNNYAT YYADSVKDRF TISRDDSKNS
LYLQMNSLKT EDTAVYYCAR HGNFGNSYVS WFAYWGQGTL VTVSS
```

Polynucleotide Sequence Encoding Humanized mAb2 Variable Heavy Chain Variant 1 (h-mAb2 VH-1) (SEQ ID NO:37):

```
gaggtgcagc tggtggaaag cggcggagga ctggtgcagc caggtggcag cctgcgactg tcttgcgccg ctagtggctt cacctttct acatacgcca tgaactgggt gaggcaggct cctggaaagg ggctggagtg ggtgggcagg atcaggtcca agtacaacaa ttatgcaacc tactatgccg actcagtgaa ggatagattc acaatttccc gcgacgattc taaaaacagt ctgtatctgc agatgaactc cctgaagact gaagacaccg ccgtgtacta ttgtgcaaga cacggaaact cggcaactc ctacgtgtcc tggtttgcat attggggtca gggcacactg gtgaccgtgt ccagc
```

Amino Acid Sequence of Humanized mAb2 Heavy Chain Variant 2 (h-mAb2 VH-2) (SEQ ID NO:38):

```
EVQLVESGGG LVQPGGSLRL SCAASGFTFN TYAMNWVRQA
PGKGLEWVGR IRSKYNNYAT YYADSVKDRF TISRDDSKNS
LYLQMNSLKT EDTAVYYCAR HGNFGNSYVS WFAYWGQGTL VTVSS
```

Polynucleotide Sequence Encoding Humanized mAb2 Variable Heavy Chain Variant 2 (h-mAb2 VH-2) (SEQ ID NO:39):

```
gaggtgcagc tggtggaaag cggcggagga ctggtgcagc caggtggcag cctgcgactg tcttgcgccg ctagtggctt caccttaac acatacgcca tgaactgggt gaggcaggct cctggaaagg ggctggagtg ggtgggcagg atcaggtcca agtacaacaa ttatgcaacc tactatgccg actcagtgaa ggatagattc acaatttccc gcgacgattc taaaaacagt ctgtatctgc agatgaactc cctgaagact gaagacaccg ccgtgtacta ttgtgcaaga cacggaaact cggcaactc ctacgtgtcc tggtttgcat attggggtca gggcacactg gtgaccgtgt ccagc
```

Amino Acid Sequence of Humanized mAb2 Heavy Chain Variant 3 (h-mAb2 VH-3) (SEQ ID NO:40):

```
EVQLVESGGG LVQPGGSLRL SCAASGFTFS TYAMNWVRQA
PGKGLEWVAR IRSKYNNYAT YYADSVKDRF TISRDDSKNS
LYLQMNSLKT EDTAVYYCAR HGNFGNSYVS WFAYWGQGTL VTVSS
```

Polynucleotide Sequence Encoding Humanized mAb2 Variable Heavy Chain Variant 3 (h-mAb2 VH-3) (SEQ ID NO:41):

```
gaggtgcagc tggtggaaag cggcggagga ctggtgcagc caggtggcag cctgcgactg tcttgcgccg ctagtggctt cacctttct acatacgcca tgaactgggt gaggcaggct cctggaaagg ggctggagtg ggtggccagg atcaggtcca agtacaacaa ttatgcaacc tactatgccg actcagtgaa ggatagattc acaatttccc gcgacgattc taaaaacagt ctgtatctgc agatgaactc cctgaagact gaagacaccg ccgtgtacta ttgtgcaaga cacggaaact cggcaactc ctacgtgtcc tggtttgcat attggggtca gggcacactg gtgaccgtgt ccagc
```

Amino Acid Sequence of Humanized mAb2 Heavy Chain Variant 4 (h-mAb2 VH-4 SE ID NO:42):

```
EVQLVESGGG LVQPGGSLRL SCAASGFTFS TYAMNWVRQA
PGKGLEWVGR IRSKYNNYAT YYADSVKDRF TISRDDSKNS
LYLQMNSLKT EDTAVYYCVR HGNFGNSYVS WFAYWGQGTL VTVSS
```

Polynucleotide Sequence Encoding Humanized mAb2 Variable Heavy Chain Variant 4 (h-mAb2 VH-4) (SEQ ID NO:43):

```
gaggtgcagc tggtggaaag cggcggagga ctggtgcagc caggtggcag cctgcgactg tcttgcgccg ctagtggctt cacctttct acatacgcca tgaactgggt gaggcaggct cctggaaagg ggctggagtg ggtgggcagg atcaggtcca agtacaacaa ttatgcaacc tactatgccg actcagtgaa ggatagattc acaatttccc gcgacgattc taaaaacagt ctgtatctgc agatgaactc cctgaagact gaagacaccg ccgtgtacta ttgtgtgaga cacggaaact cggcaactc ctacgtgtcc tggtttgcat attggggtca gggcacactg gtgaccgtgt ccagc
```

Amino Acid Sequence of Humanized mAb2 Heavy Chain Variant 5 (h-mAb2 VH-5) (SEQ ID NO:44):

```
EVQLVESGGG LVQPGGSLRL SCAASGFTFN TYAMNWVRQA

PGKGLEWVAR IRSKYNNYAT YYADSVKDRF TISRDDSKNS

LYLQMNSLKT EDTAVYYCAR HGNFGNSYVS WFAYWGQGTL

VTVSS
```

Polynucleotide Sequence Encoding Humanized mAb2 Variable Heavy Chain Variant 5 (h-mAb2 VH-5) (SEQ ID NO:45):

```
gaggtgcagc tggtggaaag cggcggagga ctggtgcagc caggtggcag cctgcgactg tcttgcgccg ctagtggctt cacctttaac acatacgcca tgaactgggt gaggcaggct cctggaaagg ggctggagtg ggtggccagg atcaggtcca agtacaacaa ttatgcaacc tactatgccg actcagtgaa ggatagattc acaatttccc gcgacgattc taaaaacagt ctgtatctgc agatgaactc cctgaagact gaagacaccg ccgtgtacta ttgtgcaaga cacggaaact tcggcaactc ctacgtgtcc tggtttgcat attggggtca gggcacactg gtgaccgtgt ccagc
```

Amino Acid Sequence of Humanized mAb2 Heavy Chain Variant 6 (h-mAb2 VH-6) (SEQ ID NO:46):

```
EVQLVESGGG LVQPGGSLRL SCAASGFTFN TYAMNWVRQA

PGKGLEWVGR IRSKYNNYAT YYADSVKDRF TISRDDSKNS

LYLQMNSLKT EDTAVYYCVR HGNFGNSYVS WFAYWGQGTL

VTVSS
```

Polynucleotide Sequence Encoding Humanized mAb2 Variable Heavy Chain Variant 6 (h-mAb2 VH-6) (SEQ ID NO:47):

```
gaggtgcagc tggtggaaag cggcggagga ctggtgcagc caggtggcag cctgcgactg tcttgcgccg ctagtggctt cacctttaac acatacgcca tgaactgggt gaggcaggct cctggaaagg ggctggagtg ggtggcagg atcaggtcca agtacaacaa ttatgcaacc tactatgccg actcagtgaa ggatagattc acaatttccc gcgacgattc taaaaacagt ctgtatctgc agatgaactc cctgaagact gaagacaccg ccgtgtacta ttgtgtgaga cacggaaact tcggcaactc ctacgtgtcc tggtttgcat attggggtca gggcacactg gtgaccgtgt ccagc
```

Amino Acid Sequence of Humanized mAb2 Heavy Chain Variant 7 (h-mAb2 VH-7) (SEQ ID NO:48):

```
EVQLVESGGG LVQPGGSLRL SCAASGFTFS TYAMNWVRQA

PGKGLEWVAR IRSKYNNYAT YYADSVKDRF TISRDDSKNS

LYLQMNSLKT EDTAVYYCVR HGNFGNSYVS WFAYWGQGTL

VTVSS
```

Polynucleotide Sequence Encoding Humanized mAb2 Variable Heavy Chain Variant 7 (h-mAb2 VH-7) (SEQ ID NO:49):

```
gaggtgcagc tggtggaaag cggcggagga ctggtgcagc caggtggcag cctgcgactg tcttgcgccg ctagtggctt cacctttct acatacgcca tgaactgggt gaggcaggct cctggaaagg ggctggagtg ggtggccagg atcaggtcca agtacaacaa ttatgcaacc tactatgccg actcagtgaa ggatagattc acaatttccc gcgacgattc taaaaacagt ctgtatctgc agatgaactc cctgaagact gaagacaccg ccgtgtacta ttgtgtgaga cacggaaact tcggcaactc ctacgtgtcc tggtttgcat attggggtca gggcacactg gtgaccgtgt ccagc
```

Amino Acid Sequence of Humanized mAb2 Heavy Chain Variant 8 (h-mAb2 VH-8) (SEQ ID NO:50):

```
EVQLVESGGG LVQPGGSLRL SCAASGFTFN TYAMNWVRQA

PGKGLEWVAR IRSKYNNYAT YYADSVKDRF TISRDDSKNS

LYLQMNSLKT EDTAVYYCVR HGNFGNSYVS WFAYWGQGTL

VTVSS
```

Polynucleotide Sequence Encoding Humanized mAb2 Variable Heavy Chain Variant 8 (h-mAb2 VH-8) (SEQ ID NO:51):

```
gaggtgcagc tggtggagtc tggggaggc ttggtccagc ctggagggtc cctgagactc tcctgtgcag cctctggatt caccttcaac acatacgcta tgaattgggt ccgccaggct ccaggaaagg ggctggagtg ggttgcaagg atcaggtcca agtacaacaa ttatgcaacc tactatgccg actctgtgaa ggatagattc accatctcaa gagatgattc aaagaactca ctgtatctgc aaatgaacag cctgaaaacc gaggacacgg ccgtgtatta ctgtgtgaga cacggtaact tcggcaattc ttacgtgtct tggtttgctt attggggaca ggggacactg gtgactgtgt cttcc
```

Amino Acid Sequence of Humanized mAb2 Variable Heavy Chain Variant QV (h-mAb2 VL-QV) (SEQ ID NO:52):

```
EVQLVESGGG LVQPKGSLKL SCAASGFTFN TYAMNWVRQA

PGKGLEWVAR IRSKYNNYAT YYADSVKDRF TISRDDSQSI

LYLQMNNLKT EDTAMYYCVR HGNFGNSYVS WFAYWGQGTL

VTVSA
```

Polynucleotide Sequence Encoding Humanized mAb2 Variable Heavy Chain Variant QV (h-mAb2 VL-QV) (SEQ ID NO:53):

```
gaggtgcagc tggtggaaag cggcggagga ctggtgcagc caaagggatc actgaaactg tcctgcgccg cctccggctt cacctttaac acatacgcta tgaattgggt gcgacaggca cctggcaagg gcctggagtg ggtggcaagg atcaggtcca agtacaacaa ttatgcaacc tactatgccg actctgtgaa ggatagattc acaatcagtc gcgacgattc ccagagcatt ctgtatctgc agatgaacaa tctgaaaact gaagacaccg ccatgtacta ttgtgtgcgg cacggtaact tcggcaattc ttacgtgtct tggtttgctt attggggaca ggggacactg gtgactgtgt cttcc
```

Example 4 mAb2 Binds to Both Human and Cynomolgus Monkey CD3

Figure 2A:
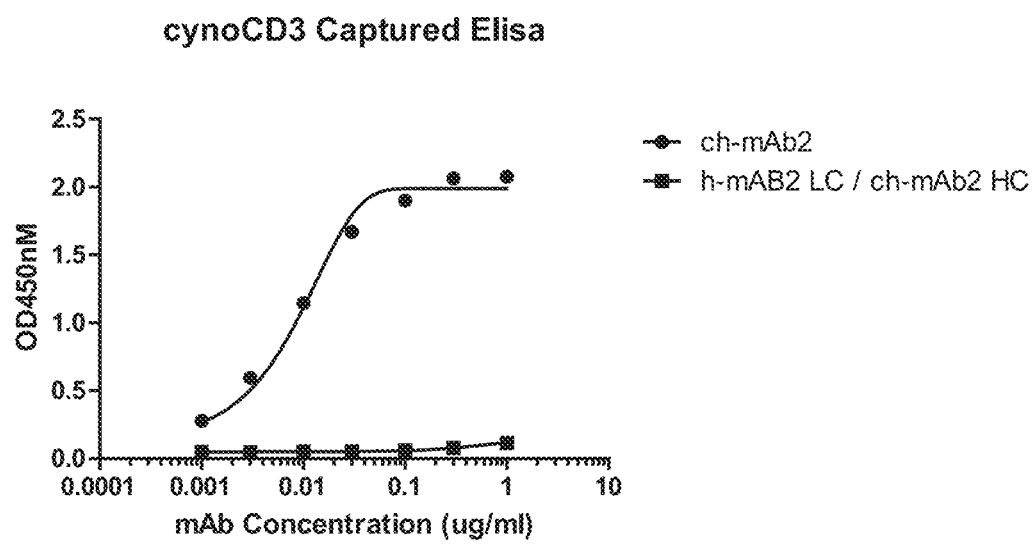
FIGS. 2A-2B show the results of a capture ELISA in which the ability of anti-CD3 antibody mAB2 (FIG. 2A) or a chimeric derivative of antibody mAB2 (ch-mAb2) (FIG. 2B) was assessed using human soluble CD3 ("shCD3") or soluble cynomolgus monkey CD3 ("scCD3").
Figure 2B:
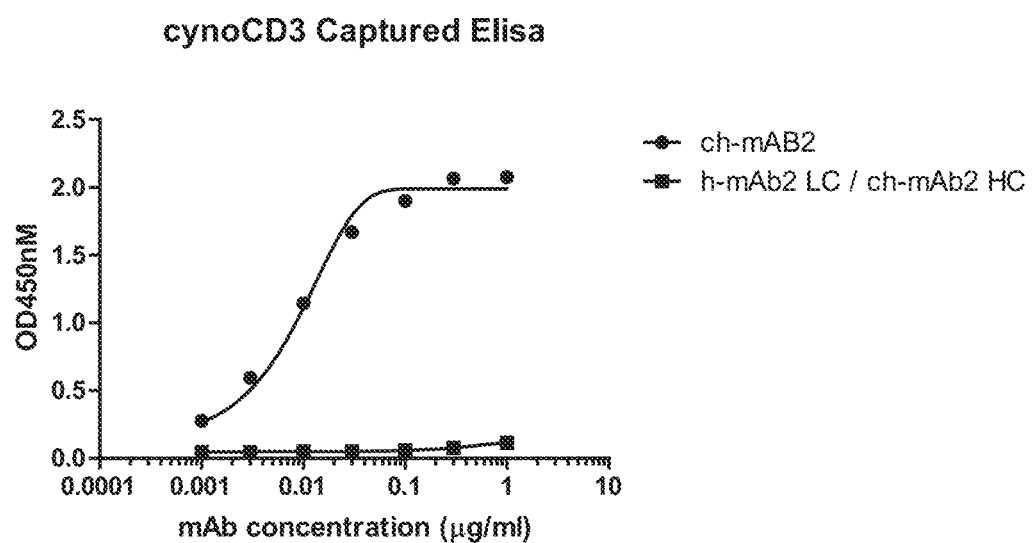

As discussed above, the mAb2 antibody was originally isolated based upon its ability to bind human CD3. In order to assess the ability of mAb2 to bind to non-human CD3, a capture ELISA was performed. Plates were coated with 1 µg/ml of CD3 (either human or cynomolgus monkey) and incubated in the presence of various concentrations of a chimeric variant of mAb2 antibody (ch-mAb2) (containing the variable sequences of mAb2 and the constant regions of a human antibody). As a control, plates were also incubated with an antibody composed of the light chain of a humanized mAb2 antibody and the heavy chain of the chimeric antibody. The results of this experiment are shown in FIGS. 2A and 2B, and reveal that the chimeric mAb2 variant exhibited equivalent binding to human CD3 and to cynomolgus monkey CD3.

Example 5

Analysis of Binding Characteristics of Variants of h-mAb2 Light and Heavy Chains An analysis was conducted to determine the effect of variations in the framework residues of the light chain of mAb2. Table 2 indicates the substitutions studied.

TABLE 2

| | | Light Chain | | | | | | | | |
|---|---|---|---|---|---|---|---|---|---|---|
| | | Kabat Residue No: | | | | | | | | |
| | | 36 | 38 | 41 | 42 | 43 | 44 | 45 | 46 | SEQ ID |
| | | SEQ ID NO: 5 Residue No: | | | | | | | | |
| | | 38 | 40 | 43 | 44 | 45 | 46 | 47 | 48 | NO: |
| Variant | mAb2-VL | V | E | D | H | L | F | T | G | 5 |
| | h-mAb2 VL-1 | F | Q | G | Q | A | P | R | T | 16 |
| | h-mAb2 VL-2 | V | | | | | | | | 18 |
| | h-mAb2 VL-3 | | E | | | | | | | 20 |
| | h-mAb2 VL-4 | | | | | | | | G | 22 |
| | h-mAb2 VL-5 | V | E | | | | | | | 24 |
| | h-mAb2 VL-6 | V | | | | | | | G | 26 |
| | h-mAb2 VL-7 | | E | | | | | | G | 28 |
| | h-mAb2 VL-8 | V | E | | | | | | G | 30 |
| | h-mAb2 VL-9 | V | E | | | | F | | G | 32 |
| | h-mAb2 VL-10 | | | D | H | L | F | T | G | 34 |

| | | Heavy Chain | | | | | |
|---|---|---|---|---|---|---|---|
| | | Kabat Residue No: | | | | | |
| | | 30 | 49 | 52a | 58 | 93 | SEQ ID |
| | | SEQ ID NO: 7 Residue No: | | | | | |
| | | 30 | 49 | 53 | 61 | 99 | NO: |
| Variant | mVH | N | A | | Y | V | 7 |
| | hVH-1 | S | G | | | A | 36 |
| | hVH-2 | N | | | | | 38 |
| | hVH-3 | | A | | | | 40 |
| | hVH-4 | | | | | V | 42 |
| | hVH-5 | N | A | | | | 44 |
| | hVH-6 | N | | | | V | 46 |
| | hVH-6L | N | | | E | V | 54 |
| | hVH-6M | N | | N | E | V | 72 |
| | hVH-7 | | A | | | V | 48 |
| | hVH-8 | N | A | | | V | 50 |
| | hVH-8L | N | A | | E | | 55 |
| | hVH-8M | N | A | N | E | V | 74 |

Figure 3:
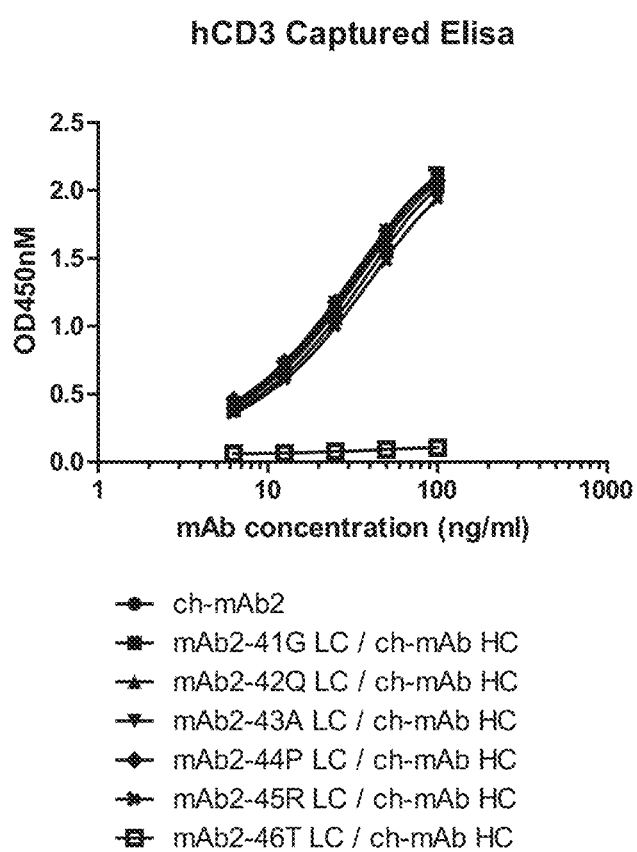
FIG. 3 show the results of analyses to determine the effect of variations in Kabat numbered framework residues 41-46 of the light chain of mAb2.

Antibodies having mAb2 light chains of SEQ ID NO:11, but containing a (Kabat numbered) substitution of D41G, H42Q, L43A, F44P, T45R, or G46T and heavy chains of chimeric mAb2 (CDRs of mAb2 with hFR1-mFR2-hFR3-4) were formed and their binding assessed using a capture ELISA. Plates were coated with 1 µg/ml of the extracellular domain of human CD3 (soluble hCD3 or "shCD3") and incubated in the presence of various concentrations of antibody. The results (FIG. 3) indicate that a substitution of T at Kabat position 46 eliminated the ability of the antibody to bind to shCD3.

Figure 4:
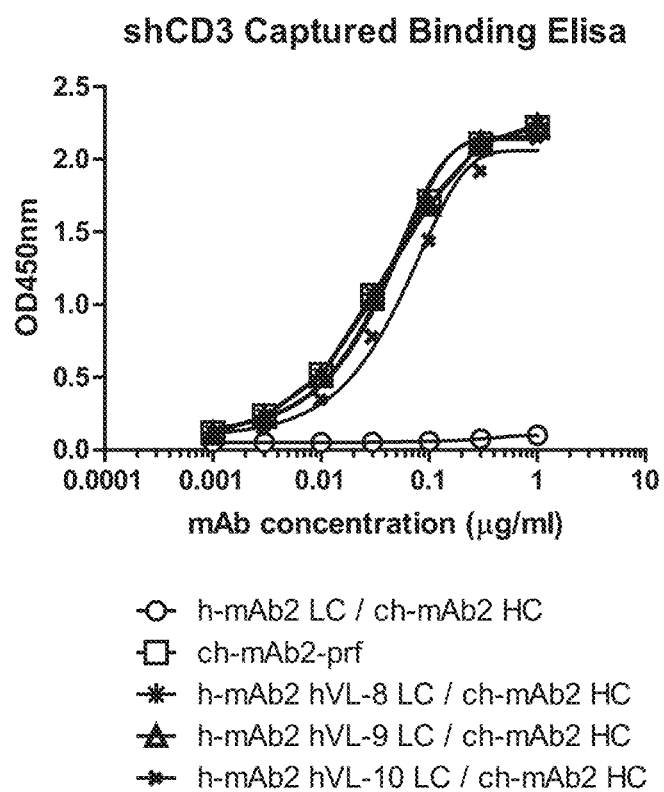
FIG. 4 show the results of analyses to determine the effect of variations in Kabat numbered framework residues 36, 38, 44 and 46 of the light chain of mAb2.

Additional studies were conducted to assess the impact of variations at Kabat light chain positions 36, 38, 44 and 46. Antibodies were formed having an h-mAb2 VL-8, h-mAb2 VL-9 or h-mAb2 VL-10 light chain and the heavy chain of the mAb2 chimeric antibody and evaluated using the above-described capture ELISA. The results of this experiment are shown in FIG. 4, and reveal that the binding to shCD3 by an antibody having the hVL-8 light chain was similar to that of an antibody having the chimeric mAb2 light chain.

Figure 5:
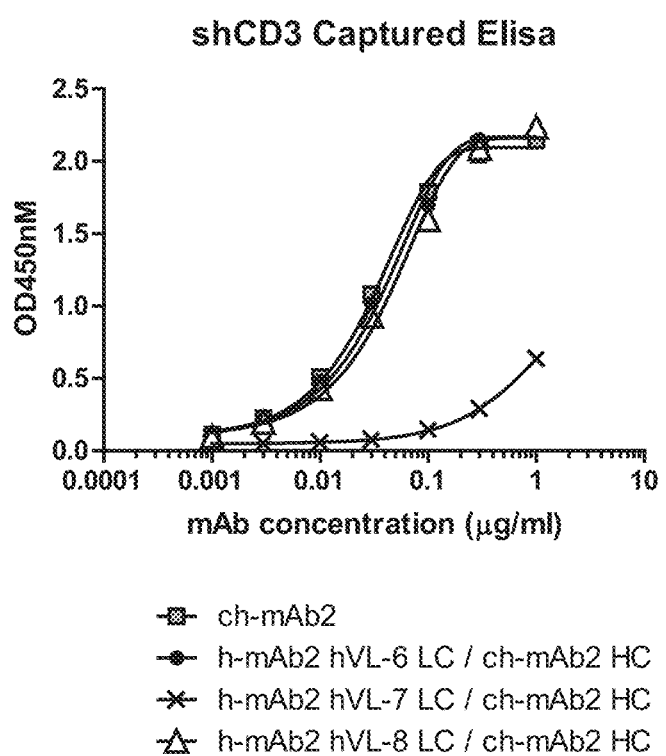
FIG. 5 show the results of analyses to determine the effect of variations in Kabat numbered framework residues 36, 38 and 46 of the light chain of mAb2.

Antibodies were also formed having an h-mAb2 VL-6, h-mAb2 VL-7 or h-mAb2 VL-8 light chain and the heavy chain of the mAb2 chimeric antibody and evaluated using the above-described capture ELISA (except that the plates were coated with 0.5 µg/ml of shCD3 in phosphate buffered saline) to determine the impact of additional substitutions at positions 36, 38 and 46. The results of this experiment are shown in FIG. 5, and reveal that the Kabat substitutions F36V and T46G were sufficient to yield an antibody whose binding to shCD3 was similar to that of an antibody having the chimeric mAb2 light chain.

Figure 6:
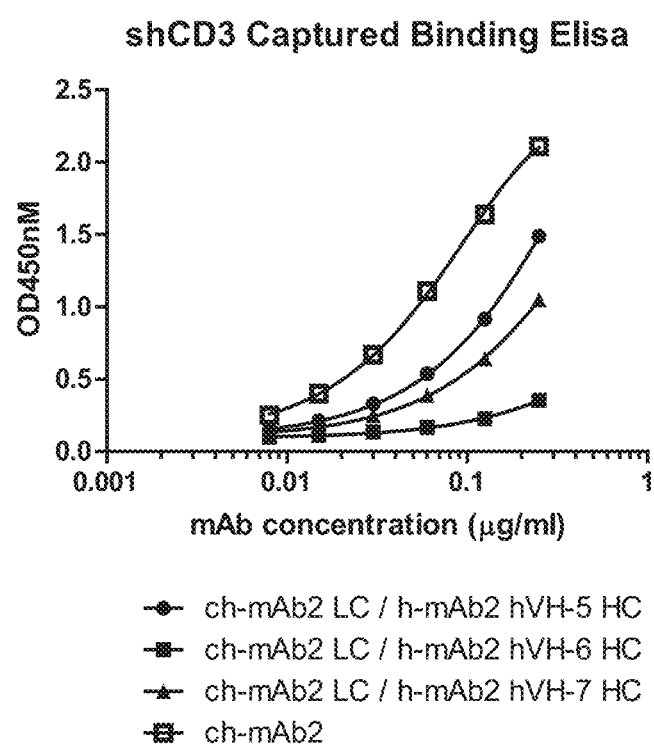
FIG. 6 show the results of analyses to determine the effect of variations in Kabat numbered framework residues 30, 49 and 93 of the heavy chain of mAb2.
Figure 7:
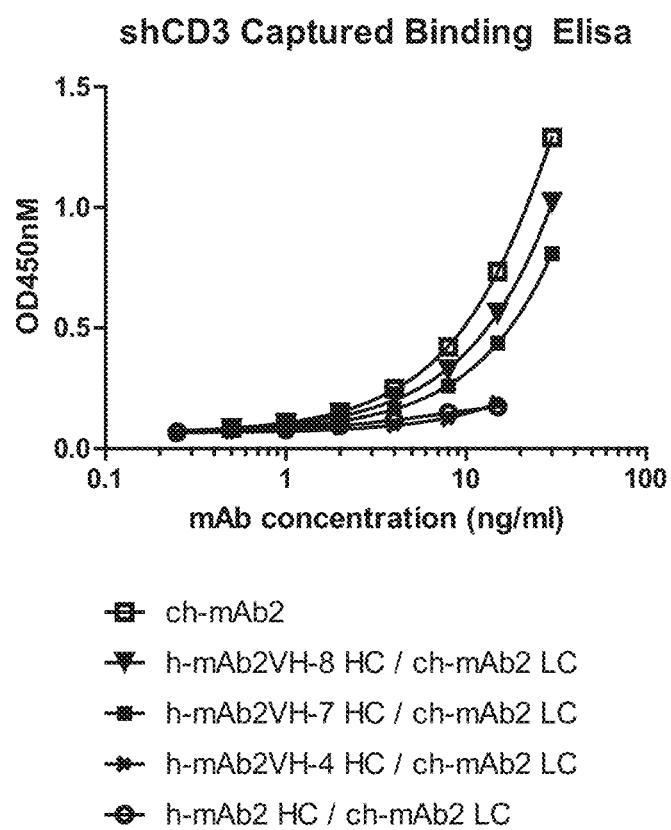
FIG. 7 show the results of additional analyses conducted to determine the effect of variations in Kabat numbered framework residues 30, 49 and 93 of the heavy chain of mAb2.

The impact of substitutions in the sequence of the heavy chain of mAb2 was assessed by forming antibodies having the light chain of the chimeric mAb2 antibody and heavy chain h-mAb2 VH-5, h-mAb2 VH-6 or h-mAb2 VH-7 and evaluating binding using the above-described capture ELISA (using a 1 μg/ml coating of shCD3). The results of these investigations are shown in FIG. 6. Antibodies were additionally formed having the light chain of the chimeric mAb2 antibody and a humanized variant of heavy chain h-mAb2 VH-4, h-mAb2 VH-7 or h-mAb2 VH-9. Such antibodies were evaluated for binding using the above-described capture ELISA. The results of these investigations are shown in FIG. 7.

Heavy chains hVH-6L (and its variant, hVH-6M), and hVH-8L (and its variant VH-8M) are particularly preferred for producing antibodies have a lower affinity for CD3 than antibodies composed of hVH-1, hVH-2, hVH-3, hVH-4, hVH-5, hVH-6, hVH-7 or hVH-8 of Table 2. Such reduced affinity antibodies will preferably be composed of either heavy chain hVH-6L or heavy chain VH-8L in combination with any of light chain h-mAb2 VL-1, h-mAb2 VL-2, h-mAb2 VL-3, h-mAb2 VL-4, h-mAb2 VL-5, h-mAb2 VL-6, h-mAb2 VL-7, h-mAb2 VL-8, h-mAb2 VL-9, or h-mAb2 VL-10. A particularly preferred deimmunized antibody will be composed of heavy chain hVH-6L (or its variant, hVH-6M) and light chain h-mAb2 VL-6, or heavy chain hVH-8L (or its variant, hVH-8M) and light chain h-mAb2 VL-6. The sequences of such polypeptides are presented below:

Amino acid sequence of hVH-6L (SEQ ID NO:54):

```
EVQLVESGGG LVQPGGSLRL SCAASGFTFN TYAMNWVRQA
PGKGLEWVGR IRNKYNNYAT EYADSVKDRF TISRDDSKNS
LYLQMNSLKT EDTAVYYCVR HGNFGNSYVS WFAYWGQGTL
VTVSS
```

Amino acid sequence of hVH-8L (SEQ ID NO:55):

```
EVQLVESGGG LVQPGGSLRL SCAASGFTFN TYAMNWVRQA
PGKGLEWVAR IRNKYNNYAT EYADSVKDRF TISRDDSKNS
LYLQMNSLKT EDTAVYYCVR HGNFGNSYVS WFAYWGQGTL
VTVSS
```

Heavy chains hVH-6L and hVH-8L were further modified to produce variants possessing an asparagine at position 52a (S52aN) modification. The amino acid sequences and corresponding polynucleotide-encoding sequences of these modified heavy chains are as follows:

Amino acid sequence of hVH-6M (SEQ ID NO:72):

```
EVQLVESGGG LVQPGGSLRL SCAASGFTFN TYAMNWVRQA
PGKGLEWVGR IRSKYNNYAT EYAASVKDRF TISRDDSKNS
LYLQMNSLKT EDTAVYYCVR HGNFGNSYVS WFAYWGQGTL
VTVSS
```

Polynucleotide Sequence Encoding hVH-6M Variable Heavy Chain (SEQ ID NO:73):

```
gaggtgcagc tggtggagtc tggggggaggc ttggtccagc
ctggagggtc cctgagactc tcctgtgcag cctctggatt
caccttcaac acatacgcta tgaattgggt ccgccaggct
ccagggaagg ggctggagtg ggttggaagg atcaggtcca
agtacaacaa ttatgcaacc gagtatgccg actctgtgaa
ggatagattc accatctcaa gagatgattc aaagaactca
ctgtatctgc aaatgaacag cctgaaaacc gaggacacgg
ccgtgtatta ctgtgtgaga cacggtaact tcggcaattc
ttacgtgtct tggtttgctt attggggaca ggggacactg
gtgactgtgt cttcc
```

Amino acid sequence of hVH-8M (SEQ ID NO:74):

```
EVQLVESGGG LVQPGGSLRL SCAASGFTFN TYAMNWVRQA
PGKGLEWVAR IRNKYNNYAT EYAASVKDRF TISRDDSKNS
LYLQMNSLKT EDTAVYYCVR HGNFGNSYVS WFAYWGQGTL
VTVSS
```

Polynucleotide Sequence Encoding hVH-8M Variable Heavy Chain (SEQ ID NO:75):

```
gaggtgcagc tggtggagtc tggggggaggc ttggtccagc
ctggagggtc cctgagactc tcctgtgcag cctctggatt
caccttcaac acatacgcta tgaattgggt ccgccaggct
ccagggaagg ggctggagtg ggttgcaagg atcaggaaca
agtacaacaa ttatgcaacc gagtatgccg actctgtgaa
ggatagattc accatctcaa gagatgattc aaagaactca
ctgtatctgc aaatgaacag cctgaaaacc gaggacacgg
ccgtgtatta ctgtgtgaga cacggtaact tcggcaattc
ttacgtgtct tggtttgctt attggggaca ggggacactg
gtgactgtgt cttcc
```

Heavy chains hVH-8 di-1 and hVH-8 di-2 are particularly preferred for producing antibodies that are less immunogenic than antibodies composed of hVH-1, hVH-2, hVH-3, hVH-4, hVH-5, hVH-6, hVH7 or hVH-8 of Table 2. Such deimmunized antibodies will preferably be composed of either heavy chain hVH-8 di-1 or heavy chain hVH-8 di-2 in combination with any of light chain h-mAb2 VL-1, h-mAb2 VL-2, h-mAb2 VL-3, h-mAb2 VL-4, h-mAb2 VL-5, h-mAb2 VL-6, h-mAb2 VL-7, h-mAb2 VL-8, h-mAb2 VL-9, or h-mAb2 VL-10. A particularly preferred deimmunized antibody will be composed of heavy chain hVH-8 di-1 and light chain h-mAb2 VL-6, or heavy chain hVH-8 di-2 and light chain h-mAb2 VL-6.

Amino acid sequence of hXR32VH-8 di-1 (SEQ ID NO:56):

```
EVQLVESGGG LVQPGGSLRL SCAASGFTFN TYAMNWVRQA
PGKGLEWVAR TRSKANSYTT YYAASVKGRF TISRDDSKNS
LYLQMNSLKT EDTAVYYCAR HGNFGNSYVS WFAYWGQGTL
VTVSS
```

Amino acid sequence of hXR32VH-8 di-2 (SEQ ID NO:57):

```
EVQLVESGGG LVQPGGSLRL SCAASGFTFN TYAMNWVRQA
PGKGLEWVGR TRSKANSYTT YYAASVKGRF TISRDDSKNS
LYLQMNSLKT EDTAVYYCAR HGNFGNSYVS WFAYWGQGTL
VTVSS
```

Such deimmunized antibodies will preferably be composed of either heavy chain hVH-8L di-1 or heavy chain VH-8L di-2 in combination with any of light chain h-mAb2 VL-1, h-mAb2 VL-2, h-mAb2 VL-3, h-mAb2 VL-4, h-mAb2 VL-5, h-mAb2 VL-6, h-mAb2 VL-7, h-mAb2 VL-8, h-mAb2 VL-9, or h-mAb2 VL-10. A particularly preferred deimmunized antibody will be composed of heavy chain hVH-9M di-1 and light chain h-mAb2 VL-6, or heavy chain hVH-8L di-2 and light chain h-mAb2 VL-6.

Additional humanized variants of the mAb2 murine monoclonal antibody variable heavy chain (SEQ ID NO:7) were also produced. The amino acid sequences of such variants are presented below, with changes from SEQ ID NO:7 indicated in boldface and underlining:

Amino Acid Sequence of variant "a" (I51T Y52cA) of humanized mAb2 murine monoclonal antibody variable heavy chain (SEQ ID NO:76):

```
EVKLLESGGG LVQPKGSLKL SCAASGFTFN TYAMNWVRQA
PGKGLEWVAR TASKANNYAT YYADSVKDRF TISRDDSQSI
LYLQMNNLKT EDTAMYYCVR HGNFGNSYVS WFAYWGQGTL
VTVSA
```

Amino Acid Sequence of variant "b" (I51T N54S) of humanized mAb2 murine monoclonal antibody variable heavy chain (SEQ ID NO:77):

```
EVKLLESGGG LVQPKGSLKL SCAASGFTFN TYAMNWVRQA
PGKGLEWVAR TRSKYNSYAT YYADSVKDRF TISRDDSQSI
LYLQMNNLKT EDTAMYYCVR HGNFGNSYVS WFAYWGQGTL
VTVSA
```

Amino Acid Sequence of variant "C" (I51T A56T) of humanized mAb2 murine monoclonal antibody variable heavy chain SE ID NO:78):

```
EVKLLESGGG LVQPKGSLKL SCAASGFTFN TYAMNWVRQA
PGKGLEWVAR TRSKYNNYTT YYADSVKDRF TISRDDSQSI
LYLQMNNLKT EDTAMYYCVR HGNFGNSYVS WFAYWGQGTL
VTVSA
```

Amino Acid Sequence of variant "d" (I51T Y52cA N54S) of humanized mAb2 murine monoclonal antibody variable heavy chain (SEQ ID NO:79):

```
EVKLLESGGG LVQPKGSLKL SCAASGFTEN TYAMNWVRQA
PGKGLEWVAR TRSKANSYAT YYADSVKDRF TISRDDSQSI
LYLQMNNLKT EDTAMYYCVR HGNFGNSYVS WFAYWGQGTL
VTVSA
```

Amino Acid Sequence of variant "e" (I51T N54S A56T) of humanized mAb2 murine monoclonal antibody variable heavy chain (SEQ ID NO:80):

```
EVKLLESGGG LVQPKGSLKL SCAASGFTFN TYAMNWVRQA
PGKGLEWVAR TRSKYNSYTT YYADSVKDRF TISRDDSQSI
LYLQMNNLKT EDTAMYYCVR HGNFGNSYVS WFAYWGQGTL
VTVSA
```

Amino Acid Sequence of variant "f" (I51T Y52cA N54S A56T) of humanized mAb2 murine monoclonal antibody variable heavy chain (SEQ ID NO:81):

```
EVKLLESGGG LVQPKGSLKL SCAASGFTFN TYAMNWVRQA
PGKGLEWVAR TRSKANSYTT YYADSVKDRF TISRDDSQSI
LYLQMNNLKT EDTAMYYCVR HGNFGNSYVS WFAYWGQGTL
VTVSA
```

Amino Acid Sequence of variant "g" (I51T D61A) of humanized mAb2 murine monoclonal antibody variable heavy chain (SEQ ID NO:82):

```
EVKLLESGGG LVQPKGSLKL SCAASGFTFN TYAMNWVRQA
PGKGLEWVAR TRSKYNNYAT YYAASVKDRF TISRDDSQSI
LYLQMNNLKT EDTAMYYCVR HGNFGNSYVS WFAYWGQGTL
VTVSA
```

Amino Acid Sequence of variant "h" (I51T D65G) of humanized mAb2 murine monoclonal antibody variable heavy chain (SEQ ID NO:83):

```
EVKLLESGGG LVQPKGSLKL SCAASGFTFN TYAMNWVRQA
PGKGLEWVAR TRSKYNNYAT YYADSVKGRF TISRDDSQSI
LYLQMNNLKT EDTAMYYCVR HGNFGNSYVS WFAYWGQGTL
VTVSA
```

Amino Acid Sequence of variant "i" (I51T Y52cA N54S D61A) of humanized mAb2 murine monoclonal antibody variable heavy chain (SEQ ID NO:84):

```
EVKLLESGGG LVQPKGSLKL SCAASGFTFN TYAMNWVRQA

PGKGLEWVAR TRSKANSYAT YYAASVKDRF TISRDDSQSI

LYLQMNNLKT EDTAMYYCVR HGNFGNSYVS WFAYWGQGTL

VTVSA
```

Amino Acid Sequence of variant "j" (I51T Y52cA N54S D65G) of humanized mAb2 murine monoclonal antibody variable heavy chain (SEQ ID NO:85):

```
EVKLLESGGG LVQPKGSLKL SCAASGFTFN TYAMNWVRQA

PGKGLEWVAR TRSKANSYAT YYADSVKGRF TISRDDSQSI

LYLQMNNLKT EDTAMYYCVR HGNFGNSYVS WFAYWGQGTL

VTVSA
```

Amino Acid Sequence of variant "k" (I51T Y52cA N54S D61A D65G) of humanized mAb2 murine monoclonal antibody variable heavy chain (SEQ ID NO:86):

```
EVKLLESGGG LVQPKGSLKL SCAASGFTFN TYAMNWVRQA

PGKGLEWVAR TRSKANSYAT YYAASVKGRF TISRDDSQSI

LYLQMNNLKT EDTAMYYCVR HGNFGNSYVS WFAYWGQGTL

VTVSA
```

Amino Acid Sequence of variant "2k" (I51T Y52cA N54S D61A D65G (VH8-A49G V93A)) of humanized mAb2 murine monoclonal antibody variable heavy chain (SEQ ID NO:87):

```
EVQLVESGGG LVQPGGSLRL SCAASGFTFN TYAMNWVRQA

PGKGLEWVGR TRSKANSYTT YYAASVKGRF TISRDDSKNS

LYLQMNSLKT EDTAVYYCAR HGNFGNSYVS WFAYWGQGTL

VTVSS
```

Amino Acid Sequence of variant "5k" (I51T Y52cA N54S D61A D65G (VH8-V93A)) of humanized mAb2 murine monoclonal antibody variable heavy chain (SEQ ID NO:88):

```
EVQLVESGGG LVQPGGSLRL SCAASGFTFN TYAMNWVRQA

PGKGLEWVAR TRSKANSYTT YYAASVKGRF TISRDDSKNS

LYLQMNSLKT EDTAVYYCAR HGNFGNSYVS WFAYWGQGTL

VTVSS
```

All such additional humanized variants of the mAb2 murine monoclonal antibody variable heavy chain may be employed to form the deimmunized antibodies of the present invention. Such additional deimmunized and humanized antibodies will preferably be composed of any of heavy chains: a, b, c, d, e, f, g, h, i, j, k, 2k or 5k, in combination with any of light chain: h-mAb2 VL-1, h-mAb2 VL-2, h-mAb2 VL-3, h-mAb2 VL-4, h-mAb2 VL-5, h-mAb2 VL-6, h-mAb2 VL-7, h-mAb2 VL-8, h-mAb2 VL-9, or h-mAb2 VL-10. A particularly preferred deimmunized antibody will be composed of heavy chain 2k or 5k and light chain h-mAb2 VL-6, or heavy chain hVH-8M8L di-2 and light chain h-mAb2 VL-6. Variants 2k and 5k bind to Protein A in the variable region, thus facilitating the purification of molecules (such as diabodies) that may lack Fc regions or other domains that may be used to sequester such molecules from other molecules. Variants hVH-8M, hVH-8L. hVH-6M and hVH-6L exhibit reduced immunogenicity relative to their respective parental polypeptides.

Figure 8A:
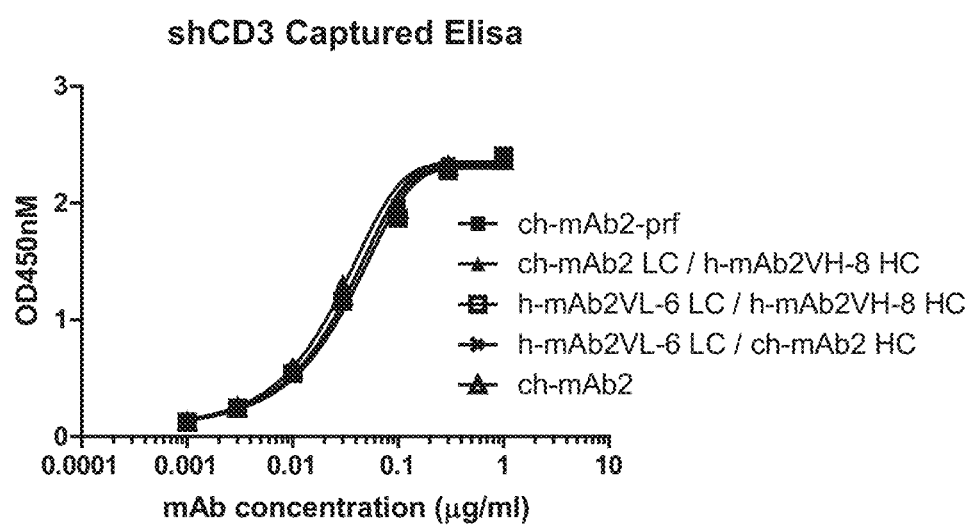
FIGS. 8A-8B show the results of analyses conducted to assess the ability of chimeric and humanized mAb2 to bind to non-human CD3.
Figure 8B:
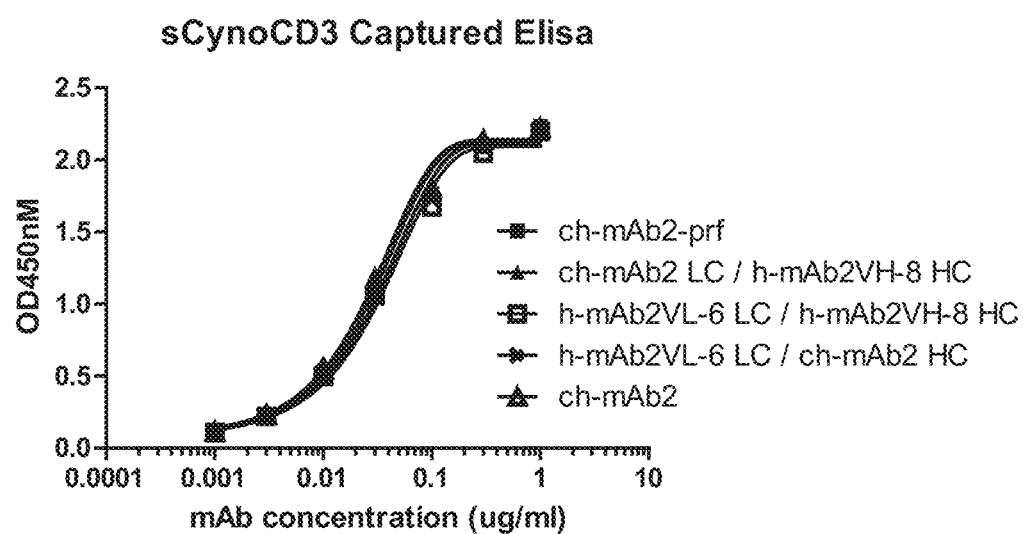
Figure 9A:
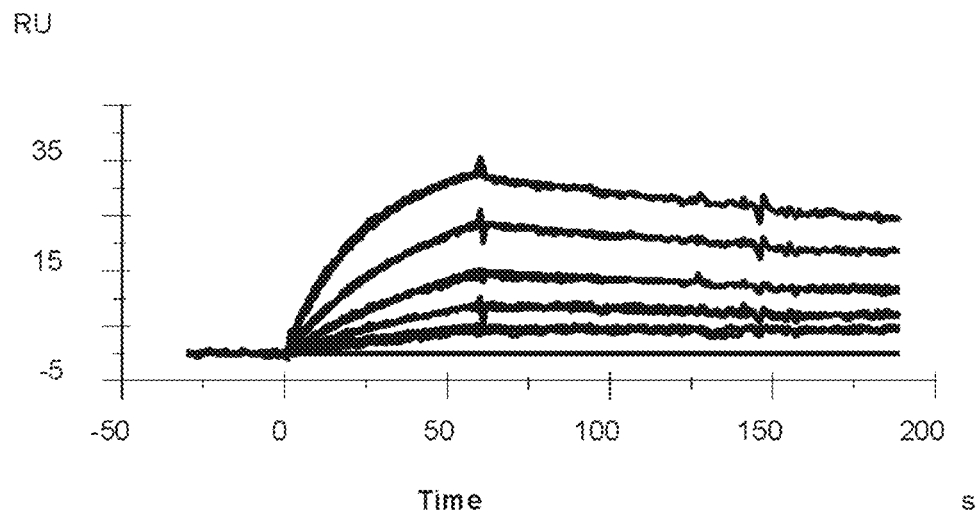
FIGS. 9A-9D show sensorgram tracings of BIACORE™ analyses done to determine the kinetics of the binding of ch-mAB2 or h-mAb2 and scCD3 or scCD3.
Figure 9B:
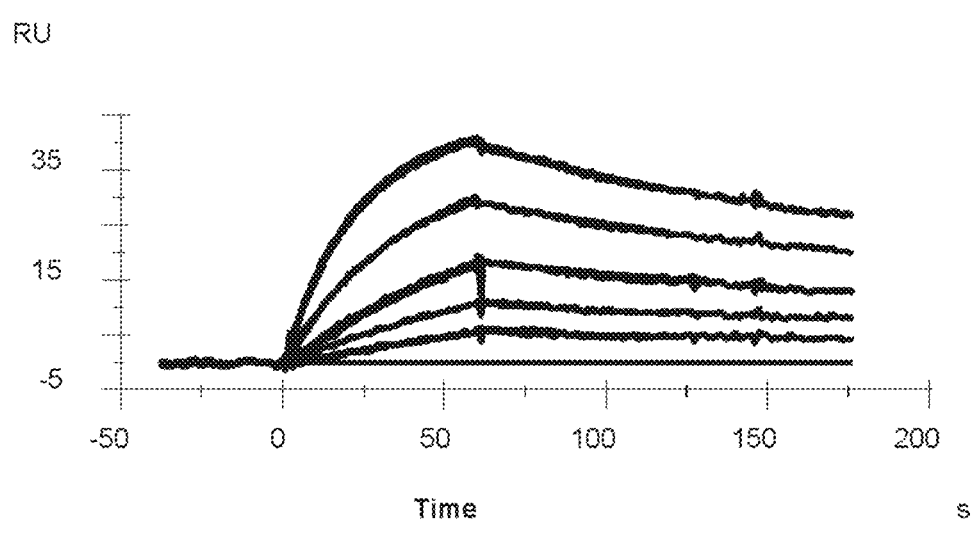
Figure 9C:
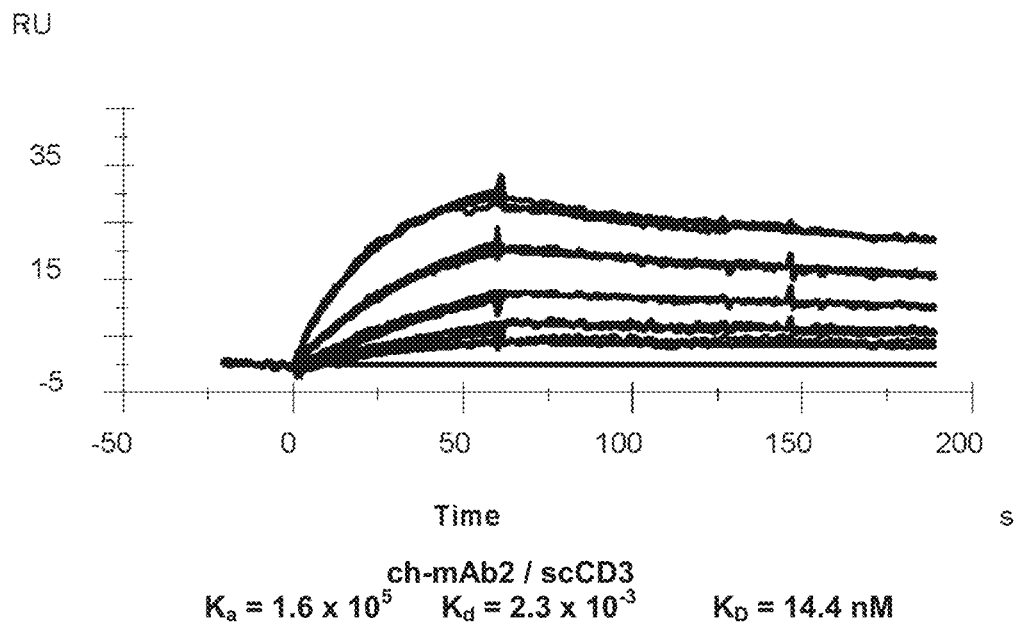
Figure 9D:
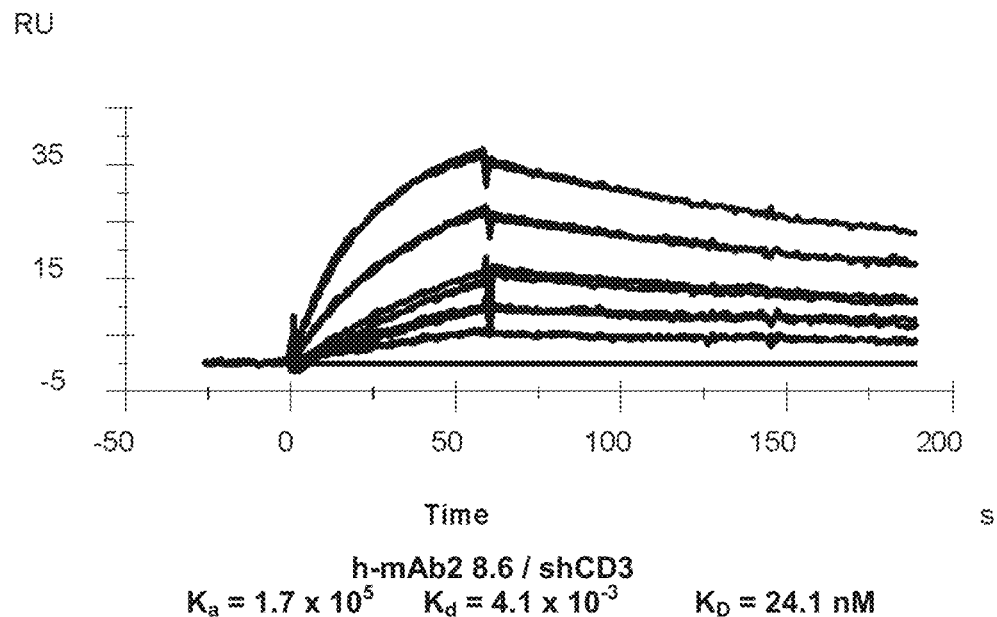

The invention particularly concerns deimmunized and humanized antibodies composed of heavy chain hVH-8 and light chain VL-6. The invention additionally particularly concerns deimmunized and humanized antibodies composed of heavy chain hVH-4 and light chain VL-6. The invention additionally particularly concerns deimmunized and humanized antibodies composed of heavy chain hVH-2k and light chain VL-6 Example 6 Analysis of Binding Characteristics of Variants of Chimeric and Humanized mAb2 Light and Heavy Chains In order to assess the ability of chimeric and humanized mAb2 to bind to non-human CD3, a capture ELISA was performed. Plates were coated with 1 μg/ml of the extracellular domain of CD3 (soluble CD3) (either human or cynomolgus monkey) and incubated in the presence of various concentrations of antibody. The results of this experiment are shown in FIGS. 8A and 8B, and reveal that mAb2 and its humanized variant exhibited equivalent binding to soluble human CD3 and to soluble cynomolgus monkey CD3.

Example 7

Quantitation of Binding of mAb2 to Human and Cynomolgus Monkey CD3

In order to quantitate the extent of binding between mAb2 and human or cynomolgus monkey CD3, BIACORE™ analyses were conducted. BIACORE™ analyses measure the dissociation off-rate, $k_d$. The binding affinity ($K_D$) between an antibody and its target is a function of the kinetic constants for association (on rate, $k_a$) and dissociation (off-rate, $k_d$) according to $K_D = k_d/k_a$. The BIACORE™ analysis uses surface plasmon resonance to directly measure these kinetic parameters. Anti-CD3 antibody mAb2 (6.3-100 nM) was immobilized to a support using anti-EK antibodies and incubated in the presence of soluble human CD3 (shCD3) or soluble cynomolgus monkey CD3 (scCD3). The time course of dissociation was measured and a bivalent fit of the data conducted. The results of the BIACORE™ analyses are shown in FIGS. 9A-9D. The kinetic data is summarized in Table 3.

TABLE 3

| shCD3 | | | |
|---|---|---|---|
| Antibody | $k_a$ | $k_d$ | $K_D$ |
| ch-mAb2 | $1.7 \times 10^5$ M$^{-1}$ sec$^{-1}$ | $2.5 \times 10^{-3}$ sec$^{-1}$ | 14.7 nM |
| h-mAb2 | $1.9 \times 10^5$ M$^{-1}$ sec$^{-1}$ | $3.8 \times 10^{-3}$ sec$^{-1}$ | 20.0 nM |
| scCD3 | | | |
| Antibody | $k_a$ | $k_d$ | $K_D$ |
| ch-mAb2 | $1.6 \times 10^5$ M$^{-1}$ sec$^{-1}$ | $2.3 \times 10^{-3}$ sec$^{-1}$ | 14.4 nM |
| h-mAb2 | $1.7 \times 10^5$ M$^{-1}$ sec$^{-1}$ | $4.1 \times 10^{-3}$ sec$^{-1}$ | 24.1 nM |

Example 8

Bispecific Binding Data for DART™ Diabodies Containing CDRs of h-mAb2

The CDRs of humanized mAb2 (h-mAb2) were used to produce a series of DART™ diabodies having an anti-CD3 first epitope binding site and a second epitope binding site capable of binding to Her2/neu (DART™ diabody "Her2-h-mAb2"), or to CD19 (DART™ diabody "CD19-h-mAb2") or to the epidermal growth factor receptor (EGFR) (DART™ diabody "ERBITUX™-h-mAb2").

Her2/neu-h-mAb2 DART™ Diabody

Amino acid sequence of the hXR32VL-Her-2VH E coil of the Her2-h-mAb2 DART™ diabody (the linkers between the hXR32VL sequence and the Her2VH sequence and between the Her2VH sequence and the E coil sequence are underlined) (SEQ ID NO:58):

```
QAVVTQEPSL TVSPGGTVTL TCRSSTGAVT TSNYANWVQQ
KPGQAPRGLI GGTNKRAPWT PARFSGSLLG GKAALTITGA
QAEDEADYYC ALWYSNLWVF GGGTKLTVLG GGGSGGGGQV
QLQQSGPELV KPGASLKLSC TASGFNIKDT YIHWVKQRPE
QGLEWIGRIY PTNGYTRYDP KFQDKATITA DTSSNTAYLQ
VSRLTSEDTA VYYCSRWGGD GFYAMDYWGQ GASVTVSSGG
CGGGKVAALK EKVAALKEKV AALKEKVAAL KE
```

Amino acid sequence of the Her2VL-hXR32VH-K coil of the Her2-h-mAb2 DART™ diabody (the linkers between the Her2VL sequence and the hXR32VH sequence and between the hXR32VH sequence and the K coil sequence are underlined) (SEQ ID NO:59):

```
DIVMTQSHKF MSTSVGDRVS ITCKASQDVN TAVAWYQQKP
GHSPKLLIYS ASFRYTGVPD RFTGNRSGTD FTFTISSVQA
ADLAVYYCQQ HYTTPPTFGG GTKLEIKRAG GGSGGGGEVQ
LVESGGGLVQ PGGSLRLSCA ASGFTFNTYA MNWVRQAPGK
GLEWVARIRS KYNNYATYYA DSVKDRFTIS RDDSKNSLYL
QMNSLKTEDT AVYYCVRHGN FGNSYVSWFA YWGQGTLVTV
SSGGCGGGEV AALEKEVAAL EKEVAALEKE VAALEK
```

CD19-h-mAb2 DART™ Diabody

Amino acid sequence of the CD19VL-hXR32VH-E coil of the CD19-h-mAb2 DART™ diabody (the linkers between the CD19VL sequence and the hXR32VH sequence and between the hXR32VH sequence and the E coil sequence are underlined) (SEQ ID NO:60):

```
DIQLTQSPAS LAVSLGQRAT ISCKASQSVD YDGDSYLNWY
QQIPGQPPKL LIYDASNLVS GIPPRESGSG SGTDFTLNIH
PVEKVDAATY HCQQSTEDPW TFGGGTKLEI KGGGSGGGGE
VQLVESGGGL VQPGGSLRLS CAASGFTFNT YAMNWVRQAP
GKGLEWVARI RSKYNNYATY YADSVKDRFT ISRDDSKNSL
YLQMNSLKTE DTAVYYCVRH GNFGNSYVSW FAYWGQGTLV
TVSSGGCGGG EVAALEKEVA ALEKEVAALE KEVAALEK
```

Amino acid sequence of the hXR32VL-CDT9VH-K coil of the CD19-h-mAb2 DART™ diabody (the linkers between the hXR32VL sequence and the CD19VH sequence and between the CD19VH sequence and the K coil sequence are underlined) (SEQ ID NO:61):

```
QAVVTQEPSL TVSPGGTVTL TCRSSTGAVT TSNYANWVQQ
KPGQAPRGLI GGTNKRAPWT PARFSGSLLG GKAALTITGA
QAEDEADYYC ALWYSNLWVF GGGTKLTVLG GGGSGGGGQV
QLQQSGAELV RPGSSVKISC KASGYAFSSY WMNWVKQRPG
QGLEWIGQIW PGDGDTNYNG KFKGKATLTA DESSSTAYMQ
LSSLASEDSA VYFCARRETT TVGRYYYAMD YWGQGTTVTV
SSGGCGGGKV AALKEKVAAL KEKVAALKEK VAALKE
```

ERBITUX™-h-mAb2 DART™ Diabody

Amino acid sequence of the hXR32VL-EGFRVH-E coil of the ERBITUX™-h-mAb2 DART™ diabody (the linkers between the hXR32VL sequence and the EGFRVH sequence and between the EGFRVH sequence and the E coil sequence are underlined) (SEQ ID NO:62):

```
QAVVTQEPSL TVSPGGTVTL TCRSSTGAVT TSNYANWVQQ
KPGQAPRGLI GGTNKRAPWT PARFSGSLLG GKAALTITGA
QAEDEADYYC ALWYSNLWVF GGGTKLTVLG GGGSGGGGQV
QLKQSGPGLV QPSQSLSITC TVSGFSLTNY GVHWVRQSPG
KGLEWLGVIW SGGNTDYNTP FTSRLSINKD NSKSQVFFKM
NSLQSNDTAI YYCARALTYY DYEFAYWGQG TLVTVSSGGC
GGGEVAALEK EVAALEKEVA ALEKEVAALE K
```

Amino acid sequence of the EGFRVL-hXR32VH-K coil of the ERBITUX™-h-mAb2 DART™ diabody (the linkers between the EGFRVL sequence and the hXR32VH sequence and between the hXR32VH sequence and the K coil sequence are underlined) (SEQ ID NO:63):

```
DILLTQSPVI LSVSPGERVS FSCRASQSIG TNIHWYQQRT
NGSPRLLIKY ASESISGIPS RFSGSGSGTD FTLSINSVES
EDIADYYCQQ NNNWPTTFGA GTKLELKGGG SGGGGEVQLV
ESGGGLVQPG GSLRLSCAAS GFTFNTYAMN WVRQAPGKGL
EWVARIRSKY NNYATYYADS VKDRFTISRD DSKNSLYLQM
NSLKTEDTAV YYCVRHGNFG NSYVSWFAYW GQGTLVTVSS
GGCGGGKVAA LKEKVAALKE KVAALKEKVA ALKE
```

Figure 10A:
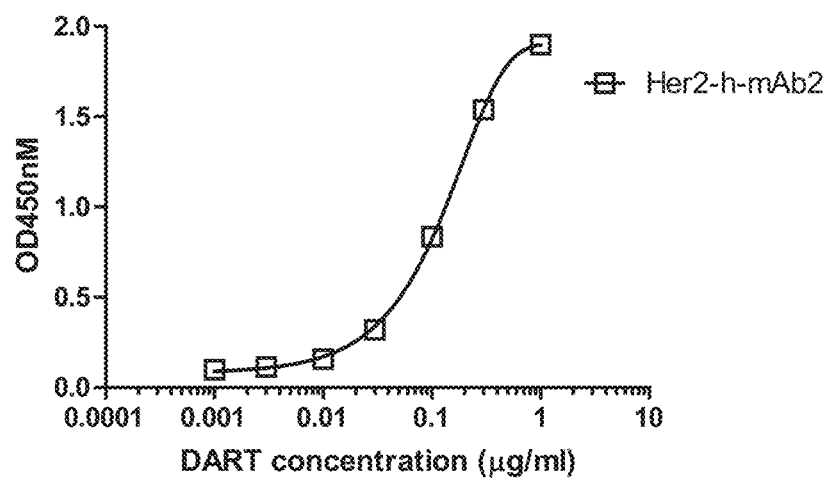
FIGS. 10A-10D show the results of capture ELISAs performed on DART™ diabodies having an anti-CD3 first epitope binding site and second epitope binding site that bind to either Her2/neu, CD19, EGFR, or B7-H3.
Figure 10B:
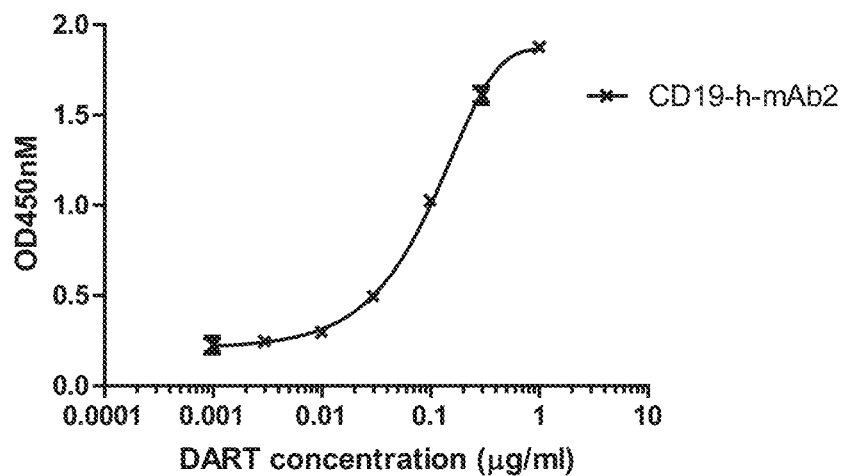
Figure 10C:
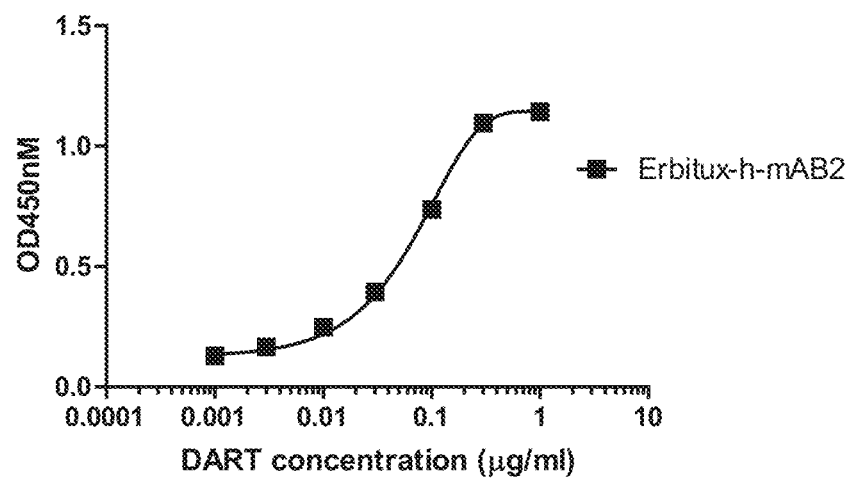

Such DART™ diabodies were found to be capable of binding to cynomolgus monkey CD3 (FIGS. 10A-10C).

The CDRs of humanized mAb2 (h-mAb2) were used to produce a further series of DART™ diabodies having an anti-CD3 first epitope binding site and a second epitope binding site capable of binding to B7-H3 (DART™ diabody "B7-H3-1-h-mAb2" and B7-H3-2-h-mAb2").

B7-H3-1-h-mAb2 DART™ Diabody

Amino acid sequence of the hBRCA69DVL-hXR32VH-E coil of the B7-H3-1-h-mAb2 DART™ diabody (the linkers between the hBRCA69DVL sequence and the hXR32VH sequence and between the hXR32VH sequence and the E coil sequence are underlined) (SEQ ID NO:64):

```
DIQMTQSPSS LSASVGDRVT ITCRASQDIS NYLNWYQQKP
GKAPKLLIYY TSRLHSGVPS RFSGSGSGTD FTLTISSLQP
EDIATYYCQQ GNTLPPTFGG GTKLEIKGGG GSGGGGEVQL
VESGGGLVQP GGSLRLSCAA SGFTFNTYAM NWVRQAPGKG
LEWVARIRSK YNNYATYYAD SVKDRFTISR DDSKNSLYLQ
MNSLKTEDTA VYYCVRHGNF GNSYVSWFAY WGQGTLVTVS
SGGCGGGEVA ALEKEVAALE KVAALEKEV AALEK
```

Amino acid sequence of the hXR32VL-hBRCA69DVH-K coil of the B7-H3-1-h-mAb2 DART™ diabody (the linkers between the hXR32VL sequence and the hBRCA69DVH sequence and between the hBRCA69DVH sequence and the K coil sequence are underlined) (SEQ ID NO:65):

```
QAVVTQEPSL TVSPGGTVTL TCRSSTGAVT TSNYANWVQQ
KPGQAPRGLI GGTNKRAPWT PARFSGSLLG GKAALTITGA
QAEDEADYYC ALWYSNLWVF GGGTKLTVLG GGGSGGGGQV
QLVQSGAEVK KPGASVKVSC KASGYTFTSY WMQWVRQAPG
QGLEWMGTIY PGDGDTRYTQ KFKGRVTITA DKSTSTAYME
LSSLRSEDTA VYYCARRGIP RLWYFDVWGQ GTTVTVSSGG
CGGGKVAALK EKVAALKEKV AALKEKVAAL KE
```

B7-H3-2-h-mAb2 DART™ Diabody

Amino acid sequence of the hBRCA84DVL-hXR32VH-E coil of the B7-H3-2-h-mAb2 DART™ diabody (the linkers between the hBRCA84DVL sequence and the hXR32VH sequence and between the hXR32VH sequence and the E coil sequence are underlined) (SEQ ID NO:66):

```
DIQLTQSPSF LSASVGDRVT ITCKASQNVD TNVAWYQQKP
GKAPKALIYS ASYRYSGVPS RFSGSGSGTD FTLTISSLQP
EDFATYYCQQ YNNYPFTFGQ GTKLEIKGGG GSGGGGEVQL
VESGGGLVQP GGSLRLSCAA SGFTFNTYAM NWVRQAPGKG
LEWVARIRSK YNNYATYYAD SVKDRFTISR DDSKNSLYLQ
MNSLKTEDTA VYYCVRHGNF GNSYVSWFAY WGQGTLVTVS
SGGCGGGEVA ALEKEVAALE KVAALEKEV AALEK
```

Amino acid sequence of the hXR32VL-hBRCA84DVH-K coil of the B7-H3-2-h-mAb2 DART™ diabody (the linkers between the hXR32VL sequence and the hBRCA84DVH sequence and between the hBRCA84DVH sequence and the K coil sequence are underlined) (SEQ ID NO:67):

```
QAVVTQEPSL TVSPGGTVTL TCRSSTGAVT TSNYANWVQQ
KPGQAPRGLI GGTNKRAPWT PARFSGSLLG GKAALTITGA
QAEDEADYYC ALWYSNLWVF GGGTKLTVLG GGGSGGGGEV
QLVESGGGLV QPGGSLRLSC AASGFTFSSF GMHWVRQAPG
KGLEWVAYIS SDSSAIYYAD TVKGRFTISR DNAKNSLYLQ
MNSLRDEDTA VYYCGRGREN IYYGSRLDYW GQGTTVTVSS
GGCGGGKVAA LKEKVAALKE KVAALKEKVA ALKE
```

Figure 10D:
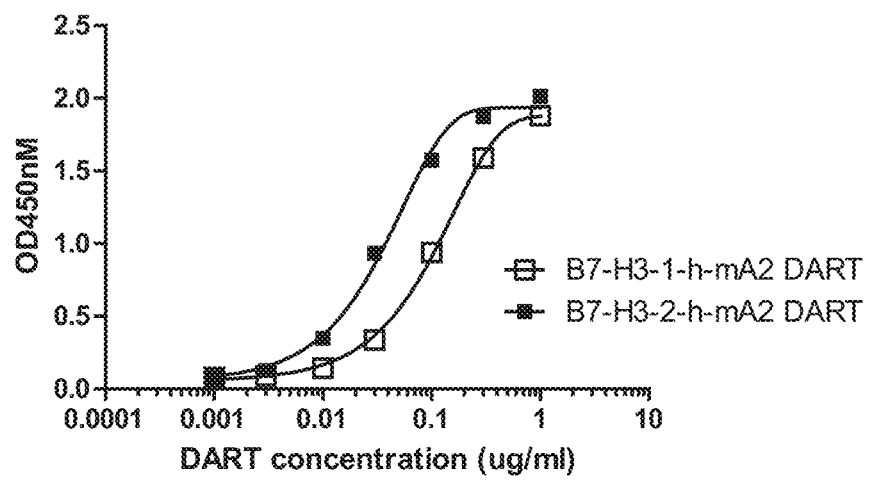

Such DART™ diabodies were found to be capable of binding to soluble cynomolgus monkey CD3 (FIG. 10D).

Example 9

Dual Affinity Retargeting Reagents (DART™s) Diabodies Specific For HER2/neu and CD3 Mediate Potent Redirected T-Cell Killing Dual affinity retargeting reagent (DART™) diabodies specific for HER2/neu and CD3 are prepared. Such DART™ diabodies have the ability to localize a T-cell (by binding such T-cell to the CD3-binding portion of a CD3-binding DART™ diabody) to the location of a tumor cell (by binding such cancer cell to the HER2/neu-binding portion of the DART™ diabody). The localized T-cell can then mediate the killing of the tumor cell in a process termed herein "redirected" killing.

The dual affinity retargeting reagent (DART™) diabody specific for HER2/neu and CD3 is constructed having the anti-HER2/neu variable domains of trastuzumab and anti-CD3 variable domains of h-mab2 VH-8 and h-mab2 VL-6 (SEQ ID NOs: 58-59).

In order to demonstrate the ability of DART™ diabodies to mediate such redirected killing of cancer cells, the above-described HER2/neu×CD3 DART™ diabody is incubated at various concentrations with target tumor cells (SKOV-3 tumor cells, SKBR-3 tumor cells, A549 tumor cells, and MCF-7 tumor cells) and effector resting PBMC (E:T ratio=30:1) and cytotoxicity is determined (LDH Assay). The results of these investigations demonstrate the ability of the HER2/neu×CD3 DART™ diabody to mediate redirected killing of tumor cells.

Example 10

Anti-TCR Monoclonal Antibody Therapy for Patients with Autoimmune Diabetes

Patients: Forty patients with Type 1 diabetes are recruited for participation according to the following criteria: between 7 and 20 years of age, within 6 weeks of diagnosis according to the American Diabetes Association criteria, and confirmation of the presence of anti-GAD65, anti-ICA512, and/or anti-insulin autoantibodies. The patients remain under the care of their personal physicians during the course of the study.

Eligible patients are randomly assigned to a control group and a humanized anti-CD3 antibody (N297Q) (comprising h-mab2 VH-8 and h-mab2 VL-6) treatment group. After randomization, blood samples are drawn to establish baseline HA1c levels, a pretreatment C-peptide response to a MMTT is established and a pretreatment FPIR to IGTT is performed. Patients in both groups are hospitalized to receive either a 6-day course treatment of the humanized anti-CD3 monoclonal antibody (N297Q) or placebo. The antibody is administered intravenously in the following dosage: 17 µg/m² on day 1, 34.3 µg/m² on day 2, 69 µg/m² on day 3, 137.6 µg/m² on day 4, and 275.3 µg/m² on days 5 and 6. Alternatively, antibody may be administered intravenously in the following dosage: 1.6 µg/kg/day on day 1; 3.2 µg/kg/day on day 2; 6.5 µg/kg/day on day 3; 13 µg/kg/day on day 4; and 26 µg/kg/day on days 5 through 14. In dose escalation studies, the treatment may be, e.g., 1.42 µg/kg/day on day 1; 5.7 µg/kg/day on day 2; 11 µg/kg/day on day 3; 26 µg/kg/day on day 4; and 45.4 µg/kg/day on days 5 through 14. In subsequent studies, the therapy is altered to increase dosage and/or decrease the time course of treatment. For example, in subsequent studies patients may be administered a 4 day treatment: 6.4 µg/kg/day on day 1; 13 µg/kg/day on day 2, and 26 µg/kg/day on days 3 and 4.; during additional dose escalation studies, the treatment may be 8 µg/kg/day on day 1; 16 µg/kg/day on day 2; and 32 µg/kg/day on days 3 and 4.

During initial studies the antibody dosage on the first three days of treatment is administered via slow infusion IV over 20 hours to monitor for adverse reactions. Subsequent studies will decrease the time of administration and/or split the dosage into 2 to 4 equal parts to be administered as bolus injections evenly distributed over the course of 12 hours. Patients in the control group undergo metabolic and immunologic tests but do not receive monoclonal antibodies. Patients are monitored throughout the study for immunosuppressive effects of the anti-CD3 monoclonal antibody (N297Q).

Patients are monitored for 18 months after the treatment. R-cell function is determined every 6 months in the case of impaired glucose tolerance and every 12 months in case of normal glucose tolerance. Patients are allowed to have a normal diet, and remain under the care of their personal physician throughout the duration of the study. Immunological assays are repeated in intervals of 6 months. Insulin therapy will be given to the patients as directed by their personal physician.

β-cell function will be analyzed according to the changes of the C-peptide levels as measured by radioimmunoassay. After drawing samples for baseline C-peptide and glucose, the patients are given a mixed meal. The C-peptide levels are measured in samples drawn after 15, 30, 60, 90, 120, 150, 180, 210, and 240 min. The C-peptide response to the mixed-meal tolerance test (MMTT) is expressed as the total area under the response curve (AUC). A change in the response is considered to have occurred if the response differs by more than 7.5 percent from the response at study entry. The patients' C-peptide responses to MMTT are continuously monitored 6 months, 9 months, 12 months, 15 months and 18 months after the treatment. Alternatively, the β-cell function is assessed by FPIR to IGTT. Serum insulin levels are measured by a modification of a double-antibody radioimmunoassay method using monoiodinated tyrosine A14-labeled insulin (Amersham Pharmacia). FPIR is calculated as the sum of insulin levels at 1 and 3 minutes after a glucose load (0.5 g/kg). Glycosylated hemoglobin levels are measured by latex-agglutination inhibition test.

Immunological Monitoring: The level of autoantibodies against GAD65, IA2/ICA512, and insulin are measured with radiobinding assays as known in the art (e.g., Woo et al., 2000, J. Immunol Methods 244:91-103). HLA-DQA and HLA-DQB genotyping are performed by direct sequencing of exon 2 polymorphisims after PCR amplification. The level of cytokines in serum after the administration of the monoclonal antibody is measured by enzyme-linked immunosorbent assay (ELISA). Production of anti-idiotype antibodies is monitored by ELISA assay using a plate bound anti-CD3 (N297Q) or by flow cytometry to measure blockade of binding of anti-CD3-FITC to the CD3 chain of TCR.

Statistical Analysis: Data analysis will be conducted on residual beta-cell function, autoantibody level, cytokine level, and glycosylated hemoglobin level. A $\chi^2$ analysis will be performed to test the effect of drug treatment before and after drug administration. Comparison between the control group and the treatment group will be made with the Mann-Whitney U test.

Example 11

Dual Affinity Retargeting Reagents (DART™s) Diabodies Specific for B7H3 and CD3 Mediate Potent Redirected T-Cell Killing Dual affinity retargeting reagents (DART™) diabodies specific for the B7H3 antigen and CD3 were prepared. B7H3 has been immunohistologically detected in tumor cell lines (Chapoval, A. et al. (2001) "*B7-H3: A Costimulatory Molecule For T Cell Activation and IFN-γ Production*," Nature Immunol. 2:269-274; Saatian, B. et al. (2004) "*Expression Of Genes For B7-H3 And Other T Cell Ligands By Nasal Epithelial Cells During Differentiation And Activation*," Amer. J. Physiol. Lung Cell. Mol. Physiol. 287:L217-L225; Castriconi et al. (2004) "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34):12640-12645); Sun, M. et al. (2002) "*Characterization of Mouse and Human B7-H3 Genes*," J. Immunol. 168:6294-6297). Several independent studies have shown that human malignant tumor cells exhibit a marked increase in expression of B7-H3 protein and that this increased expression was associated with increased disease severity (Zang, X. et al. (2007) "*The B7 Family And Cancer Therapy: Costimulation And Coinhibition*," Clin. Cancer Res. 13:5271-5279), suggesting that B7-H3 is exploited by tumors as an immune evasion pathway (Hofmeyer, K. et al. (2008) "*The Contrasting Role Of B7-H3*," Proc. Natl. Acad. Sci. (U.S.A.) 105(30):10277-10278).

The CD3 binding portion of such DART™ diabodies was composed of the above-described light and heavy variable regions of humanized anti-CD3 mAb2 (h-mAb2 VH-8 and h-mAb2 VL-6). The B7H3 portion of such DART™ diabodies was composed of hBRCA84D-2 Light Chain and hBRCA84D-2 Heavy Chain (SEQ ID NOs. 64-65).

Such DART™ diabodies have the ability to localize a T-cell (by binding such T-cell to the CD3-binding portion of a CD3-binding DART™ diabody) to the location of a tumor cell (by binding such cancer cell to the B7H3 binding portion of the DART™ diabody). The localized T-cell can then mediate the killing of the tumor cell via the process of "redirected" killing.

In order to demonstrate the ability of such DART™ diabodies to mediate such redirected killing of cancer cells, the DART™ diabody was incubated at various concentrations with target tumor cells (A498 tumor cells, RECA905021E tumor cells) and effector resting PBMC (E:T ratio=30:1) and cytotoxicity was determined (LDH Assay). A DART™ diabody (4420-h-mAb2) having dual specificity for CD3 (h-mAb2) and fluorescein (antibody 4420) was employed as a control.

4420-h-mAb2 DART™ Diabody

Amino acid sequence of the 4420VL-hXR32VH-E coil of the 4420-h-mAb2 DART™ diabody (the linkers between the 4420VL sequence and the hXR32VH sequence and between the hXR32VH sequence and the E coil sequence are underlined) (SEQ ID NO:68):

```
DVVMTQTPFS LPVSLGDQAS ISCRSSQSLV HSNGNTYLRW

YLQKPGQSPK VLIYKVSNRF SGVPDRFSGS GSGTDFTLKI

SRVEAEDLGV YFCSQSTHVP WTFGGGTKLE IKGGGSGGGG

EVQLVESGGG LVQPGGSLRL SCAASGFTFN TYAMNWVRQA

PGKGLEWVAR IRSKYNNYAT YYADSVKDRF TISRDDSKNS

LYLQMNSLKT EDTAVYYCVR HGNFGNSYVS WFAYWGQGTL

VTVSSGGCGG GEVAALEKEV AALEKEVAAL EKEVAALEK
```

Amino acid sequence of the hXR32VL-4420VH-K coil of the 4420-h-mAb2 DART™ diabody (the linkers between the hXR32VL sequence and the 4420VH sequence and between the 4420VH sequence and the K coil sequence are underlined) (SEQ ID NO:69):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGEV

KLDETGGGLV QPGRPMKLSC VASGFTFSDY WMNWVRQSPE

KGLEWVAQIR NKPYNYETYY SDSVKGRFTI SRDDSKSSVY

LQMNNLRVED MGIYYCTGSY YGMDYWGQGT SVTVSSGGCG

GGKVAALKEK VAALKEKVAA LKEKVAALKE
```

Figure 11A:
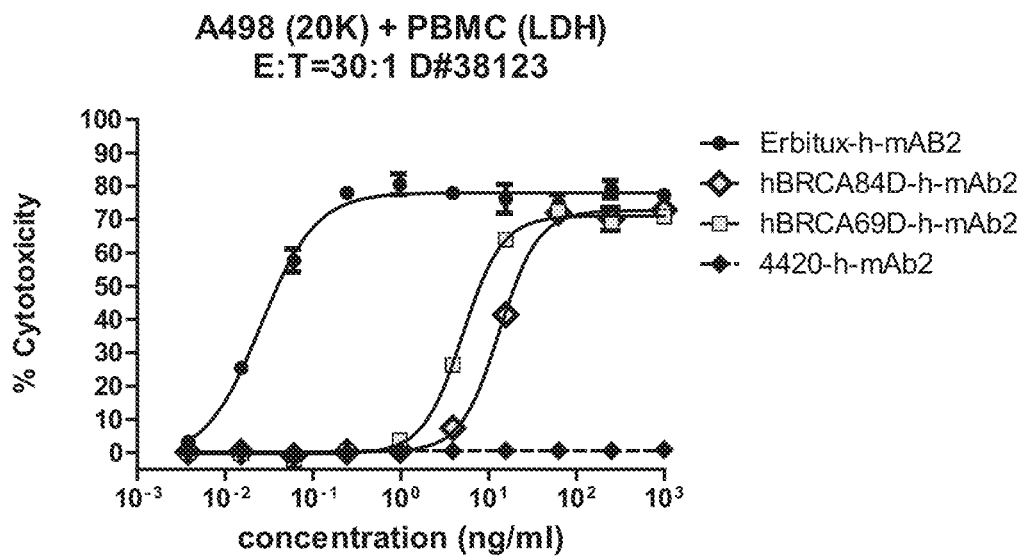
FIGS. 11A-11B show the ability of B7H3×CD3 DART™ diabodies to mediate redirected killing of tumor cells expressing B7H3.
Figure 11B:
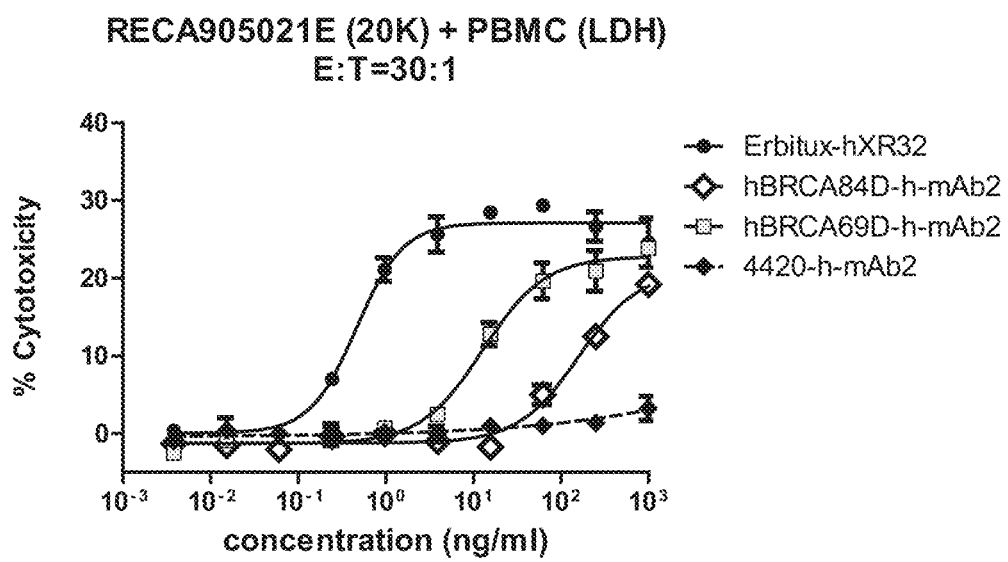
Figure 12A:
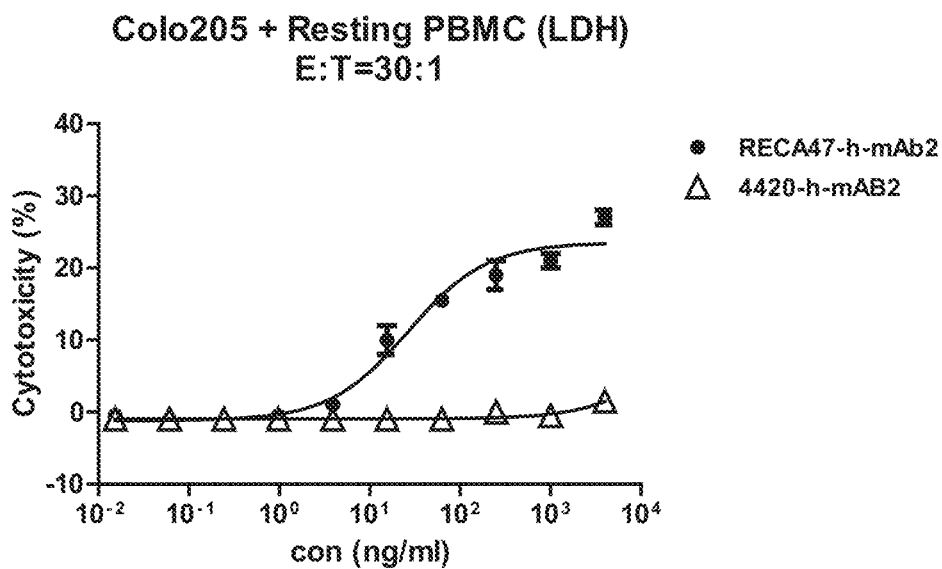
FIGS. 12A-12E show the ability of A33×CD3 DART™ diabodies to mediate redirected killing of tumor cells expressing A33.
Figure 12B:
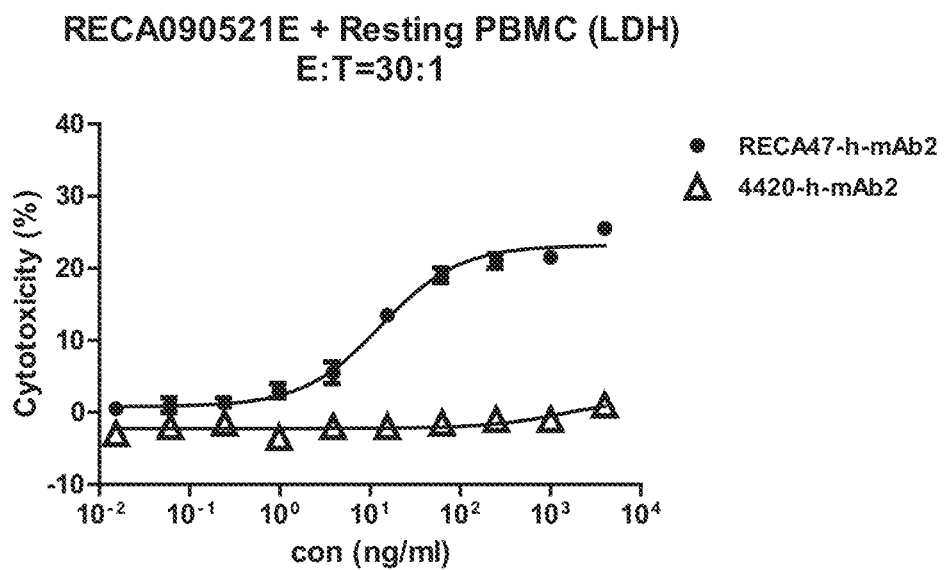
Figure 12C:
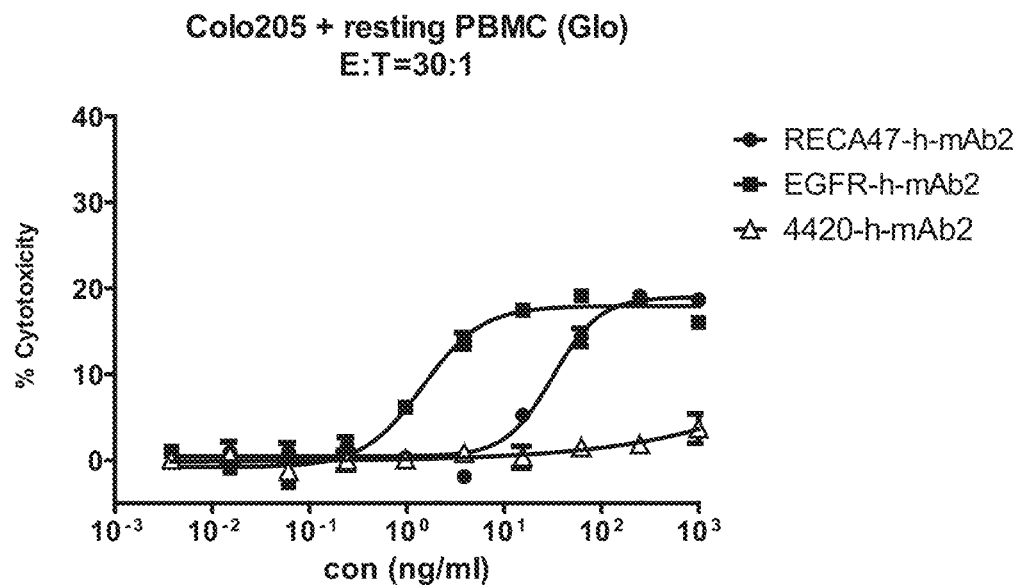
Figure 12D:
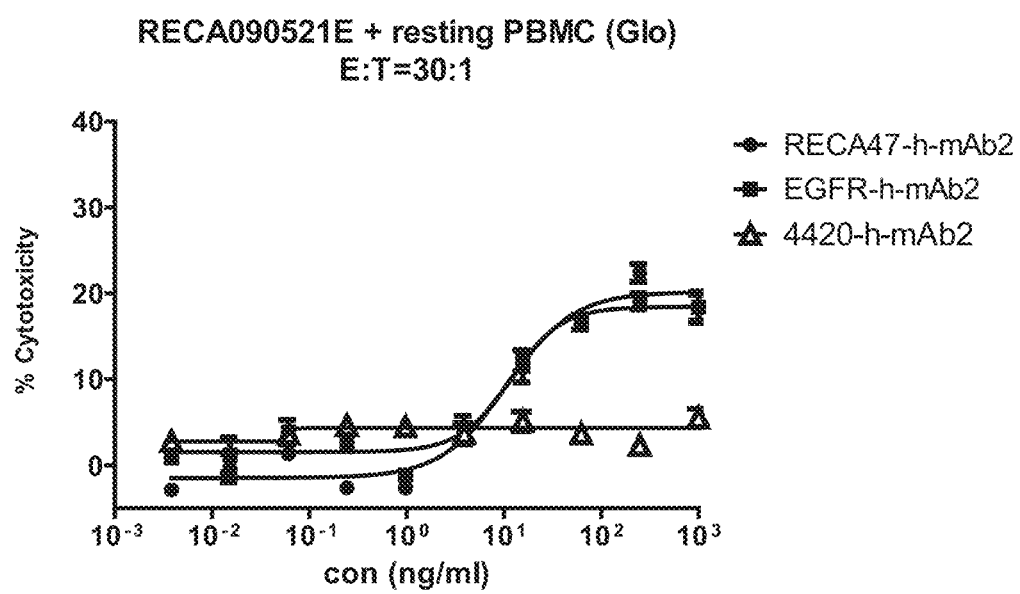
Figure 12E:
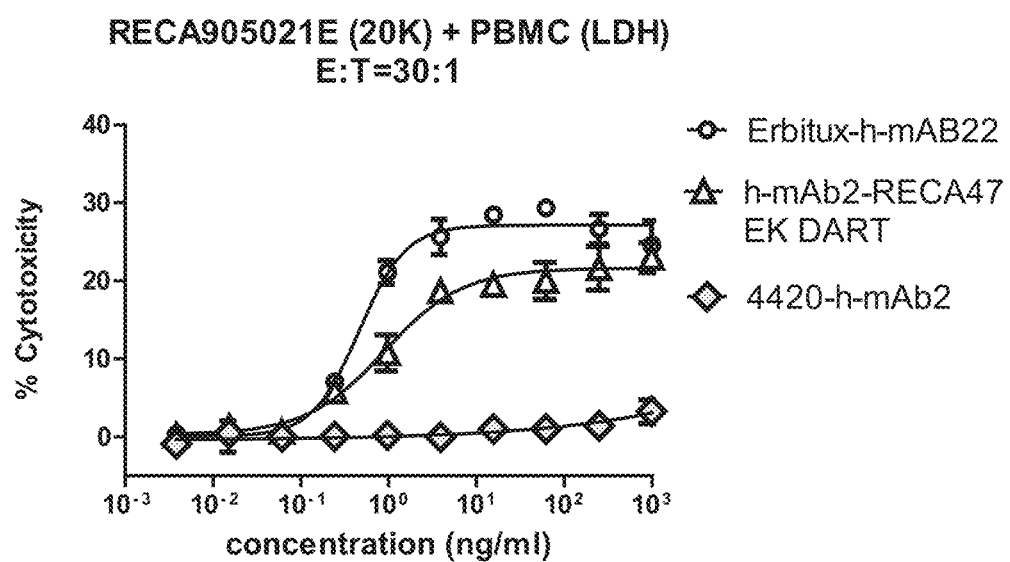

The results of these investigations (FIGS. 11A-11B) demonstrate the ability of the B7H3×CD3 DART™ diabodies to mediate redirected killing of tumor cells expressing B7H3.

Example 12

Dual Affinity Retargeting Reagents (DART™s) Diabodies Specific For A33 and CD3 Mediate Potent Redirected T-Cell Killing Dual affinity retargeting reagents (DART™) diabodies specific for the A33 antigen and CD3 ("A33-h-mAb2" DART™ diabody) were prepared. A33 is a membrane antigen that is expressed in normal human colonic and small bowel epithelium and >95% of human colon cancers (Heath, J. K. et al. (1997) "*The Human A33 Antigen Is A Transmembrane Glycoprotein And A Novel Member Of The Immunoglobulin Superfamily,*" Proc. Natl. Acad. Sci. (USA) 94:469-474).

Such DART™ diabodies have the ability to localize a T-cell (by binding such T-cell to the CD3-binding portion of a CD3-binding DART™ diabody) to the location of a tumor cell (by binding such cancer cell to the A33 binding portion of the DART™ diabody). The localized T-cell can then mediate the killing of the tumor cell via the process of "redirected" killing.

The CD3 binding portion of such DART™ diabodies was composed of the above-described light and heavy variable regions of humanized mAb2 (h-mAb2 VH-8 and h-mAb2 VL-6). The A33 portion of such DART™ diabodies was composed of antibody RECA47.

A33-h-mAb2 DART™ Diabody

Amino acid sequence of the RECA47VL-hXR32VH-K coil of the A33-h-mAb2 DART™ diabody (the linkers between the RECA47VL sequence and the hXR32VH sequence and between the hXR32VH sequence and the K coil sequence are underlined) (SEQ ID NO:70):

```
QIVLTQSPAI MSASPGERVT MTCSARSSIS FMYWYQQKPG

SSPRLLIYDT SNLASGVPVR FSGSGSGTSY SLTISRMEAE

DAATYYCQQW SSYPLTFGSG TKLELKRGGG SGGGGEVQLV

ESGGGLVQPG GSLRLSCAAS GFTFNTYAMN WVRQAPGKGL

EWVARIRSKY NNYATYYADS VKDRFTISRD DSKNSLYLQM

NSLKTEDTAV YYCVRHGNFG NSYVSWFAYW GQGTLVTVSS

GGCGGGKVAA LKEKVAALKE KVAALKEKVA ALKE
```

Amino acid sequence of the hXR32VL-RECA47VH-E coil of the A33-h-mAb2 DART™ diabody (the linkers between the hXR32VL sequence and the RECA47VH sequence and between the RECA47VH sequence and the E coil sequence are underlined) (SEQ ID NO:71):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG GGGSGGGGQV

QLQQSGPELV KPGASVKISC KASGYTFSGS WMNWVKQRPG

QGLEWIGRIY PGDGETNYNG KFKDKATLTA DKSSTTAYME

LSSLTSVDSA VYFCARIYGN NVYFDVWGAG TTVTVSSGGC

GGGEVAALEK EVAALEKEVA ALEKEVAALE K
```

In order to demonstrate the ability of such DART™ diabodies to mediate such redirected killing of cancer cells, the DART™ diabody was incubated at various concentrations with target tumor cells (Colo205 tumor cells, RECA905021E tumor cells) and effector resting PBMC (E:T ratio=30:1) and cytotoxicity was determined (LDH Assay). The results of these investigations (FIGS. 12A-12E) demonstrate the ability of the A33×CD3 DART™ diabodies to mediate redirected killing of tumor cells expressing A33.

Example 13

Dual Affinity Retargeting Reagents (DART™s) Diabodies Specific For CD3 Cause Redirected T-Cell-Mediated Killing Equivalent to That of Other Human-Specific CD3 Diabodies In order to further assess the CD3-specific dual affinity retargeting reagents (DART™) diabodies of the present invention, the capacity of the above-described CD19-h-mAb2 DART™ diabody to cause redirected T-cell-mediated killing was compared to that of the CD19×CD3 DART diabody of Moore, P. A. et al. (2011) ("*Application Of Dual Affinity Retargeting Molecules To Achieve Optimal Redirected T-Cell Killing Of B-Cell Lymphoma,*" Blood 117(17): 4542-4551). The CD19-h-mAb2 DART™ diabody exhibits specificity to human as well as non-human CD3; the CD19×

CD3 DART diabody of Moore, P. A. et al. (2011)) exhibits specificity only to human CD3.

Figure 13A:
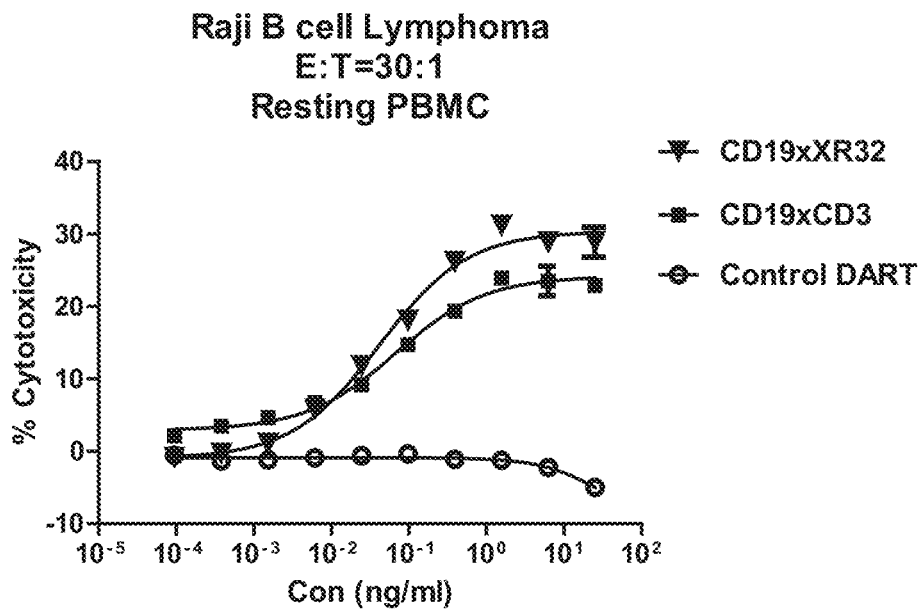
FIGS. 13A and 13B show the results of a comparison of the capacity of a CD19-h-mAb2 DART™ and a CD19×CD3 DART diabody to cause redirected T-cell-mediated killing. The CD19-h-mAb2 DART™ diabody exhibits specificity to human as well as non-human CD3; the CD19×CD3 DART diabody o exhibits specificity only to human CD3.
Figure 13B:
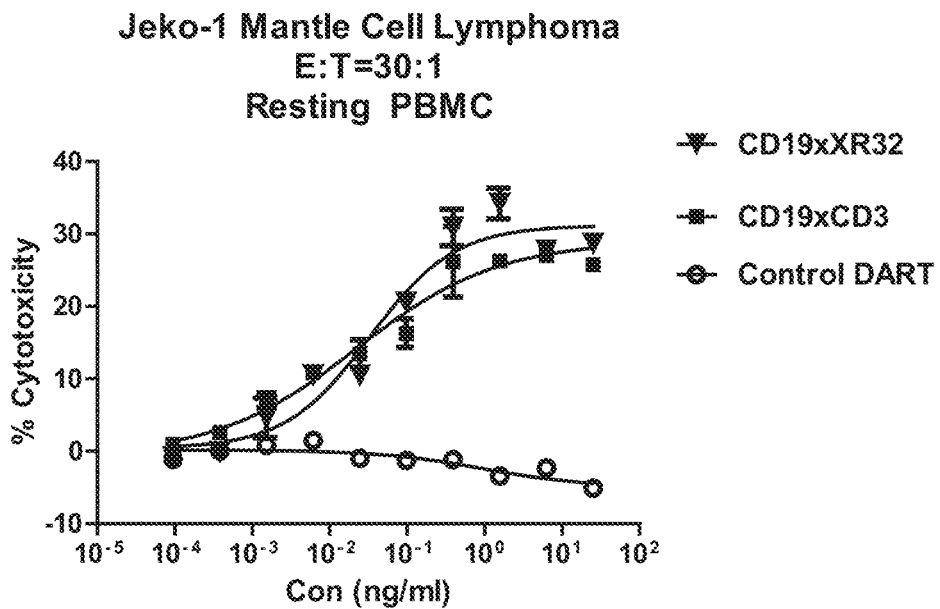

Accordingly, Raji human B-cell lymphoma cells (see, Drexler, H. G. et al. (1998) "*History And Classification Of Human Leukemia-Lymphoma Cell Lines*," Leuk. Lymphoma 31(3-4):305-316; Arndt, R. (1984) "*Demonstration Of C3-Binding Circulating Immune Complexes Using Raji, Conglutinin And Anti-C3 Assays—A Critical Review*," Immun. Infekt. 12(1):3-11) or JeKo-1 human mantle cell lymphoma cells (Salaverria, I. et al. (2006) "*Mantle Cell Lymphoma: From Pathology And Molecular Pathogenesis To New Therapeutic Perspectives*," Haematologica 91:11-16; Jeon, H. J. et al. (1998) "*Establishment And Characterization Of A Mantle Cell Lymphoma Cell Line*," Br. J. Haematol. 102(5):1323-1326) were incubated in the presence of a DART™ diabody and resting peripheral blood mononuclear cells (PBMC) (E:T=30:1). The results of this experiment (FIGS. 13A and 13B) revealed that the CD19-h-mAb2 DART™ diabody of the present invention cause redirected T-cell-mediated killing that was equivalent to that observed using a CD19×CD3 DART diabody specific for human CD3. Thus the extension of specificity to non-human CD3 hololgs did not impair the ability of the DART™ diabody to mediate redirected killing.

Example 14

Redirected Cytolysis by Cynomolgus Monkey Cross Reactive Dual Affinity Retargeting Reagents (DART™s) Diabodies Specific For CD3

The ability of the above-described CD19-h-mAb2 DART™ diabody to cause redirected T-cell-mediated killing in the presence of either human or cynolmolgus monkey was investigated.

Figure 14A:
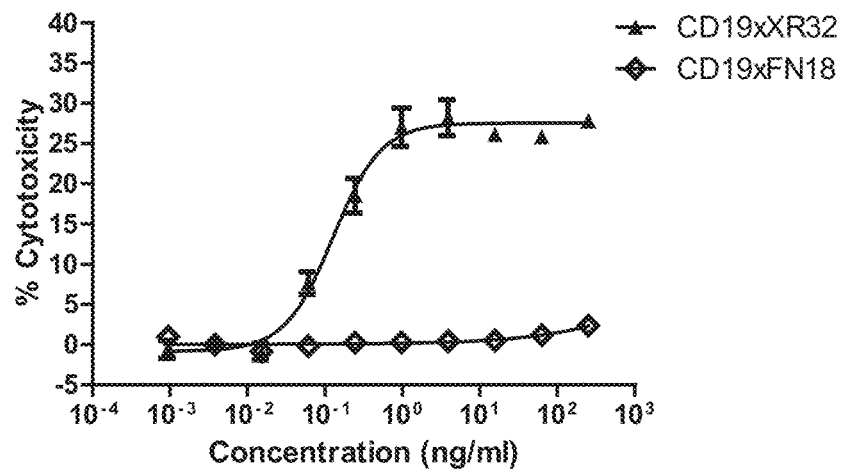
FIGS. 14A and 14B show that the CD19-h-mAb2 DART™ diabody of the present invention was able to mediate cytolysis in the presence of either human or non-human T-cell effector cells.
Figure 14B:
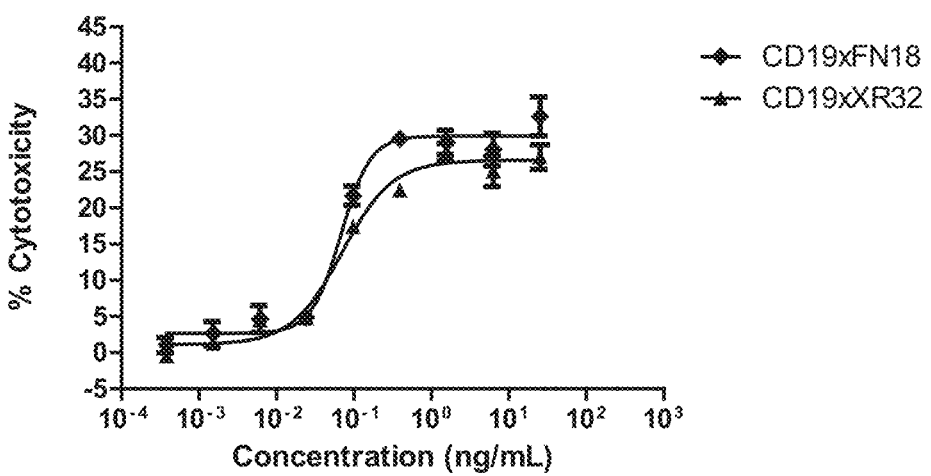

HT-29 human colon cancer cells (Marchis-Mouren, G. et al. (1988) "HT 29, A Model Cell Line: Stimulation By The Vasoactive Intestinal Peptide (VIP); VIP Receptor Structure And Metabolism," Biochimie 70(5):663-671); Fogh, J. et al. (1975) In: J. Fogh (ed.), HUMAN TUMOR CELLS IN VITRO, New York: Plenum Press. 1975) were incubated in the presence of human or cynolmolgus monkey T-cells (E:T ratio=30:1) and either the above-described CD19-h-mAb2 DART™ diabody or a CD19×CD3 DART diabody whose CD3 sequences were derived from antibody FN-18. Antibody FN-18 exhibits specificity only to cynolmolgus monkey CD3 (Nooij, F. J. et al. (1986) "*Differentiation Antigens On Rhesus Monkey Lymphocytes. I. Identification Of T Cells Bearing CD3 And CD8, And Of A Subset Of CD8-Bearing Cells*," Eur. J. Immunol. 16(8):975-979; Meng, G. et al. (1998) "*The Effect Of Anti-CD3-Immunotoxin On T Lymphocyte Function in vitro*," Transpl. Immunol. 6(1):53-59). The resultant percent cytotoxicity as a function of diabody concentration was measured. The results (FIGS. 14A and 14B) show that the CD19-h-mAb2 DART™ diabody was able to mediate cytolysis in the presence of either human or non-human T-cell effector cells. In contrast, the FN-18 diabody was capable of mediating cytolysis only in the presence of cynolmolgus monkey T-cells.

Example 15

Dual Affinity Retargeting Reagents (DART™s) Diabodies Require Target Cell Engagement In order to demonstrate that the observed redirected killing mediated by the CD3 DART™ diabodies of the present invention was specific, the extent of killing in the presence and absence of target cells was determined.

Human PMBCs were incubated in the presence of the above-described ERBITUX™-h-mAb2 DART™ diabody, an ERBITUX™-T-Cell Receptor DART™ diabody (capable of binding to EGFR (Epidermal Growth Factor Receptor) and the T-cell receptor), or an ERBITUX™-FN18 CD3 DART™ diabody (capable of binding to EGFR and to cynolmolgus monkey CD3). The incubations were conducted in the presence or absence of A498 kidney cancer target cells (Giard, D. J. et al. (1973) "*in vitro Cultivation Of Human Tumors: Establishment Of Cell Lines Derived From A Series Of Solid Tumors*," J. Natl. Cancer Inst. 51:1417-1423; Fogh, J. (1978) "*Cultivation, Characterization, And Identification Of Human Tumor Cells With Emphasis On Kidney, Testis And Bladder Tumors*," Natl. Cancer Inst. Monogr. 49:5-9).

The CD69 glycoprotein is an early activation antigen of T and B lymphocytes that is expressed on cells of most hematopoietic lineages, including neutrophils after stimulation (Atzenia, F. et al. (2002) "*Induction Of CD69 Activation Molecule On Human Neutrophils by GM-CSF, IFN-γ, and IFN-α*," Cellular Immunol. 220(1): 20-29). The CD69 Mean Fluorescent Intensity (MFI) was therefore measured (as a function of diabody concentration) as a means for assessing immune system activation (see, e.g., Ampel, N. M. et al. (2002) "*In Vitro Whole-Blood Analysis of Cellular Immunity in Patients with Active Coccidioidomycosis by Using the Antigen Preparation T27K*," Clinical Diagnostic Laboratory Immunology 9(5):1039-1043).

Figure 15A:
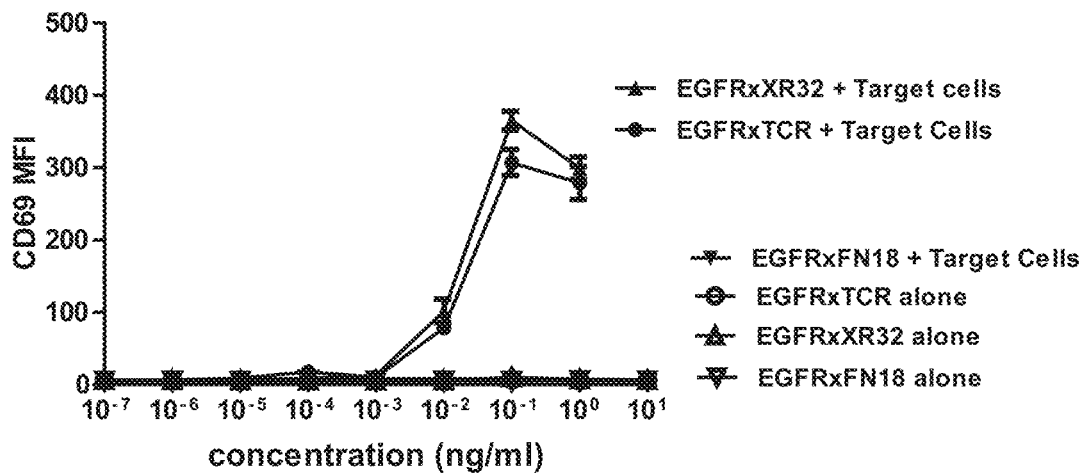
FIGS. 15A and 15B show the ability of the ERBITUX™-h-mAb2 DART™ diabody of the present invention or an ERBITUX™-T-Cell Receptor DART™ diabody to mediate an increase in CD69 MFI upon incubation with CD4+ or CD8+ T cells; A control ERBITUX™-FN18 CD3 DART™ diabody (capable of binding to EGFR and to cynolmolgus monkey CD3) failed to induce an increase in the CD69 MFI.
Figure 15B:
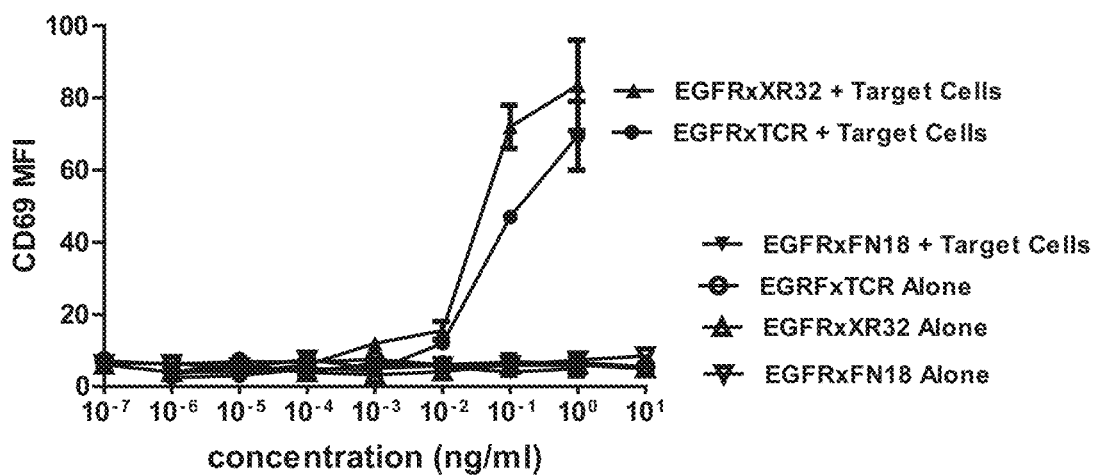

The results (FIGS. 15A and 15B) show that immune system activation (as measured by the MFI of CD69) increased only when CD4+ or CD8+ T cells were incubated with the ERBITUX™-h-mAb2 DART™ diabody of the present invention or an ERBITUX™-T-Cell Receptor DART™ diabody (capable of binding to EGFR and the T-cell receptor). The ERBITUX™-FN18 CD3 DART™ diabody (capable of binding to EGFR and to cynolmolgus monkey CD3) failed to induce an increase in the CD69 MFI.

Example 16

Redirected Killing by Humanized Cynomolgus Monkey/Human Cross-Reactive DART™ Diabodies To further demonstrate the ability of the DART™ diabodies of the present invention to mediate redirected killing, A498 kidney cancer target cells or A431 epidermoid carcinoma cells (Lee, C. M. et al. (2010) "*The Distribution Of The Therapeutic Monoclonal Antibodies Cetuximab And Trastuzumab Within Solid Tumors*," BMC Cancer 10:255; pages 1-11; Bryant, J. A. et al. (2004) "*EGF Activates Intracellular And Intercellular Calcium Signaling By Distinct Pathways In Tumor Cells*," Cancer Biol. Ther. 3(12): 1243-1249) and the extent of redirected killing mediated by various DART™ diabodies in the presence of PMBC effector cells (E:T=30:1) was determined.

Cells were incubated in the presence of either ERBITUX™-h-mAb2 DART™ diabody, ERBITUX™-m-mAb2 DART™ diabody or 4420-h-mAb2 DART™ diabody (negative control) or a control secondary antibody. Binding to target cells was determined by measuring MFI. Redirected killing was assessed by measuring the % cytotoxicity.

The results of this investigation are shown in FIGS. 16A-16D. Diabodies having specificity for CD3 and EGFR were found to be able to bind to A498 or A431 cells (FIGS.

Figure 16A:
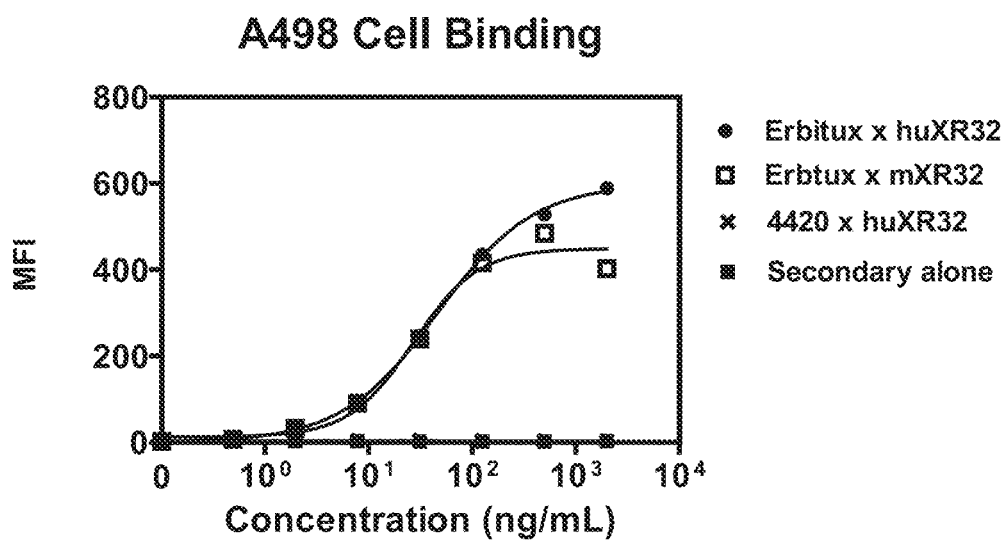
FIGS. 16A-16D show the results of investigations into the binding of either ERBITUX™-h-mAb2 DART™ diabody, ERBITUX™-m-mAb2 DART™ diabody or 4420-h-mAb2 DART™ diabody (negative control) or a control secondary to A498 or A431 cells (FIGS. 16A and 16C, respectively), and to mediate redirected killing of such cells (FIGS. 16B and 16D, respectively).
Figure 16B:
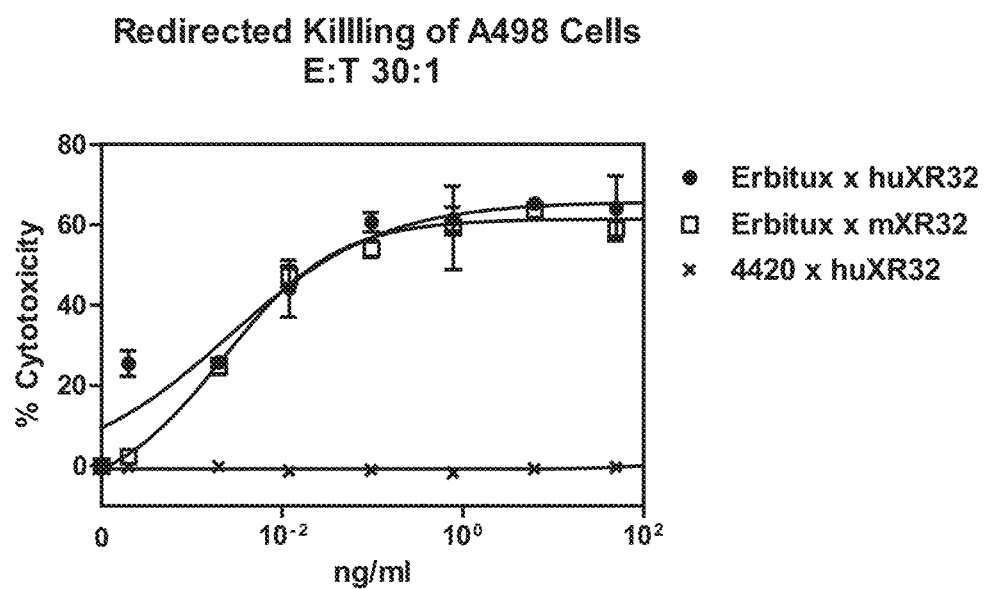
Figure 16C:
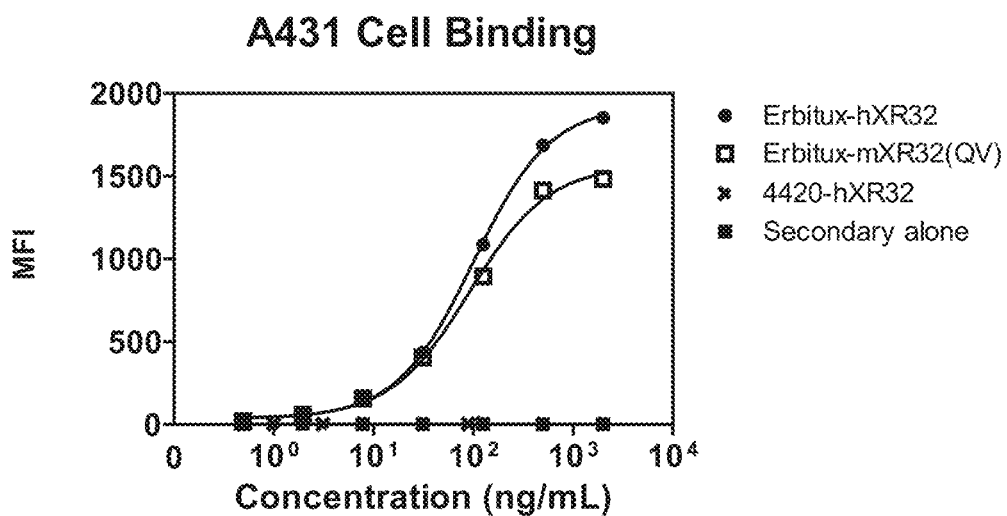
Figure 16D:
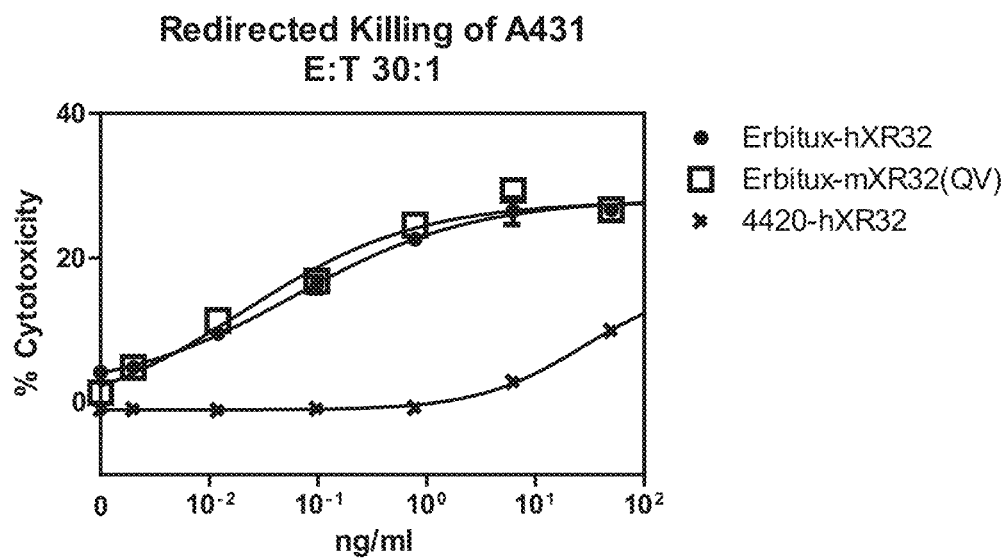

16A and 16C, respectively), and to mediate redirected killing of these cells (FIGS. 16B and 16D, respectively).

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of treating cancer, comprising administering an effective amount of a CD3-binding molecule to a subject in need thereof, wherein said CD3-binding molecules comprises an antigen-binding fragment of an antibody, wherein said antigen-binding fragment comprises an antibody CD3-specific VL domain and an antibody CD3-specific VH domain, wherein said CD3-specific VL domain and said CD3-specific VH domain form an antigen-binding domain capable of immunospecifically binding to both an epitope of human CD3 and to an epitope of the CD3 of a non-human mammal, wherein:

(I) said CD3-specific VL domain comprises the three complementarity determining regions (CDRs) of SEQ ID NO:5; and (II) said CD3-specific VH domain comprises the three complementarity determining regions (CDRs) of SEQ ID NO:7, modified to comprise an amino acid substitution of D65G;

wherein said numbering is according to the Kabat numbering scheme.

2. The method of claim 1, wherein said CD3-specific VL domain is selected from the group consisting of h-mab2 VL-4 (SEQ ID NO:22), h-mab2 VL-6 (SEQ ID NO:26), h-mab2 VL-7 (SEQ ID NO:28), h-mab2 VL-8 (SEQ ID NO:30), h-mab2 VL-9 (SEQ ID NO:32), and h-mab2 VL-10 (SEQ ID NO:34).

3. The method of claim 1, wherein said CD3-specific VH domain is selected from the group consisting of h-mab2 VH-6L (SEQ ID NO:54), h-mab2 VH-8L (SEQ ID NO:55), h-mab2 VH-8 di-1 (SEQ ID NO:56), h-mab2 VH-8 di-2

(SEQ ID NO:57), h-mab2 VH-6M (SEQ ID NO:72), h-mab2 VH-8M (SEQ ID NO:74), h-mab2 VH-2k (SEQ ID NO:87), and h-mab2 VH-5k (SEQ ID NO:88).

4. The method of claim 1, wherein said CD3-specific VH domain comprises an amino acid sequence that differs, by comprising said amino acid substitution, from the amino acid sequence of h-mab2 VH-1 (SEQ ID NO:36), h-mab2 VH-2 (SEQ ID NO:38), h-mab2 VH-3 (SEQ ID NO:40), h-mab2 VH-4 (SEQ ID NO:42), h-mab2 VH-5 (SEQ ID NO:44), h-mab2 VH-6 (SEQ ID NO:46), h-mab2 VH-7 (SEQ ID NO:48), and h-mab2 VH-8 (SEQ ID NO:50).

5. The method of claim 1, wherein said CD3-binding molecule is an antibody.

6. The method of claim 5, wherein said antibody:
(A) lacks an Fc region;
or
(B) comprises an Fc region that:
  (i) lacks effector function; or
  (ii) has reduced effector function; or
  (iii) impairs the ability of the Fc region of said antibody to bind to an Fc receptor;
wherein said lack of effector function, said reduction in effector function, and said impairment of binding ability is relative to that of a wild-type Fc receptor.

7. The method of claim 1, wherein said CD3-binding molecule is humanized.

8. The method of claim 1, which is capable of immunospecifically binding to both: (i) CD3 and (ii)(a) a tumor antigen, or (ii)(b) a cell surface antigen, receptor or receptor ligand.

9. The method of claim 8, wherein said CD3-binding molecule is capable of immunospecifically binding to CD3 and to a tumor antigen expressed on a tumor cell, wherein said tumor cell is a tumor cell from a cancer selected from the group consisting of: breast cancer, prostate cancer, gastric cancer, lung cancer, stomach cancer, colon cancer, rectal cancer, pancreatic cancer, liver cancer, ovarian cancer, oral cavity cancer, pharyngeal cancer, esophageal cancer, laryngeal cancer, bone cancer, skin cancer, melanoma, uterine cancer, testicular cancer, bladder cancer, kidney cancer, brain cancer, glioblastoma, thyroid cancer, lymphoma, myeloma, and leukemia.

10. The method of claim 8 wherein said CD3-binding molecule is capable of immunospecifically binding to CD3 and to a cell surface antigen, receptor or receptor ligand, wherein said cell surface antigen, receptor or receptor ligand is HER2/neu, B7-H3, CD20, PSMA, IGF-1R, or Ep-CAM.

11. The method of claim 8, wherein said CD3-binding molecule is capable of immunospecifically binding to CD3 and to a cell surface antigen, receptor or receptor ligand, wherein said cell surface antigen, receptor or receptor ligand is a molecule involved in a T cell—B cell association, wherein said molecule involved in said T cell—B cell association is selected from the group consisting of CD19, CD20, CD22, CD23, CD27, CD32B, CD38, CD40, CD79a, CD79b, CD80, CD86, LFA-I, LFA-3 and CFA-I.

12. The method of claim 1, wherein said CD3-binding molecule is a CD3-binding diabody that comprises a first polypeptide chain and a second polypeptide chain, said chains being covalently bonded to one another, wherein:
(I) said first polypeptide chain comprises an amino (N-) terminus and a carboxy (C-) terminus and from N-terminus to C-terminus:
  (i) a domain (A) comprising said CD3-specific VL domain;
  (ii) a domain (B) comprising a binding region of a heavy chain variable domain of a second immunoglobulin (VH2); and
  (iii) a domain (C);
  wherein said domains (A) and (B) do not associate with one another to form an epitope binding site;
and
(II) said second polypeptide chain comprises an amino (N-) terminus and a carboxy (C-) terminus and from N-terminus to C-terminus:
  (i) a domain (D) comprising a binding region of a light chain variable domain of said second immunoglobulin (VL2);
  (ii) a domain (E) comprising said CD3-specific VH domain;
  and
  (iii) a domain (F);
  wherein said domains (D) and (E) do not associate with one another to form an epitope binding site; and
wherein:
(1) said domains (A) and (E) associate to form said antigen-binding domain that is capable of immunospecifically binding to both human CD3 and to the CD3 of a non-human mammal;
(2) said domains (B) and (D) associate to form a binding site that immunospecifically binds to a second epitope, said second epitope being different from the CD3 epitope bound by the antigen-binding domain formed from said association of said domains (A) and (E); and
(3) said domains (C) and (F) are covalently associated together.

13. The method of claim 12, wherein said second epitope is not an epitope of CD3.

14. The method of claim 12, wherein said second epitope is an epitope of CD3 that is different from the CD3 epitope bound by the antigen-binding domain formed from said association of said domains (A) and (E).

15. The method of claim 12, wherein said CD3-binding molecule is humanized.

16. The method of claim 12, which is capable of immunospecifically binding to both: (i) CD3 and (ii)(a) a tumor antigen, or (ii)(b) a cell surface antigen, receptor or receptor ligand.

17. The method of claim 16, wherein said CD3-binding molecule is capable of immunospecifically binding to CD3 and to a tumor antigen expressed on a tumor cell, wherein said tumor cell is a tumor cell from a cancer selected from the group consisting of: breast cancer, prostate cancer, gastric cancer, lung cancer, stomach cancer, colon cancer, rectal cancer, pancreatic cancer, liver cancer, ovarian cancer, oral cavity cancer, pharyngeal cancer, esophageal cancer, laryngeal cancer, bone cancer, skin cancer, melanoma, uterine cancer, testicular cancer, bladder cancer, kidney cancer, brain cancer, glioblastoma, thyroid cancer, lymphoma, myeloma, and leukemia.

18. The method of claim 16, wherein said CD3-binding molecule is capable of immunospecifically binding to CD3 and to a cell surface antigen, receptor or receptor ligand, wherein said cell surface antigen, receptor or receptor ligand is HER2/neu, B7-H3, CD20, PSMA, IGF-1R, or Ep-CAM.

19. The method of claim 16, wherein said CD3-binding molecule is capable of immunospecifically binding to CD3 and to a cell surface antigen, receptor or receptor ligand, wherein said cell surface antigen, receptor or receptor ligand is a molecule involved in a T cell—B cell association, wherein said molecule involved in said T cell—B cell association is selected from the group consisting of CD19, CD20, CD22, CD23, CD27, CD32B, CD38, CD40, CD79a, CD79b, CD80, CD86, LFA-I, LFA-3 and CFA-I.

20. The method of claim 12, wherein:
   (A) said domain (B) comprises amino acid residues 119-238 of SEQ ID NO: 65; and
   (B) said domain (D) comprises amino acid residues 1-107 of SEQ ID NO: 64.

21. The method of claim 12, wherein:
   (A) said domain (B) comprises amino acid residues 119-240 of SEQ ID NO: 67; and
   (B) said domain (D) comprises amino acid residues 1-107 of SEQ ID NO: 66.

22. The method of claim 12, wherein said CD3-specific VL domain comprises the amino acid sequence of SEQ ID NO:26.

23. The method of claim 12, wherein said CD3-binding diabody comprises an Fc domain or portion thereof.

24. The method of claim 23, wherein:
   (A) said first polypeptide chain additionally comprises an E coil sequence and said second polypeptide chain additionally comprises a K coil sequence; or
   (B) said first polypeptide chain additionally comprises a K coil sequence and said second polypeptide chain additionally comprises an E coil sequence;
   wherein said E coil sequence is amino acid residues 244-271 of SEQ ID NO: 62, and said K coil sequence is residues 247-274 of SEQ ID NO: 63.

25. The method of claim 13, wherein:
   (A) said first polypeptide chain additionally comprises an E coil sequence and said second polypeptide chain additionally comprises a K coil sequence; or
   (B) said first polypeptide chain additionally comprises a K coil sequence and said second polypeptide chain additionally comprises an E coil sequence;
   wherein said E coil sequence is amino acid residues 244-271 of SEQ ID NO: 62, and said K coil sequence is residues 247-274 of SEQ ID NO: 63.

* * * * *

SEQUENCE LISTING

```
<160> NUMBER OF SEQ ID NOS: 88

<210> SEQ ID NO 1
<211> LENGTH: 107
<212> TYPE: PRT
<213> ORGANISM: Mus musculus

<400> SEQUENCE: 1

Gln Val Val Leu Thr Gln Ser Pro Ala Ile Met Ser Ala Phe Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Ser Arg Asn Pro Pro Thr
                85                  90                  95

Phe Gly Gly Gly Thr Lys Leu Gln Ile Thr Arg
            100                 105

<210> SEQ ID NO 2
<211> LENGTH: 321
<212> TYPE: DNA
<213> ORGANISM: Mus musculus

<400> SEQUENCE: 2
caggtggtgc tgacccagtc ccccgccatc atgtccgcct tccccggcga gaaagtgaca        60
atgacctgct ccgcctcctc ctccgtgtcc tacatgaact ggtatcagca gaagtccggc       120
acctccccca gcggtggat  ctacgactcc tccaagctgg cctccggcgt gcccgccaga       180
ttctctggct ccggctccgg caccagctac tccctgacca tctcctccat ggaaaccgag       240
gacgccgcca cctactactg ccagcagtgg tcccggaacc cccctacctt cggcggaggc       300
accaagctgc agatcaccag a                                                 321

<210> SEQ ID NO 3
<211> LENGTH: 121
<212> TYPE: PRT
<213> ORGANISM: Mus musculus

<400> SEQUENCE: 3

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Ser
            20                  25                  30

Thr Met His Trp Val Lys Gln Arg Pro Gly Gln Gly Leu Glu Trp Ile
        35                  40                  45
```

```
Gly Tyr Ile Asn Pro Ser Ser Ala Tyr Thr Asn Tyr Asn Gln Lys Phe
        50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Pro Gln Val His Tyr Asp Tyr Asn Gly Phe Pro Tyr Trp Gly
            100                 105                 110

Gln Gly Thr Leu Val Thr Val Ser Ser
            115                 120
```

```
<210> SEQ ID NO 4
<211> LENGTH: 363
<212> TYPE: DNA
<213> ORGANISM: Mus musculus

<400> SEQUENCE: 4
caggtgcagc tgcagcagtc tggcgccgag ctggccagac ctggcgcctc cgtgaagatg    60
tcctgcaagg cctccggcta caccttcacc cggtccacca tgcactgggt gaaacagcgg   120
cctggacagg gcctggaatg gatcggctac atcaaccccct ccagcgccta caccaactac   180
aaccagaagt tcaaggacaa ggccaccctg accgccgaca gtcctccag caccgcctac   240 atgcagctgt cctccctgac ctccgaggac tccgccgtgt actactgcgc tccccccag   300 gtgcactacg actacaacgg cttcccctac tggggccagg gcaccctggt gacagtgtcc   360
tcc                                                                  363
```

```
<210> SEQ ID NO 5
<211> LENGTH: 110
<212> TYPE: PRT
<213> ORGANISM: Mus musculus

<400> SEQUENCE: 5

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu Gly
            100                 105                 110
```

```
<210> SEQ ID NO 6
<211> LENGTH: 330
<212> TYPE: DNA
<213> ORGANISM: Mus musculus

<400> SEQUENCE: 6
caggccgtgg tgacacagga gtcagctctg accacatccc caggcgaaac agtgactctg    60
acctgcagat ccagcactgg agcagtgact acctctaact acgctaattg ggtgcaggag   120
aagcccgacc acctgttcac tgggctgatc ggcggaacca caaaagggc accggtgtg    180
```

```
cctgcccggt tttctggcag tctgatcgga gacaaggccg ctctgacaat tactggcgcc    240
cagacagagg atgaagctat ttacttctgt gcactgtggt atagcaatct gtgggtgttt    300
gggggtggca ccaaactgac agtgctggga                                      330
```

<210> SEQ ID NO 7
<211> LENGTH: 125
<212> TYPE: PRT
<213> ORGANISM: Mus musculus

<400> SEQUENCE: 7

```
Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125
```

<210> SEQ ID NO 8
<211> LENGTH: 375
<212> TYPE: DNA
<213> ORGANISM: Mus musculus

<400> SEQUENCE: 8

```
gaggtgaagc tgctggaaag cggcggagga ctggtgcagc caaagggatc actgaaactg    60
tcctgcgccg cctccggctt caccttttaac acatacgcta tgaattgggt gcgacaggca   120
cctggcaagg gcctggagtg gtggcaagg atcaggtcca agtacaacaa ttatgcaacc   180
tactatgccg actctgtgaa ggatagattc acaatcagtc gcgacgattc ccagagcatt   240
ctgtatctgc agatgaacaa tctgaaaact gaagacaccg ccatgtacta ttgtgtgcgg   300
cacggtaact tcggcaattc ttacgtgtct tggtttgctt attggggaca ggggacactg   360
gtgactgtgt cttcc                                                     375
```

<210> SEQ ID NO 9
<211> LENGTH: 218
<212> TYPE: PRT
<213> ORGANISM: Homo sapiens

<400> SEQUENCE: 9

```
Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
```

```
            50                  55                  60
Glu Gln Tyr Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Ser Asn
                 85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215
```

<210> SEQ ID NO 10
<211> LENGTH: 106
<212> TYPE: PRT
<213> ORGANISM: Artificial Sequence
<220> FEATURE:
<223> OTHER INFORMATION: Amino Acid Sequence of Humanized mAb1 Variable
      Light Chain Variant 1

<400> SEQUENCE: 10

```
Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Leu Ile Tyr
        35                  40                  45

Asp Ser Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Arg Asn Pro Pro Thr
                85                  90                  95

Phe Gly Gly Gly Thr Lys Val Glu Ile Lys
            100                 105
```

<210> SEQ ID NO 11
<211> LENGTH: 318
<212> TYPE: DNA
<213> ORGANISM: Artificial Sequence
<220> FEATURE:
<223> OTHER INFORMATION: Polynucleotide Sequence Encoding Humanized mAb2
      Variable Light Chain Variant 1

<400> SEQUENCE: 11
gacatccaga tgacccagtc cccctccagc ctgtccgcct ctgtgggcga cagagtgaca      60
atcacctgtt ccgccagctc ctccgtgtcc tacatgaact ggtatcagca gaagcccggc    120

```
aaggcccca agcggctgat ctacgactcc tccaagctgg cctccggcgt gccctccaga        180
ttctccggct ctggctccgg caccgagttc accctgacca tctccagcct gcagcccgag        240
gacttcgcca cctactactg ccagcagtgg tcccggaacc ccctaccttt cggcggaggc        300
accaaggtgg aaatcaag                                                     318
```

```
<210> SEQ ID NO 12
<211> LENGTH: 106
<212> TYPE: PRT
<213> ORGANISM: Artificial Sequence
<220> FEATURE:
<223> OTHER INFORMATION: Amino Acid Sequence of Humanized mAb1 Variable
      Light Chain Variant 2 (mAb1 LC-2)

<400> SEQUENCE: 12
```

```
Asp Val Val Met Thr Gln Ser Pro Ala Ile Met Ser Ala Phe Pro Gly
1               5                   10                  15

Glu Lys Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Trp Ile Tyr
        35                  40                  45

Asp Ser Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Arg Asn Pro Pro Thr
                85                  90                  95

Phe Gly Gly Gly Thr Lys Val Glu Ile Lys
            100                 105
```

```
<210> SEQ ID NO 13
<211> LENGTH: 318
<212> TYPE: DNA
<213> ORGANISM: Artificial Sequence
<220> FEATURE:
<223> OTHER INFORMATION: Polynucleotide Sequence Encoding Humanized mAb2
      Variable Light Chain Variant 1

<400> SEQUENCE: 13
```

```
gacgtggtga tgacccagtc tcctgccatc atgagtgctt tcccaggcga gaaagtgacc         60
attacatgct ctgcttccag ctctgtgtcc tacatgaact ggtatcagca gaagccaggg        120
aaagcaccca gaggtggat ctacgactcc tccaagctgg cctccggcgt gccaagccgg         180
ttctctggta gtggctcagg aaccgagttt actctgacca tttccagcct gcagcctgaa        240
gatttcgcaa catactattg tcagcagtgg tccagaaatc ccctacatt tggcggaggg         300 actaaagtgg aaatcaag                                                     318
```

```
<210> SEQ ID NO 14
<211> LENGTH: 121
<212> TYPE: PRT
<213> ORGANISM: Artificial Sequence
<220> FEATURE:
<223> OTHER INFORMATION: Amino Acid Sequence of Humanized mAb1 Variable
      Heavy Chain

<400> SEQUENCE: 14
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Ser
            20                  25                  30
```

Thr Met His Trp Val Arg Gln Ala Pro Gly Gln Gly Leu Glu Trp Ile
            35                  40                  45

Gly Tyr Ile Asn Pro Ser Ser Ala Tyr Thr Asn Tyr Asn Gln Lys Phe
        50                  55                  60

Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
            85                  90                  95

Ala Ser Pro Gln Val His Tyr Asp Tyr Asn Gly Phe Pro Tyr Trp Gly
            100                 105                 110

Gln Gly Thr Leu Val Thr Val Ser Ser
            115                 120

<210> SEQ ID NO 15
<211> LENGTH: 363
<212> TYPE: DNA
<213> ORGANISM: Artificial Sequence
<220> FEATURE:
<223> OTHER INFORMATION: Polynucleotide Sequence Encoding Humanized mAb2
      Variable Light Chain Chain

<400> SEQUENCE: 15
caggtgcagc tggtgcagtc tggcgccgaa gtgaagaaac ctggcgcctc cgtgaaggtg      60
tcctgcaagg cctccggcta caccttcacc cggtccacca tgcactgggt gcgacaggcc     120
ccaggccagg gactggaatg gatcggctac atcaacccct ccagcgccta caccaactac     180
aaccagaaat tcaaggaccg cgtgaccatc accgccgaca gtccaccag caccgcctac      240 atggaactgt ctagcctgcg gagcgaggac accgccgtgt actactgcgc ctcccccag      300 gtgcactacg actacaacgg cttccctac tggggccagg gcaccctggt gacagtgtcc     360
tcc                                                                  363

<210> SEQ ID NO 16
<211> LENGTH: 110
<212> TYPE: PRT
<213> ORGANISM: Artificial Sequence
<220> FEATURE:
<223> OTHER INFORMATION: Amino Acid Sequence of Humanized mAb2 Variable
      Chain Variant 1 (h-mAb2 VL-1)

<400> SEQUENCE: 16

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Thr
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
            85                  90                  95

Leu Trp Val Phe Gly Gly Gly Thr Lys Leu Thr Val Leu Gly
            100                 105                 110

<210> SEQ ID NO 17
<211> LENGTH: 330

<212> TYPE: DNA
<213> ORGANISM: Artificial Sequence
<220> FEATURE:
<223> OTHER INFORMATION: Polynucleotide Sequence Encoding Humanized mAb2
      Variable Light Chain Variant 1 (h-mAb2 VL-1)

<400> SEQUENCE: 17
caggctgtgg tgactcagga gccttcactg accgtgtccc caggcggaac tgtgaccctg     60
acatgcagat ccagcacagg cgcagtgacc acatctaact acgccaattg gttccagcag    120
aagccaggac aggcaccaag gaccctgatc ggggtacaa acaaagggc tccctggacc      180 cctgcacggt tttctggaag tctgctgggc ggaaaggccg ctctgactat taccggggca    240
caggccgagg acgaagccga ttactattgt gctctgtggt atagcaatct gtgggtgttc    300
gggggtggca caaaactgac tgtgctggga                                      330

<210> SEQ ID NO 18
<211> LENGTH: 110
<212> TYPE: PRT
<213> ORGANISM: Artificial Sequence
<220> FEATURE:
<223> OTHER INFORMATION: Amino Acid Sequence of Humanized mAb2 Variable
      Chain Variant 2 (h-mAb2 VL-2)

<400> SEQUENCE: 18

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Thr
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 19
<211> LENGTH: 330
<212> TYPE: DNA
<213> ORGANISM: Artificial Sequence
<220> FEATURE:
<223> OTHER INFORMATION: Polynucleotide Sequence Encoding Humanized mAb2
      Variable Light Chain Variant 2 (h-mAb2 VL-2)

<400> SEQUENCE: 19
caggctgtgg tgactcagga gccttcactg accgtgtccc caggcggaac tgtgaccctg     60
acatgcagat ccagcacagg cgcagtgacc acatctaact acgccaattg ggtgcagcag    120
aagccaggac aggcaccaag gaccctgatc ggggtacaa acaaagggc tccctggacc      180 cctgcacggt tttctggaag tctgctgggc ggaaaggccg ctctgactat taccggggca    240
caggccgagg acgaagccga ttactattgt gctctgtggt atagcaatct gtgggtgttc    300
gggggtggca caaaactgac tgtgctggga                                      330

<210> SEQ ID NO 20
<211> LENGTH: 110
<212> TYPE: PRT

```
<213> ORGANISM: Artificial Sequence
<220> FEATURE:
<223> OTHER INFORMATION: Amino Acid Sequence of Humanized mAb2 Variable
      Chain Variant 3 (h-mAb2 VL-3)

<400> SEQUENCE: 20

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Glu Lys Pro Gly Gln Ala Pro Arg Thr
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 21
<211> LENGTH: 330
<212> TYPE: DNA
<213> ORGANISM: Artificial Sequence
<220> FEATURE:
<223> OTHER INFORMATION: Polynucleotide Sequence Encoding Humanized mAb2
      Variable Light Chain Variant 3 (h-mAb2 VL-3)

<400> SEQUENCE: 21
caggctgtgg tgactcagga gccttcactg accgtgtccc caggcggaac tgtgaccctg      60
acatgcagat ccagcacagg cgcagtgacc acatctaact acgccaattg gttccaggag     120
aagccaggac aggcaccaag gaccctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca caaaactgac tgtgctggga                                      330

<210> SEQ ID NO 22
<211> LENGTH: 110
<212> TYPE: PRT
<213> ORGANISM: Artificial Sequence
<220> FEATURE:
<223> OTHER INFORMATION: Amino Acid Sequence of Humanized mAb2 Variable
      Chain Variant 4 (h-mAb2 VL-4)

<400> SEQUENCE: 22

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95
```

Leu Trp Val Phe Gly Gly Gly Thr Lys Leu Thr Val Leu Gly
            100                 105                 110

<210> SEQ ID NO 23
<211> LENGTH: 330
<212> TYPE: DNA
<213> ORGANISM: Artificial Sequence
<220> FEATURE:
<223> OTHER INFORMATION: Polynucleotide Sequence Encoding Humanized mAb2
      Variable Light Chain Variant 4 (h-mAb2 VL-4)

<400> SEQUENCE: 23
caggctgtgg tgactcagga gccttcactg accgtgtccc caggcggaac tgtgaccctg    60
acatgcagat ccagcacagg cgcagtgacc acatctaact acgccaattg gttccagcag   120
aagccaggac aggcaccaag gggcctgatc gggggtacaa acaaaagggc tccctggacc   180
cctgcacggt tttctggaag tctgctgggc ggaaaggccg ctctgactat taccggggca   240
caggccgagg acgaagccga ttactattgt gctctgtggt atagcaatct gtgggtgttc   300
gggggtggca caaaactgac tgtgctggga                                    330

<210> SEQ ID NO 24
<211> LENGTH: 110
<212> TYPE: PRT
<213> ORGANISM: Artificial Sequence
<220> FEATURE:
<223> OTHER INFORMATION: Amino Acid Sequence of Humanized mAb2 Variable
      Chain Variant 5 (h-mAb2 VL-5)

<400> SEQUENCE: 24

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Ala Pro Arg Thr
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 25
<211> LENGTH: 330
<212> TYPE: DNA
<213> ORGANISM: Artificial Sequence
<220> FEATURE:
<223> OTHER INFORMATION: Polynucleotide Sequence Encoding Humanized mAb2
      Variable Light Chain Variant 5 (h-mAb2 VL-2)

<400> SEQUENCE: 25
caggctgtgg tgactcagga gccttcactg accgtgtccc caggcggaac tgtgaccctg    60
acatgcagat ccagcacagg cgcagtgacc acatctaact acgccaattg ggtgcaggag   120
aagccaggac aggcaccaag gaccctgatc gggggtacaa acaaaagggc tccctggacc   180
cctgcacggt tttctggaag tctgctgggc ggaaaggccg ctctgactat taccggggca   240
caggccgagg acgaagccga ttactattgt gctctgtggt atagcaatct gtgggtgttc   300

```
ggggtggca caaaactgac tgtgctggga                                         330
```

<210> SEQ ID NO 26
<211> LENGTH: 110
<212> TYPE: PRT
<213> ORGANISM: Artificial Sequence
<220> FEATURE:
<223> OTHER INFORMATION: Amino Acid Sequence of Humanized mAb2 Variable
      Chain Variant 6 (h-mAb2 VL-6)

<400> SEQUENCE: 26

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110
```

<210> SEQ ID NO 27
<211> LENGTH: 330
<212> TYPE: DNA
<213> ORGANISM: Artificial Sequence
<220> FEATURE:
<223> OTHER INFORMATION: Polynucleotide Sequence Encoding Humanized mAb2
      Variable Light Chain Variant 6 (h-mAb2 VL-6)

<400> SEQUENCE: 27

```
caggctgtgg tgactcagga gccttcactg accgtgtccc caggcggaac tgtgaccctg   60
acatgcagat ccagcacagg cgcagtgacc acatctaact acgccaattg ggtgcagcag  120
aagccaggac aggcaccaag gggcctgatc ggggtacaa acaaaagggc tccctggacc  180
cctgcacggt tttctggaag tctgctgggc ggaaaggccg ctctgactat taccggggca  240
caggccgagg acgaagccga ttactattgt gctctgtggt atagcaatct gtgggtgttc  300 ggggtggca caaaactgac tgtgctggga                                      330
```

<210> SEQ ID NO 28
<211> LENGTH: 110
<212> TYPE: PRT
<213> ORGANISM: Artificial Sequence
<220> FEATURE:
<223> OTHER INFORMATION: Amino Acid Sequence of Humanized mAb2 Variable
      Chain Variant 7 (h-mAb2 VL-7)

<400> SEQUENCE: 28

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Glu Lys Pro Gly Gln Ala Pro Arg Gly
        35                  40                  45

Leu Ile Gly Gly Thr Asn Lys Arg Ala Pro Trp Thr Pro Ala Arg Phe
```

-continued

```
                50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly
            100                 105                 110

<210> SEQ ID NO 29
<211> LENGTH: 330
<212> TYPE: DNA
<213> ORGANISM: Artificial Sequence
<220> FEATURE:
<223> OTHER INFORMATION: Polynucleotide Sequence Encoding Humanized mAb2
      Variable Light Chain Variant 7 (h-mAb2 VL-7)

<400> SEQUENCE: 29
caggctgtgg tgactcagga gccttcactg accgtgtccc caggcggaac tgtgaccctg      60
acatgcagat ccagcacagg cgcagtgacc acatctaact acgccaattg gttccaggag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca aaaactgac tgtgctggga                                       330

<210> SEQ ID NO 30
<211> LENGTH: 110
<212> TYPE: PRT
<213> ORGANISM: Artificial Sequence
<220> FEATURE:
<223> OTHER INFORMATION: Amino Acid Sequence of Humanized mAb2 Variable
      Chain Variant 8 (h-mAb2 VL-8)

<400> SEQUENCE: 30

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly
            100                 105                 110

<210> SEQ ID NO 31
<211> LENGTH: 330
<212> TYPE: DNA
<213> ORGANISM: Artificial Sequence
<220> FEATURE:
<223> OTHER INFORMATION: Polynucleotide Sequence Encoding Humanized mAb2
      Variable Light Chain Variant 8 (h-mAb2 VL-8)

<400> SEQUENCE: 31
caggctgtgg tgactcagga gccttcactg accgtgtccc caggcggaac tgtgaccctg      60
```

-continued

```
acatgcagat ccagcacagg cgcagtgacc acatctaact acgccaattg ggtgcaggag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca aaaactgac tgtgctggga                                       330
```

<210> SEQ ID NO 32
<211> LENGTH: 110
<212> TYPE: PRT
<213> ORGANISM: Artificial Sequence
<220> FEATURE:
<223> OTHER INFORMATION: Amino Acid Sequence of Humanized mAb2 Variable
      Chain Variant 9 (h-mAb2 VL-9)

<400> SEQUENCE: 32

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110
```

<210> SEQ ID NO 33
<211> LENGTH: 330
<212> TYPE: DNA
<213> ORGANISM: Artificial Sequence
<220> FEATURE:
<223> OTHER INFORMATION: Polynucleotide Sequence Encoding Humanized mAb2
      Variable Light Chain Variant 9 (h-mAb2 VL-9)

<400> SEQUENCE: 33

```
caggctgtgg tgactcagga gccttcactg accgtgtccc caggcggaac tgtgaccctg     60
acatgcagat ccagcacagg cgcagtgacc acatctaact acgccaattg ggtgcaggag     120
aagccaggac aggcattcag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca aaaactgac tgtgctggga                                       330
```

<210> SEQ ID NO 34
<211> LENGTH: 110
<212> TYPE: PRT
<213> ORGANISM: Artificial Sequence
<220> FEATURE:
<223> OTHER INFORMATION: Amino Acid Sequence of Humanized mAb2 Variable
      Chain Variant 10 (h-mAb2 VL-10)

<400> SEQUENCE: 34

```
Gln Ala Val Val Thr Gln Glu Pro Ser Leu Thr Val Ser Pro Gly Gly
1               5                   10                  15
```

Thr Val Thr Leu Thr Cys Arg Ser Ser Thr Gly Ala Val Thr Thr Ser
            20                  25                  30

Asn Tyr Ala Asn Trp Phe Gln Gln Lys Pro Asp His Leu Phe Thr Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 35
<211> LENGTH: 330
<212> TYPE: DNA
<213> ORGANISM: Artificial Sequence
<220> FEATURE:
<223> OTHER INFORMATION: Polynucleotide Sequence Encoding Humanized mAb2
      Variable Light Chain Variant 10 (h-mAb2 VL-10)

<400> SEQUENCE: 35
caggctgtgg tgactcagga gccttcactg accgtgtccc caggcggaac tgtgaccctg      60
acatgcagat ccagcactgg agcagtgact acctctaact acgctaattg gttccagcag     120
aagcccgacc acctgttcac tgggctgatc ggcggaacca caaaagggc tccctggacc      180 cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca caaaactgac tgtgctggga                                      330

<210> SEQ ID NO 36
<211> LENGTH: 125
<212> TYPE: PRT
<213> ORGANISM: Artificial Sequence
<220> FEATURE:
<223> OTHER INFORMATION: Amino Acid Sequence of Humanized mAb2 Heavy
      Chain Variant 1 (h-mAb2 VH-1)

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 37
<211> LENGTH: 375

<212> TYPE: DNA
<213> ORGANISM: Artificial Sequence
<220> FEATURE:
<223> OTHER INFORMATION: Polynucleotide Sequence Encoding Humanized mAb2
      Variable Heavy Chain Variant 1 (h-mAb2 VH-1)

<400> SEQUENCE: 37

```
gaggtgcagc tggtggaaag cggcggagga ctggtgcagc aggtggcag cctgcgactg    60
tcttgcgccg ctagtggctt cacctttct acatacgcca tgaactgggt gaggcaggct   120
cctggaaagg ggctggagtg ggtgggcagg atcaggtcca agtacaacaa ttatgcaacc   180
tactatgccg actcagtgaa ggatagattc acaatttccc gcgacgattc taaaaacagt   240
ctgtatctgc agatgaactc cctgaagact gaagacaccg ccgtgtacta ttgtgcaaga   300
cacggaaaact tcggcaactc ctacgtgtcc tggtttgcat attggggtca gggcacactg   360
gtgaccgtgt ccagc                                                    375
```

<210> SEQ ID NO 38
<211> LENGTH: 125
<212> TYPE: PRT
<213> ORGANISM: Artificial Sequence
<220> FEATURE:
<223> OTHER INFORMATION: Amino Acid Sequence of Humanized mAb2 Heavy
      Chain Variant 2 (h-mAb2 VH-2)

<400> SEQUENCE: 38

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 39
<211> LENGTH: 375
<212> TYPE: DNA
<213> ORGANISM: Artificial Sequence
<220> FEATURE:
<223> OTHER INFORMATION: Polynucleotide Sequence Encoding Humanized mAb2
      Variable Heavy Chain Variant 2 (h-mAb2 VH-2)

<400> SEQUENCE: 39

```
gaggtgcagc tggtggaaag cggcggagga ctggtgcagc aggtggcag cctgcgactg    60
tcttgcgccg ctagtggctt cacctttaac acatacgcca tgaactgggt gaggcaggct   120
cctggaaagg ggctggagtg ggtgggcagg atcaggtcca agtacaacaa ttatgcaacc   180
tactatgccg actcagtgaa ggatagattc acaatttccc gcgacgattc taaaaacagt   240
ctgtatctgc agatgaactc cctgaagact gaagacaccg ccgtgtacta ttgtgcaaga   300
cacggaaaact tcggcaactc ctacgtgtcc tggtttgcat attggggtca gggcacactg   360
```

```
gtgaccgtgt ccagc                                                     375
```

<210> SEQ ID NO 40
<211> LENGTH: 125
<212> TYPE: PRT
<213> ORGANISM: Artificial Sequence
<220> FEATURE:
<223> OTHER INFORMATION: Amino Acid Sequence of Humanized mAb2 Heavy
      Chain Variant 3 (h-mAb2 VH-3)

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 41
<211> LENGTH: 375
<212> TYPE: DNA
<213> ORGANISM: Artificial Sequence
<220> FEATURE:
<223> OTHER INFORMATION: Polynucleotide Sequence Encoding Humanized mAb2
      Variable Heavy Chain Variant 3 (h-mAb2 VH-3)

<400> SEQUENCE: 41

```
gaggtgcagc tggtggaaag cggcggagga ctggtgcagc caggtggcag cctgcgactg    60
tcttgcgccg ctagtggctt caccttttct acatacgcca tgaactgggt gaggcaggct   120
cctggaaagg gctggagtg gtggccagg atcaggtcca agtacaacaa ttatgcaacc    180
tactatgccg actcagtgaa ggatagattc acaatttccc gcgacgattc taaaaacagt   240
ctgtatctgc agatgaactc cctgaagact gaagacaccg ccgtgtacta ttgtgcaaga   300
cacggaaact tcggcaactc ctacgtgtcc tggtttgcat attggggtca gggcacactg   360
gtgaccgtgt ccagc                                                    375
```

<210> SEQ ID NO 42
<211> LENGTH: 125
<212> TYPE: PRT
<213> ORGANISM: Artificial Sequence
<220> FEATURE:
<223> OTHER INFORMATION: Amino Acid Sequence of Humanized mAb2 Heavy
      Chain Variant 4 (h-mAb2 VH-4)

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 43
<211> LENGTH: 375
<212> TYPE: DNA
<213> ORGANISM: Artificial Sequence
<220> FEATURE:
<223> OTHER INFORMATION: Polynucleotide Sequence Encoding Humanized mAb2
      Variable Heavy Chain Variant 4 (h-mAb2 VH-4)

<400> SEQUENCE: 43
gaggtgcagc tggtggaaag cggcggagga ctggtgcagc caggtggcag cctgcgactg      60
tcttgcgccg ctagtggctt cacctttcct acatacgcca tgaactgggt gaggcaggct     120
cctggaaagg gctggagtg ggtgggcagg atcaggtcca agtacaacaa ttatgcaacc     180
tactatgccg actcagtgaa ggatagattc acaatttccc gcgacgattc taaaaacagt    240
ctgtatctgc agatgaactc cctgaagact gaagacaccg ccgtgtacta ttgtgtgaga    300 cacggaaaact tcggcaactc ctacgtgtcc tggtttgcat attggggtca gggcacactg   360
gtgaccgtgt ccagc                                                      375

<210> SEQ ID NO 44
<211> LENGTH: 125
<212> TYPE: PRT
<213> ORGANISM: Artificial Sequence
<220> FEATURE:
<223> OTHER INFORMATION: Amino Acid Sequence of Humanized mAb2 Heavy
      Chain Variant 5 (h-mAb2 VH-5)

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 45
<211> LENGTH: 375
<212> TYPE: DNA
<213> ORGANISM: Artificial Sequence
<220> FEATURE:
<223> OTHER INFORMATION: Polynucleotide Sequence Encoding Humanized mAb2
      Variable Heavy Chain Variant 5 (h-mAb2 VH-5)

<400> SEQUENCE: 45

```
gaggtgcagc tggtggaaag cggcggagga ctggtgcagc caggtggcag cctgcgactg    60
tcttgcgccg ctagtggctt cacctttaac acatacgcca tgaactgggt gaggcaggct   120
cctggaaagg ggctggagtg ggtggccagg atcaggtcca agtacaacaa ttatgcaacc   180
tactatgccg actcagtgaa ggatagattc acaatttccc gcgacgattc taaaaacagt   240
ctgtatctgc agatgaactc cctgaagact gaagacaccg ccgtgtacta ttgtgcaaga   300 cacggaaaact tcggcaactc ctacgtgtcc tggtttgcat attggggtca gggcacactg   360
gtgaccgtgt ccagc                                                    375
```

<210> SEQ ID NO 46
<211> LENGTH: 125
<212> TYPE: PRT
<213> ORGANISM: Artificial Sequence
<220> FEATURE:
<223> OTHER INFORMATION: Amino Acid Sequence of Humanized mAb2 Heavy
      Chain Variant 6 (h-mAb2 VH-6)

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 47
<211> LENGTH: 375
<212> TYPE: DNA
<213> ORGANISM: Artificial Sequence
<220> FEATURE:
<223> OTHER INFORMATION: Polynucleotide Sequence Encoding Humanized mAb2
      Variable Heavy Chain Variant 6 (h-mAb2 VH-6)

<400> SEQUENCE: 47

```
gaggtgcagc tggtggaaag cggcggagga ctggtgcagc caggtggcag cctgcgactg    60
tcttgcgccg ctagtggctt cacctttaac acatacgcca tgaactgggt gaggcaggct   120
cctggaaagg ggctggagtg ggtgggcagg atcaggtcca agtacaacaa ttatgcaacc   180
tactatgccg actcagtgaa ggatagattc acaatttccc gcgacgattc taaaaacagt   240
```

```
ctgtatctgc agatgaactc cctgaagact gaagacaccg ccgtgtacta ttgtgtgaga    300
cacggaaact tcggcaactc ctacgtgtcc tggtttgcat attggggtca gggcacactg    360
gtgaccgtgt ccagc                                                    375
```

```
<210> SEQ ID NO 48
<211> LENGTH: 125
<212> TYPE: PRT
<213> ORGANISM: Artificial Sequence
<220> FEATURE:
<223> OTHER INFORMATION: Amino Acid Sequence of Humanized mAb2 Heavy
      Chain Variant 7 (h-mAb2 VH-7)

<400> SEQUENCE: 48
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

```
<210> SEQ ID NO 49
<211> LENGTH: 375
<212> TYPE: DNA
<213> ORGANISM: Artificial Sequence
<220> FEATURE:
<223> OTHER INFORMATION: Polynucleotide Sequence Encoding Humanized mAb2
      Variable Heavy Chain Variant 7 (h-mAb2 VH-7)

<400> SEQUENCE: 49
```

```
gaggtgcagc tggtggaaag cggcggagga ctggtgcagc caggtggcag cctgcgactg    60
tcttgcgccg ctagtggctt cacctttttct acatacgcca tgaactgggt gaggcaggct    120
cctggaaagg ggctggagtg ggtggccagg atcaggtcca agtacaacaa ttatgcaacc    180
tactatgccg actcagtgaa ggatagattc acaatttccc gcgacgattc taaaaacagt    240
ctgtatctgc agatgaactc cctgaagact gaagacaccg ccgtgtacta ttgtgtgaga    300
cacggaaact tcggcaactc ctacgtgtcc tggtttgcat attggggtca gggcacactg    360
gtgaccgtgt ccagc                                                    375
```

```
<210> SEQ ID NO 50
<211> LENGTH: 125
<212> TYPE: PRT
<213> ORGANISM: Artificial Sequence
<220> FEATURE:
<223> OTHER INFORMATION: Amino Acid Sequence of Humanized mAb2 Heavy
      Chain Variant 8 (h-mAb2 VH-8)

<400> SEQUENCE: 50
```

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 51
<211> LENGTH: 375
<212> TYPE: DNA
<213> ORGANISM: Artificial Sequence
<220> FEATURE:
<223> OTHER INFORMATION: Polynucleotide Sequence Encoding Humanized mAb2
      Variable Heavy Chain Variant 8 (h-mAb2 VH-8)

<400> SEQUENCE: 51

```
gaggtgcagc tggtggagtc tgggggaggc ttggtccagc ctggagggtc cctgagactc      60
tcctgtgcag cctctggatt caccttcaac acatacgcta tgaattgggt ccgccaggct     120
ccagggaagg ggctggagtg ggttgcaagg atcaggtcca agtacaacaa ttatgcaacc     180
tactatgccg actctgtgaa ggatagattc accatctcaa gagatgattc aaagaactca     240
ctgtatctgc aaatgaacag cctgaaaacc gaggacacgg ccgtgtatta ctgtgtgaga     300
cacggtaact tcggcaattc ttacgtgtct tggtttgctt attggggaca ggggacactg     360
gtgactgtgt cttcc                                                     375
```

<210> SEQ ID NO 52
<211> LENGTH: 125
<212> TYPE: PRT
<213> ORGANISM: Artificial Sequence
<220> FEATURE:
<223> OTHER INFORMATION: Amino Acid Sequence of Humanized mAb2 Variable
      Heavy Chain Variant QV (h-mAb2 VL-QV)

<400> SEQUENCE: 52

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110
```

Ala Tyr Trp Gly Gln Gly Thr Leu Val Thr Val Ser Ala
        115                 120                 125

<210> SEQ ID NO 53
<211> LENGTH: 375
<212> TYPE: DNA
<213> ORGANISM: Artificial Sequence
<220> FEATURE:
<223> OTHER INFORMATION: Polynucleotide Sequence Encoding Humanized mAb2
      Variable Heavy Chain Variant QV (h-mAb2 VL-QV)

<400> SEQUENCE: 53
gaggtgcagc tggtggaaag cggcggagga ctggtgcagc caaagggatc actgaaactg      60
tcctgcgccg cctccggctt cacctttaac acatacgcta tgaattgggt gcgacaggca     120
cctggcaagg gcctggagtg ggtggcaagg atcaggtcca agtacaacaa ttatgcaacc     180
tactatgccg actctgtgaa ggatagattc acaatcagtc gcgacgattc ccagagcatt     240
ctgtatctgc agatgaacaa tctgaaaact gaagacaccg ccatgtacta ttgtgtgcgg     300
cacggtaact tcggcaattc ttacgtgtct tggtttgctt attggggaca ggggacactg     360
gtgactgtgt cttcc                                                      375

<210> SEQ ID NO 54
<211> LENGTH: 125
<212> TYPE: PRT
<213> ORGANISM: Artificial Sequence
<220> FEATURE:
<223> OTHER INFORMATION: Amino acid sequence of hVH-6L

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Asn Lys Tyr Asn Asn Tyr Ala Thr Glu Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 55
<211> LENGTH: 125
<212> TYPE: PRT
<213> ORGANISM: Artificial Sequence
<220> FEATURE:
<223> OTHER INFORMATION: Amino acid sequence of hVH-8L

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

```
                35                  40                  45

Ala Arg Ile Arg Asn Lys Tyr Asn Asn Tyr Ala Thr Glu Tyr Ala Asp
            50                  55                  60

Ser Val Lys Asp Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 56
<211> LENGTH: 125
<212> TYPE: PRT
<213> ORGANISM: Artificial Sequence
<220> FEATURE:
<223> OTHER INFORMATION: Amino acid sequence of hXR32VH-8 di-1

<400> SEQUENCE: 56

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Thr Arg Ser Lys Ala Asn Ser Tyr Thr Thr Tyr Tyr Ala Ala
            50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 57
<211> LENGTH: 125
<212> TYPE: PRT
<213> ORGANISM: Artificial Sequence
<220> FEATURE:
<223> OTHER INFORMATION: Amino acid sequence of hXR32VH-8 di-2

<400> SEQUENCE: 57

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Gly Arg Thr Arg Ser Lys Ala Asn Ser Tyr Thr Thr Tyr Tyr Ala Ala
            50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                85                  90                  95
```

```
Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 58
<211> LENGTH: 272
<212> TYPE: PRT
<213> ORGANISM: Artificial Sequence
<220> FEATURE:
<223> OTHER INFORMATION: Amino acid sequence of the hXR32VL-Her-2VH E
      coil

<400> SEQUENCE: 58

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Gln Gln Ser Gly Pro Glu
        115                 120                 125

Leu Val Lys Pro Gly Ala Ser Leu Lys Leu Ser Cys Thr Ala Ser Gly
    130                 135                 140

Phe Asn Ile Lys Asp Thr Tyr Ile His Trp Val Lys Gln Arg Pro Glu
145                 150                 155                 160

Gln Gly Leu Glu Trp Ile Gly Arg Ile Tyr Pro Thr Asn Gly Tyr Thr
                165                 170                 175

Arg Tyr Asp Pro Lys Phe Gln Asp Lys Ala Thr Ile Thr Ala Asp Thr
            180                 185                 190

Ser Ser Asn Thr Ala Tyr Leu Gln Val Ser Arg Leu Thr Ser Glu Asp
        195                 200                 205

Thr Ala Val Tyr Tyr Cys Ser Arg Trp Gly Gly Asp Gly Phe Tyr Ala
    210                 215                 220

Met Asp Tyr Trp Gly Gln Gly Ala Ser Val Thr Val Ser Ser Gly Gly
225                 230                 235                 240

Cys Gly Gly Gly Lys Val Ala Ala Leu Lys Glu Lys Val Ala Ala Leu
                245                 250                 255

Lys Glu Lys Val Ala Ala Leu Lys Glu Lys Val Ala Ala Leu Lys Glu
            260                 265                 270
```

<210> SEQ ID NO 59
<211> LENGTH: 276
<212> TYPE: PRT
<213> ORGANISM: Artificial Sequence
<220> FEATURE:
<223> OTHER INFORMATION: Amino acid sequence of the Her2VL-hXR32VH-K
      coil

<400> SEQUENCE: 59

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
50                  55                  60

Asn Arg Ser Gly Thr Asp Phe Thr Phe Thr Ile Ser Ser Val Gln Ala
65                  70                  75                  80

Ala Asp Leu Ala Val Tyr Tyr Cys Gln Gln His Tyr Thr Thr Pro Pro
                85                  90                  95

Thr Phe Gly Gly Gly Thr Lys Leu Glu Ile Lys Arg Ala Gly Gly Gly
            100                 105                 110

Ser Gly Gly Gly Gly Glu Val Gln Leu Val Glu Ser Gly Gly Gly Leu
        115                 120                 125

Val Gln Pro Gly Gly Ser Leu Arg Leu Ser Cys Ala Ala Ser Gly Phe
    130                 135                 140

Thr Phe Asn Thr Tyr Ala Met Asn Trp Val Arg Gln Ala Pro Gly Lys
145                 150                 155                 160

Gly Leu Glu Trp Val Ala Arg Ile Arg Ser Lys Tyr Asn Asn Tyr Ala
                165                 170                 175

Thr Tyr Tyr Ala Asp Ser Val Lys Asp Arg Phe Thr Ile Ser Arg Asp
            180                 185                 190

Asp Ser Lys Asn Ser Leu Tyr Leu Gln Met Asn Ser Leu Lys Thr Glu
        195                 200                 205

Asp Thr Ala Val Tyr Tyr Cys Val Arg His Gly Asn Phe Gly Asn Ser
    210                 215                 220

Tyr Val Ser Trp Phe Ala Tyr Trp Gly Gln Gly Thr Leu Val Thr Val
225                 230                 235                 240

Ser Ser Gly Gly Cys Gly Gly Gly Glu Val Ala Ala Leu Glu Lys Glu
                245                 250                 255

Val Ala Ala Leu Glu Lys Glu Val Ala Ala Leu Glu Lys Glu Val Ala
            260                 265                 270

Ala Leu Glu Lys
        275

<210> SEQ ID NO 60
<211> LENGTH: 278
<212> TYPE: PRT
<213> ORGANISM: Artificial Sequence
<220> FEATURE:
<223> OTHER INFORMATION: Amino acid sequence of the CD19VL-hXR32VH-E
      coil

<400> SEQUENCE: 60

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80
```

```
Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Ser Gly Gly Gly Gly Glu Val Gln Leu Val Glu Ser Gly Gly
        115                 120                 125

Gly Leu Val Gln Pro Gly Gly Ser Leu Arg Leu Ser Cys Ala Ala Ser
    130                 135                 140

Gly Phe Thr Phe Asn Thr Tyr Ala Met Asn Trp Val Arg Gln Ala Pro
145                 150                 155                 160

Gly Lys Gly Leu Glu Trp Val Ala Arg Ile Arg Ser Lys Tyr Asn Asn
                165                 170                 175

Tyr Ala Thr Tyr Tyr Ala Asp Ser Val Lys Asp Arg Phe Thr Ile Ser
            180                 185                 190

Arg Asp Asp Ser Lys Asn Ser Leu Tyr Leu Gln Met Asn Ser Leu Lys
        195                 200                 205

Thr Glu Asp Thr Ala Val Tyr Tyr Cys Val Arg His Gly Asn Phe Gly
    210                 215                 220

Asn Ser Tyr Val Ser Trp Phe Ala Tyr Trp Gly Gln Gly Thr Leu Val
225                 230                 235                 240

Thr Val Ser Ser Gly Gly Cys Gly Gly Gly Glu Val Ala Ala Leu Glu
                245                 250                 255

Lys Glu Val Ala Ala Leu Glu Lys Glu Val Ala Ala Leu Glu Lys Glu
            260                 265                 270

Val Ala Ala Leu Glu Lys
        275
```

<210> SEQ ID NO 61
<211> LENGTH: 276
<212> TYPE: PRT
<213> ORGANISM: Artificial Sequence
<220> FEATURE:
<223> OTHER INFORMATION: Amino acid sequence of the hXR32VL-CD19VH-K coil

<400> SEQUENCE: 61

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Gln Gln Ser Gly Ala Glu
        115                 120                 125

Leu Val Arg Pro Gly Ser Ser Val Lys Ile Ser Cys Lys Ala Ser Gly
    130                 135                 140

Tyr Ala Phe Ser Ser Tyr Trp Met Asn Trp Val Lys Gln Arg Pro Gly
```

```
                145                 150                 155                 160
Gln Gly Leu Glu Trp Ile Gly Gln Ile Trp Pro Gly Asp Gly Asp Thr
                    165                 170                 175

Asn Tyr Asn Gly Lys Phe Lys Gly Lys Ala Thr Leu Thr Ala Asp Glu
                180                 185                 190

Ser Ser Ser Thr Ala Tyr Met Gln Leu Ser Ser Leu Ala Ser Glu Asp
                195                 200                 205

Ser Ala Val Tyr Phe Cys Ala Arg Arg Glu Thr Thr Thr Val Gly Arg
            210                 215                 220

Tyr Tyr Tyr Ala Met Asp Tyr Trp Gly Gln Gly Thr Thr Val Thr Val
225                 230                 235                 240

Ser Ser Gly Gly Cys Gly Gly Gly Lys Val Ala Ala Leu Lys Glu Lys
                    245                 250                 255

Val Ala Ala Leu Lys Glu Lys Val Ala Ala Leu Lys Glu Lys Val Ala
                260                 265                 270

Ala Leu Lys Glu
            275

<210> SEQ ID NO 62
<211> LENGTH: 271
<212> TYPE: PRT
<213> ORGANISM: Artificial Sequence
<220> FEATURE:
<223> OTHER INFORMATION: Amino acid sequence of the hXR32VL-EGFRVH-E
      coil

<400> SEQUENCE: 62

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
                100                 105                 110

Gly Ser Gly Gly Gly Gly Gln Val Gln Leu Lys Gln Ser Gly Pro Gly
            115                 120                 125

Leu Val Gln Pro Ser Gln Ser Leu Ser Ile Thr Cys Thr Val Ser Gly
        130                 135                 140

Phe Ser Leu Thr Asn Tyr Gly Val His Trp Val Arg Gln Ser Pro Gly
145                 150                 155                 160

Lys Gly Leu Glu Trp Leu Gly Val Ile Trp Ser Gly Gly Asn Thr Asp
                165                 170                 175

Tyr Asn Thr Pro Phe Thr Ser Arg Leu Ser Ile Asn Lys Asp Asn Ser
                180                 185                 190

Lys Ser Gln Val Phe Phe Lys Met Asn Ser Leu Gln Ser Asn Asp Thr
            195                 200                 205

Ala Ile Tyr Tyr Cys Ala Arg Ala Leu Thr Tyr Tyr Asp Tyr Glu Phe
        210                 215                 220
```

```
Ala Tyr Trp Gly Gln Gly Thr Leu Val Thr Val Ser Ser Gly Gly Cys
225                 230                 235                 240

Gly Gly Gly Glu Val Ala Ala Leu Glu Lys Glu Val Ala Ala Leu Glu
            245                 250                 255

Lys Glu Val Ala Ala Leu Glu Lys Glu Val Ala Ala Leu Glu Lys
        260                 265                 270
```

<210> SEQ ID NO 63
<211> LENGTH: 274
<212> TYPE: PRT
<213> ORGANISM: Artificial Sequence
<220> FEATURE:
<223> OTHER INFORMATION: Amino acid sequence of the EGFRVL-hXR32VH-K coil

<400> SEQUENCE: 63

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
    130                 135                 140

Asn Thr Tyr Ala Met Asn Trp Val Arg Gln Ala Pro Gly Lys Gly Leu
145                 150                 155                 160

Glu Trp Val Ala Arg Ile Arg Ser Lys Tyr Asn Asn Tyr Ala Thr Tyr
                165                 170                 175

Tyr Ala Asp Ser Val Lys Asp Arg Phe Thr Ile Ser Arg Asp Asp Ser
            180                 185                 190

Lys Asn Ser Leu Tyr Leu Gln Met Asn Ser Leu Lys Thr Glu Asp Thr
        195                 200                 205

Ala Val Tyr Tyr Cys Val Arg His Gly Asn Phe Gly Asn Ser Tyr Val
    210                 215                 220

Ser Trp Phe Ala Tyr Trp Gly Gln Gly Thr Leu Val Thr Val Ser Ser
225                 230                 235                 240

Gly Gly Cys Gly Gly Gly Lys Val Ala Ala Leu Lys Glu Lys Val Ala
                245                 250                 255

Ala Leu Lys Glu Lys Val Ala Ala Leu Lys Glu Lys Val Ala Ala Leu
            260                 265                 270

Lys Glu
```

<210> SEQ ID NO 64
<211> LENGTH: 275
<212> TYPE: PRT
<213> ORGANISM: Artificial Sequence
<220> FEATURE:

<223> OTHER INFORMATION: Amino acid sequence of the hBRCA69DVL-hXR32VH-E
      coil

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Asn Thr Leu Pro Pro
                85                  90                  95

Thr Phe Gly Gly Gly Thr Lys Leu Glu Ile Lys Gly Gly Gly Gly Ser
            100                 105                 110

Gly Gly Gly Gly Glu Val Gln Leu Val Glu Ser Gly Gly Gly Leu Val
            115                 120                 125

Gln Pro Gly Gly Ser Leu Arg Leu Ser Cys Ala Ala Ser Gly Phe Thr
130                 135                 140

Phe Asn Thr Tyr Ala Met Asn Trp Val Arg Gln Ala Pro Gly Lys Gly
145                 150                 155                 160

Leu Glu Trp Val Ala Arg Ile Arg Ser Lys Tyr Asn Asn Tyr Ala Thr
                165                 170                 175

Tyr Tyr Ala Asp Ser Val Lys Asp Arg Phe Thr Ile Ser Arg Asp Asp
            180                 185                 190

Ser Lys Asn Ser Leu Tyr Leu Gln Met Asn Ser Leu Lys Thr Glu Asp
        195                 200                 205

Thr Ala Val Tyr Tyr Cys Val Arg His Gly Asn Phe Gly Asn Ser Tyr
210                 215                 220

Val Ser Trp Phe Ala Tyr Trp Gly Gln Gly Thr Leu Val Thr Val Ser
225                 230                 235                 240

Ser Gly Gly Cys Gly Gly Glu Val Ala Ala Leu Glu Lys Glu Val
                245                 250                 255

Ala Ala Leu Glu Lys Glu Val Ala Ala Leu Glu Lys Glu Val Ala Ala
            260                 265                 270

Leu Glu Lys
        275

<210> SEQ ID NO 65
<211> LENGTH: 272
<212> TYPE: PRT
<213> ORGANISM: Artificial Sequence
<220> FEATURE:
<223> OTHER INFORMATION: Amino acid sequence of the hXR32VL-hBRCA69DVH-K
      coil

<400> SEQUENCE: 65

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
            115                 120                 125

Val Lys Lys Pro Gly Ala Ser Val Lys Val Ser Cys Lys Ala Ser Gly
130                 135                 140

Tyr Thr Phe Thr Ser Tyr Trp Met Gln Trp Val Arg Gln Ala Pro Gly
145                 150                 155                 160

Gln Gly Leu Glu Trp Met Gly Thr Ile Tyr Pro Gly Asp Gly Asp Thr
                165                 170                 175

Arg Tyr Thr Gln Lys Phe Lys Gly Arg Val Thr Ile Thr Ala Asp Lys
            180                 185                 190

Ser Thr Ser Thr Ala Tyr Met Glu Leu Ser Ser Leu Arg Ser Glu Asp
            195                 200                 205

Thr Ala Val Tyr Tyr Cys Ala Arg Arg Gly Ile Pro Arg Leu Trp Tyr
210                 215                 220

Phe Asp Val Trp Gly Gln Gly Thr Thr Val Thr Val Ser Ser Gly Gly
225                 230                 235                 240

Cys Gly Gly Lys Val Ala Ala Leu Lys Glu Lys Val Ala Ala Leu
                245                 250                 255

Lys Glu Lys Val Ala Ala Leu Lys Glu Lys Val Ala Ala Leu Lys Glu
            260                 265                 270

<210> SEQ ID NO 66
<211> LENGTH: 275
<212> TYPE: PRT
<213> ORGANISM: Artificial Sequence
<220> FEATURE:
<223> OTHER INFORMATION: Amino acid sequence of the hBRCA84DVL-hXR32VH-E
      coil

<400> SEQUENCE: 66

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys Gly Gly Gly Gly Ser
            100                 105                 110

Gly Gly Gly Gly Glu Val Gln Leu Val Glu Ser Gly Gly Gly Leu Val
            115                 120                 125

Gln Pro Gly Gly Ser Leu Arg Leu Ser Cys Ala Ala Ser Gly Phe Thr
            130                 135                 140

```
Phe Asn Thr Tyr Ala Met Asn Trp Val Arg Gln Ala Pro Gly Lys Gly
145                 150                 155                 160

Leu Glu Trp Val Ala Arg Ile Arg Ser Lys Tyr Asn Asn Tyr Ala Thr
                165                 170                 175

Tyr Tyr Ala Asp Ser Val Lys Asp Arg Phe Thr Ile Ser Arg Asp Asp
            180                 185                 190

Ser Lys Asn Ser Leu Tyr Leu Gln Met Asn Ser Leu Lys Thr Glu Asp
        195                 200                 205

Thr Ala Val Tyr Tyr Cys Val Arg His Gly Asn Phe Gly Asn Ser Tyr
    210                 215                 220

Val Ser Trp Phe Ala Tyr Trp Gly Gln Gly Thr Leu Val Thr Val Ser
225                 230                 235                 240

Ser Gly Gly Cys Gly Gly Gly Glu Val Ala Ala Leu Glu Lys Glu Val
                245                 250                 255

Ala Ala Leu Glu Lys Glu Val Ala Ala Leu Glu Lys Glu Val Ala Ala
            260                 265                 270

Leu Glu Lys
        275

<210> SEQ ID NO 67
<211> LENGTH: 274
<212> TYPE: PRT
<213> ORGANISM: Artificial Sequence
<220> FEATURE:
<223> OTHER INFORMATION: Amino acid sequence of the hXR32VL-hBRCA84DVH-K
      coil

<400> SEQUENCE: 67

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
            85                  90                  95

Leu Trp Val Phe Gly Gly Gly Thr Lys Leu Thr Val Leu Gly Gly Gly
        100                 105                 110

Gly Ser Gly Gly Gly Gly Glu Val Gln Leu Val Glu Ser Gly Gly Gly
    115                 120                 125

Leu Val Gln Pro Gly Gly Ser Leu Arg Leu Ser Cys Ala Ala Ser Gly
        130                 135                 140

Phe Thr Phe Ser Ser Phe Gly Met His Trp Val Arg Gln Ala Pro Gly
145                 150                 155                 160

Lys Gly Leu Glu Trp Val Ala Tyr Ile Ser Ser Asp Ser Ser Ala Ile
                165                 170                 175

Tyr Tyr Ala Asp Thr Val Lys Gly Arg Phe Thr Ile Ser Arg Asp Asn
            180                 185                 190

Ala Lys Asn Ser Leu Tyr Leu Gln Met Asn Ser Leu Arg Asp Glu Asp
        195                 200                 205

Thr Ala Val Tyr Tyr Cys Gly Arg Gly Arg Glu Asn Ile Tyr Tyr Gly
```

-continued

```
            210                 215                 220
Ser Arg Leu Asp Tyr Trp Gly Gln Gly Thr Thr Val Thr Val Ser Ser
225                 230                 235                 240

Gly Gly Cys Gly Gly Gly Lys Val Ala Ala Leu Lys Glu Lys Val Ala
                245                 250                 255

Ala Leu Lys Glu Lys Val Ala Ala Leu Lys Glu Lys Val Ala Ala Leu
            260                 265                 270

Lys Glu

<210> SEQ ID NO 68
<211> LENGTH: 279
<212> TYPE: PRT
<213> ORGANISM: Artificial Sequence
<220> FEATURE:
<223> OTHER INFORMATION: Amino acid sequence of the 4420VL-hXR32VH-E
      coil

<400> SEQUENCE: 68

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Gly Gly Ser Gly Gly Gly Gly Glu Val Gln Leu Val Glu Ser Gly
        115                 120                 125

Gly Gly Leu Val Gln Pro Gly Gly Ser Leu Arg Leu Ser Cys Ala Ala
    130                 135                 140

Ser Gly Phe Thr Phe Asn Thr Tyr Ala Met Asn Trp Val Arg Gln Ala
145                 150                 155                 160

Pro Gly Lys Gly Leu Glu Trp Val Ala Arg Ile Arg Ser Lys Tyr Asn
                165                 170                 175

Asn Tyr Ala Thr Tyr Tyr Ala Asp Ser Val Lys Asp Arg Phe Thr Ile
            180                 185                 190

Ser Arg Asp Asp Ser Lys Asn Ser Leu Tyr Leu Gln Met Asn Ser Leu
        195                 200                 205

Lys Thr Glu Asp Thr Ala Val Tyr Tyr Cys Val Arg His Gly Asn Phe
    210                 215                 220

Gly Asn Ser Tyr Val Ser Trp Phe Ala Tyr Trp Gly Gln Gly Thr Leu
225                 230                 235                 240

Val Thr Val Ser Ser Gly Gly Cys Gly Gly Gly Glu Val Ala Ala Leu
                245                 250                 255

Glu Lys Glu Val Ala Ala Leu Glu Lys Glu Val Ala Ala Leu Glu Lys
            260                 265                 270

Glu Val Ala Ala Leu Glu Lys
        275
```

```
<210> SEQ ID NO 69
<211> LENGTH: 270
<212> TYPE: PRT
<213> ORGANISM: Artificial Sequence
<220> FEATURE:
<223> OTHER INFORMATION: Amino acid sequence of the hXR32VL-4420VH-K
      coil

<400> SEQUENCE: 69

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Lys Leu Asp Glu Thr Gly Gly Gly
        115                 120                 125

Leu Val Gln Pro Gly Arg Pro Met Lys Leu Ser Cys Val Ala Ser Gly
    130                 135                 140

Phe Thr Phe Ser Asp Tyr Trp Met Asn Trp Val Arg Gln Ser Pro Glu
145                 150                 155                 160

Lys Gly Leu Glu Trp Val Ala Gln Ile Arg Asn Lys Pro Tyr Asn Tyr
                165                 170                 175

Glu Thr Tyr Tyr Ser Asp Ser Val Lys Gly Arg Phe Thr Ile Ser Arg
            180                 185                 190

Asp Asp Ser Lys Ser Ser Val Tyr Leu Gln Met Asn Asn Leu Arg Val
        195                 200                 205

Glu Asp Met Gly Ile Tyr Tyr Cys Thr Gly Ser Tyr Tyr Gly Met Asp
    210                 215                 220

Tyr Trp Gly Gln Gly Thr Ser Val Thr Val Ser Ser Gly Gly Cys Gly
225                 230                 235                 240

Gly Gly Lys Val Ala Ala Leu Lys Glu Lys Val Ala Ala Leu Lys Glu
                245                 250                 255

Lys Val Ala Ala Leu Lys Glu Lys Val Ala Ala Leu Lys Glu
            260                 265                 270

<210> SEQ ID NO 70
<211> LENGTH: 274
<212> TYPE: PRT
<213> ORGANISM: Artificial Sequence
<220> FEATURE:
<223> OTHER INFORMATION: Amino acid sequence of the RECA47VL-hXR32VH-K
      coil

<400> SEQUENCE: 70

Gln Ile Val Leu Thr Gln Ser Pro Ala Ile Met Ser Ala Ser Pro Gly
1               5                   10                  15

Glu Arg Val Thr Met Thr Cys Ser Ala Arg Ser Ser Ile Ser Phe Met
            20                  25                  30

Tyr Trp Tyr Gln Gln Lys Pro Gly Ser Ser Pro Arg Leu Leu Ile Tyr
```

```
            35                  40                  45
Asp Thr Ser Asn Leu Ala Ser Gly Val Pro Val Arg Phe Ser Gly Ser
 50                  55                  60
Gly Ser Gly Thr Ser Tyr Ser Leu Thr Ile Ser Arg Met Glu Ala Glu
 65                  70                  75                  80
Asp Ala Ala Thr Tyr Tyr Cys Gln Gln Trp Ser Ser Tyr Pro Leu Thr
                 85                  90                  95
Phe Gly Ser Gly Thr Lys Leu Glu Leu Lys Arg Gly Gly Gly Ser Gly
                100                 105                 110
Gly Gly Gly Glu Val Gln Leu Val Glu Ser Gly Gly Gly Leu Val Gln
            115                 120                 125
Pro Gly Gly Ser Leu Arg Leu Ser Cys Ala Ala Ser Gly Phe Thr Phe
130                 135                 140
Asn Thr Tyr Ala Met Asn Trp Val Arg Gln Ala Pro Gly Lys Gly Leu
145                 150                 155                 160
Glu Trp Val Ala Arg Ile Arg Ser Lys Tyr Asn Asn Tyr Ala Thr Tyr
                165                 170                 175
Tyr Ala Asp Ser Val Lys Asp Arg Phe Thr Ile Ser Arg Asp Asp Ser
                180                 185                 190
Lys Asn Ser Leu Tyr Leu Gln Met Asn Ser Leu Lys Thr Glu Asp Thr
            195                 200                 205
Ala Val Tyr Tyr Cys Val Arg His Gly Asn Phe Gly Asn Ser Tyr Val
210                 215                 220
Ser Trp Phe Ala Tyr Trp Gly Gln Gly Thr Leu Val Thr Val Ser Ser
225                 230                 235                 240
Gly Gly Cys Gly Gly Gly Lys Val Ala Ala Leu Lys Glu Lys Val Ala
                245                 250                 255
Ala Leu Lys Glu Lys Val Ala Ala Leu Lys Glu Lys Val Ala Ala Leu
            260                 265                 270
Lys Glu

<210> SEQ ID NO 71
<211> LENGTH: 271
<212> TYPE: PRT
<213> ORGANISM: Artificial Sequence
<220> FEATURE:
<223> OTHER INFORMATION: Amino acid sequence of the hXR32VL-RECA47VH-E
      coil

<400> SEQUENCE: 71

Gln Ala Val Val Thr Gln Glu Pro Ser Leu Thr Val Ser Pro Gly Gly
 1               5                  10                  15
Thr Val Thr Leu Thr Cys Arg Ser Ser Thr Gly Ala Val Thr Thr Ser
                20                  25                  30
Asn Tyr Ala Asn Trp Val Gln Gln Lys Pro Gly Gln Ala Pro Arg Gly
            35                  40                  45
Leu Ile Gly Gly Thr Asn Lys Arg Ala Pro Trp Thr Pro Ala Arg Phe
 50                  55                  60
Ser Gly Ser Leu Leu Gly Gly Lys Ala Ala Leu Thr Ile Thr Gly Ala
 65                  70                  75                  80
Gln Ala Glu Asp Glu Ala Asp Tyr Tyr Cys Ala Leu Trp Tyr Ser Asn
                85                  90                  95
Leu Trp Val Phe Gly Gly Gly Thr Lys Leu Thr Val Leu Gly Gly Gly
                100                 105                 110
Gly Ser Gly Gly Gly Gly Gln Val Gln Leu Gln Gln Ser Gly Pro Glu
```

```
            115                 120                 125
Leu Val Lys Pro Gly Ala Ser Val Lys Ile Ser Cys Lys Ala Ser Gly
    130                 135                 140

Tyr Thr Phe Ser Gly Ser Trp Met Asn Trp Val Lys Gln Arg Pro Gly
145                 150                 155                 160

Gln Gly Leu Glu Trp Ile Gly Arg Ile Tyr Pro Gly Asp Gly Glu Thr
                165                 170                 175

Asn Tyr Asn Gly Lys Phe Lys Asp Lys Ala Thr Leu Thr Ala Asp Lys
            180                 185                 190

Ser Ser Thr Thr Ala Tyr Met Glu Leu Ser Ser Leu Thr Ser Val Asp
            195                 200                 205

Ser Ala Val Tyr Phe Cys Ala Arg Ile Tyr Gly Asn Asn Val Tyr Phe
    210                 215                 220

Asp Val Trp Gly Ala Gly Thr Thr Val Thr Val Ser Ser Gly Gly Cys
225                 230                 235                 240

Gly Gly Gly Glu Val Ala Ala Leu Glu Lys Glu Val Ala Ala Leu Glu
                245                 250                 255

Lys Glu Val Ala Ala Leu Glu Lys Glu Val Ala Ala Leu Glu Lys
            260                 265                 270

<210> SEQ ID NO 72
<211> LENGTH: 125
<212> TYPE: PRT
<213> ORGANISM: Artificial Sequence
<220> FEATURE:
<223> OTHER INFORMATION: Amino acid sequence of hVH-6M

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Glu Tyr Ala Ala
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 73
<211> LENGTH: 375
<212> TYPE: DNA
<213> ORGANISM: Artificial Sequence
<220> FEATURE:
<223> OTHER INFORMATION: Polynucleotide Sequence Encoding hVH-6M
      Variable Heavy Chain

<400> SEQUENCE: 73
gaggtgcagc tggtggagtc tgggggaggc ttggtccagc ctggagggtc cctgagactc      60
tcctgtgcag cctctggatt caccttcaac acatacgcta tgaattgggt ccgccaggct     120
ccagggaagg ggctggagtg ggttggaagg atcaggtcca agtacaacaa ttatgcaacc     180
```

```
gagtatgccg actctgtgaa ggatagattc accatctcaa gagatgattc aaagaactca    240
ctgtatctgc aaatgaacag cctgaaaacc gaggacacgg ccgtgtatta ctgtgtgaga    300
cacggtaact tcggcaattc ttacgtgtct tggtttgctt attggggaca ggggacactg    360
gtgactgtgt cttcc                                                    375

<210> SEQ ID NO 74
<211> LENGTH: 125
<212> TYPE: PRT
<213> ORGANISM: Artificial Sequence
<220> FEATURE:
<223> OTHER INFORMATION: Amino acid sequence of hVH-8M

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Asn Lys Tyr Asn Asn Tyr Ala Thr Glu Tyr Ala Ala
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 75
<211> LENGTH: 375
<212> TYPE: DNA
<213> ORGANISM: Artificial Sequence
<220> FEATURE:
<223> OTHER INFORMATION: Polynucleotide Sequence Encoding hVH-8M
      Variable Heavy Chain

<400> SEQUENCE: 75
gaggtgcagc tggtggagtc tgggggaggc ttggtccagc ctggagggtc cctgagactc    60
tcctgtgcag cctctggatt caccttcaac acatacgcta tgaattgggt ccgccaggct    120
ccagggaagg ggctggagtg ggttgcaagg atcaggaaca agtacaacaa ttatgcaacc    180
gagtatgccg actctgtgaa ggatagattc accatctcaa gagatgattc aaagaactca    240
ctgtatctgc aaatgaacag cctgaaaacc gaggacacgg ccgtgtatta ctgtgtgaga    300
cacggtaact tcggcaattc ttacgtgtct tggtttgctt attggggaca ggggacactg    360
gtgactgtgt cttcc                                                    375

<210> SEQ ID NO 76
<211> LENGTH: 125
<212> TYPE: PRT
<213> ORGANISM: Artificial Sequence
<220> FEATURE:
<223> OTHER INFORMATION: Amino Acid Sequence of variant "a" (I51T Y52cA)
      of humanized mAb2 murine monoclonal antibody variable heavy chain

<400> SEQUENCE: 76
```

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Thr Ala Ser Lys Ala Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 77
<211> LENGTH: 125
<212> TYPE: PRT
<213> ORGANISM: Artificial Sequence
<220> FEATURE:
<223> OTHER INFORMATION: Amino Acid Sequence of variant "b" (I51T N54S)
      of humanized mAb2 murine monoclonal antibody variable heavy chain

<400> SEQUENCE: 77

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Thr Arg Ser Lys Tyr Asn Ser Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 78
<211> LENGTH: 125
<212> TYPE: PRT
<213> ORGANISM: Artificial Sequence
<220> FEATURE:
<223> OTHER INFORMATION: Amino Acid Sequence of variant "c" (I51T A56T)
      of humanized mAb2 murine monoclonal antibody variable heavy chain

<400> SEQUENCE: 78

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

```
Ala Arg Thr Arg Ser Lys Tyr Asn Asn Tyr Thr Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 79
<211> LENGTH: 125
<212> TYPE: PRT
<213> ORGANISM: Artificial Sequence
<220> FEATURE:
<223> OTHER INFORMATION: Amino Acid Sequence of variant "d" (I51T Y52cA
      N54S) of humanized mAb2 murine monoclonal antibody variable heavy
      chain

<400> SEQUENCE: 79

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Thr Arg Ser Lys Ala Asn Ser Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 80
<211> LENGTH: 125
<212> TYPE: PRT
<213> ORGANISM: Artificial Sequence
<220> FEATURE:
<223> OTHER INFORMATION: Amino Acid Sequence of variant "e" (I51T N54S
      A56T) of humanized mAb2 murine monoclonal antibody variable heavy
      chain

<400> SEQUENCE: 80

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Thr Arg Ser Lys Tyr Asn Ser Tyr Thr Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
```

```
                85                  90                  95
Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ala
        115                 120                 125

<210> SEQ ID NO 81
<211> LENGTH: 125
<212> TYPE: PRT
<213> ORGANISM: Artificial Sequence
<220> FEATURE:
<223> OTHER INFORMATION: Amino Acid Sequence of variant "f" (I51T Y52cA
      N54S A56T) of humanized mAb2 murine monoclonal antibody variable
      heavy chain

<400> SEQUENCE: 81

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
        35                  40                  45

Ala Arg Thr Arg Ser Lys Ala Asn Ser Tyr Thr Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ala
        115                 120                 125

<210> SEQ ID NO 82
<211> LENGTH: 125
<212> TYPE: PRT
<213> ORGANISM: Artificial Sequence
<220> FEATURE:
<223> OTHER INFORMATION: Amino Acid Sequence of variant "g" (I51T D61A)
      of humanized mAb2 murine monoclonal antibody variable heavy chain

<400> SEQUENCE: 82

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
        35                  40                  45

Ala Arg Thr Arg Ser Lys Tyr Asn Asn Tyr Ala Thr Tyr Tyr Ala Ala
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ala
        115                 120                 125
```

```
<210> SEQ ID NO 83
<211> LENGTH: 125
<212> TYPE: PRT
<213> ORGANISM: Artificial Sequence
<220> FEATURE:
<223> OTHER INFORMATION: Amino Acid Sequence of variant "h" (I51T D65G)
      of humanized mAb2 murine monoclonal antibody variable heavy chain

<400> SEQUENCE: 83

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Thr Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 84
<211> LENGTH: 125
<212> TYPE: PRT
<213> ORGANISM: Artificial Sequence
<220> FEATURE:
<223> OTHER INFORMATION: Amino Acid Sequence of variant "i" (I51T Y52cA
      N54S D61A) of humanized mAb2 murine monoclonal antibody variable
      heavy chain

<400> SEQUENCE: 84

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Thr Arg Ser Lys Ala Asn Ser Tyr Ala Thr Tyr Tyr Ala Ala
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 85
<211> LENGTH: 125
<212> TYPE: PRT
<213> ORGANISM: Artificial Sequence
<220> FEATURE:
<223> OTHER INFORMATION: Amino Acid Sequence of variant "j" (I51T Y52cA
      N54S D65G) of humanized mAb2 murine monoclonal antibody variable
``` heavy chain

<400> SEQUENCE: 85

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Thr Arg Ser Lys Ala Asn Ser Tyr Ala Thr Tyr Tyr Ala Asp
    50                  55                  60

Ser Val Lys Gly Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 86
<211> LENGTH: 125
<212> TYPE: PRT
<213> ORGANISM: Artificial Sequence
<220> FEATURE:
<223> OTHER INFORMATION: Amino Acid Sequence of variant "k" (I51T Y52cA
      N54S D61A D65G) of humanized mAb2 murine monoclonal antibody
      variable heavy chain

<400> SEQUENCE: 86

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Thr Arg Ser Lys Ala Asn Ser Tyr Ala Thr Tyr Tyr Ala Ala
    50                  55                  60

Ser Val Lys Gly Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 87
<211> LENGTH: 125
<212> TYPE: PRT
<213> ORGANISM: Artificial Sequence
<220> FEATURE:
<223> OTHER INFORMATION: Amino Acid Sequence of variant "2k" (I51T Y52cA
      N54S D61A D65G (VH8-A49G V93A)) of humanized mAb2 murine
      monoclonal antibody variable heavy chain

<400> SEQUENCE: 87

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Gly Arg Thr Arg Ser Lys Ala Asn Ser Tyr Thr Thr Tyr Tyr Ala Ala
         50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                     85                  90                  95

Tyr Cys Ala Arg His Gly Asn Phe Gly Asn Ser Tyr Val Ser Trp Phe
                    100                 105                 110

Ala Tyr Trp Gly Gln Gly Thr Leu Val Thr Val Ser Ser
            115                 120                 125

<210> SEQ ID NO 88
<211> LENGTH: 125
<212> TYPE: PRT
<213> ORGANISM: Artificial Sequence
<220> FEATURE:
<223> OTHER INFORMATION: Amino Acid Sequence of variant "5k" (I51T Y52cA
      N54S D61A D65G (VH8-V93A)) of humanized mAb2 murine monoclonal
      antibody variable heavy chain

<400> SEQUENCE: 88

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Thr Arg Ser Lys Ala Asn Ser Tyr Thr Thr Tyr Tyr Ala Ala
         50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                     85                  90                  95

Tyr Cys Ala Arg His Gly Asn Phe Gly Asn Ser Tyr Val Ser Trp Phe
                    100                 105                 110

Ala Tyr Trp Gly Gln Gly Thr Leu Val Thr Val Ser Ser
            115                 120                 125
```